United States Patent
Frimer et al.

(10) Patent No.: US 10,052,157 B2
(45) Date of Patent: Aug. 21, 2018

(54) DEVICE AND METHOD FOR ASSISTING LAPAROSCOPIC SURGERY—RULE BASED APPROACH

(71) Applicant: M.S.T. MEDICAL SURGERY TECHNOLOGIES LTD, Yoqneam (IL)

(72) Inventors: Motti Frimer, Zichron Yaakov (IL); Mordehai Sholev, Amikam (IL); Yehuda Pfeffer, Moshav Adirim (IL)

(73) Assignee: M.S.T. MEDICAL SURGERY TECHNOLOGIES LTD, Yoqneam (IL)

( * ) Notice: Subject to any disclaimer, the term of this patent is extended or adjusted under 35 U.S.C. 154(b) by 0 days.

(21) Appl. No.: 14/817,245

(22) Filed: Aug. 4, 2015

(65) Prior Publication Data
US 2016/0015473 A1 Jan. 21, 2016

Related U.S. Application Data

(63) Continuation-in-part of application No. 14/150,939, filed on Jan. 9, 2014, now Pat. No. 9,204,939, which
(Continued)

(51) Int. Cl.
*G06F 19/00* (2018.01)
*A61B 19/00* (2006.01)
(Continued)

(52) U.S. Cl.
CPC ...... *A61B 19/5244* (2013.01); *A61B 1/00006* (2013.01); *A61B 1/00149* (2013.01);
(Continued)

(58) Field of Classification Search
CPC ............ A61B 19/5244; A61B 1/00006; A61B 1/3132; A61B 2019/2211; A61B 19/2203
(Continued)

(56) References Cited

U.S. PATENT DOCUMENTS 5,494,034 A * 2/1996 Schlondorff ........... A61B 6/501
378/20
6,179,776 B1 * 1/2001 Adams ............... A61B 1/00073
600/121
(Continued)

FOREIGN PATENT DOCUMENTS

WO WO/2013/027200 2/2013
WO WO/2013/027201 2/2013

OTHER PUBLICATIONS

International Search Report from PCT/IL2012/000310, dated May 21, 2013.
(Continued)

*Primary Examiner* — Khoi H Tran
*Assistant Examiner* — Jorge O Peche

(57) ABSTRACT

A surgical controlling system comprising: at least one location estimating means to real-time locate the 3D spatial position of at least one surgical tool, at least one movement detection means in communication with a movement database and with the location estimating means and a controller, which controls the position of at least one surgical tool, in communication with a movement database, a control database and the movement detection means. The movement database stores the 3D spatial position of each surgical tool at the present time and at at least one previous time; a tool has moved if its present position is different from its previous position. The control database stores rules to identify a movement of a tool as either an allowed movement or a restricted movement. Examples of rules include a maximum speed rule, a virtual zoom rule, a virtual rotation of scene rule, and position of tool rule.

64 Claims, 30 Drawing Sheets

Related U.S. Application Data is a continuation-in-part of application No. PCT/IL2012/000310, filed on Aug. 21, 2012.

(60) Provisional application No. 61/525,779, filed on Aug. 21, 2011, provisional application No. 61/525,787, filed on Aug. 21, 2011, provisional application No. 61/525,789, filed on Aug. 21, 2011, provisional application No. 61/750,856, filed on Jan. 10, 2013.

(51) Int. Cl.
*A61B 1/00* (2006.01)
*A61B 1/313* (2006.01)
*A61B 34/20* (2016.01)
*A61B 90/50* (2016.01)
*A61B 17/00* (2006.01)
*A61B 90/00* (2016.01)
*A61B 34/00* (2016.01)
*A61B 34/30* (2016.01)

(52) U.S. Cl.
CPC ............ *A61B 1/3132* (2013.01); *A61B 34/20* (2016.02); *A61B 90/50* (2016.02); *A61B 34/30* (2016.02); *A61B 2017/00119* (2013.01); *A61B 2017/00207* (2013.01); *A61B 2017/00216* (2013.01); *A61B 2017/00221* (2013.01); *A61B 2034/2046* (2016.02); *A61B 2034/2048* (2016.02); *A61B 2034/256* (2016.02); *A61B 2090/0807* (2016.02); *A61B 2090/0811* (2016.02); *A61B 2090/365* (2016.02); *A61B 2090/368* (2016.02)

(58) Field of Classification Search
USPC ....... 700/245, 259, 260; 901/1, 8, 41, 46, 47
See application file for complete search history.

(56) References Cited

U.S. PATENT DOCUMENTS

| | | | |
|---|---|---|---|
| 6,714,841 B1 | 3/2004 | Wright et al. | |
| 6,837,883 B2* | 1/2005 | Moll | A61B 19/2203 606/1 |
| 7,087,049 B2* | 8/2006 | Nowlin | A61B 34/70 606/1 |
| 8,079,950 B2* | 12/2011 | Stern | A61B 1/00188 600/109 |
| 8,758,263 B1* | 6/2014 | Rahimian | A61B 10/0233 600/562 |
| 8,992,542 B2* | 3/2015 | Hagag | A61B 34/20 606/130 |
| 2002/0091301 A1* | 7/2002 | Levin | A61B 17/00234 600/37 |
| 2003/0216833 A1* | 11/2003 | Mukai | B25J 9/1602 700/245 |
| 2004/0089777 A1* | 5/2004 | Schilt | A61B 90/50 248/227.2 |
| 2004/0111183 A1* | 6/2004 | Sutherland | A61B 90/25 700/245 |
| 2005/0219552 A1* | 10/2005 | Ackerman | A61B 1/042 356/603 |
| 2007/0005045 A1* | 1/2007 | Mintz | B25J 9/0084 606/1 |
| 2007/0013336 A1* | 1/2007 | Nowlin | B25J 9/1682 318/568.21 |
| 2007/0021713 A1* | 1/2007 | Kumar | A61M 1/006 604/27 |
| 2007/0021752 A1* | 1/2007 | Rogers | A61B 17/162 606/80 |
| 2008/0004603 A1 | 1/2008 | Larkins et al. | |
| 2008/0154389 A1* | 6/2008 | Smith | A61B 5/06 700/24 |
| 2008/0215181 A1* | 9/2008 | Smith | A61B 5/06 700/245 |
| 2008/0234866 A1* | 9/2008 | Kishi | B25J 9/1689 700/259 |
| 2008/0262297 A1 | 10/2008 | Gilboa et al. | |
| 2008/0275452 A1* | 11/2008 | Lang | A61B 17/15 606/88 |
| 2008/0300453 A1* | 12/2008 | Aoki | A61B 1/00156 600/103 |
| 2009/0043310 A1* | 2/2009 | Rasmussen | A61B 17/025 606/88 |
| 2009/0088774 A1* | 4/2009 | Swarup | A61B 34/37 606/130 |
| 2009/0099520 A1* | 4/2009 | Millman | A61M 1/0058 604/131 |
| 2009/0216114 A1* | 8/2009 | Gorges | A61B 90/36 600/425 |
| 2009/0240259 A1* | 9/2009 | Nelson | A61B 34/30 606/130 |
| 2009/0248037 A1* | 10/2009 | Prisco | A61B 34/71 606/130 |
| 2010/0022871 A1* | 1/2010 | De Beni | A61B 8/0833 600/424 |
| 2010/0036198 A1* | 2/2010 | Tacchino | A61B 1/0014 600/106 |
| 2010/0234857 A1* | 9/2010 | Itkowitz | G09B 23/285 606/130 |
| 2011/0177469 A1* | 7/2011 | Suter | A61C 8/0089 433/75 |
| 2012/0041263 A1 | 2/2012 | Sholev | |
| 2012/0071893 A1* | 3/2012 | Smith | A61B 17/1664 606/130 |
| 2012/0245415 A1* | 9/2012 | Emura | A61B 1/0005 600/109 |
| 2013/0123804 A1 | 5/2013 | Sholev et al. | |
| 2014/0163359 A1 | 6/2014 | Sholev et al. | |
| 2014/0194896 A1 | 7/2014 | Frimer et al. | |
| 2014/0221738 A1 | 8/2014 | Sholev et al. | |
| 2014/0228632 A1 | 8/2014 | Sholev et al. | |
| 2014/0378763 A1 | 12/2014 | Atarot et al. | |
| 2015/0025549 A1* | 1/2015 | Kilroy | A61B 19/2203 606/130 |
| 2015/0031953 A1 | 1/2015 | Atarot et al. | |

OTHER PUBLICATIONS

Extended European Search Report from EP2014015054, dated Aug. 22, 2014.
Written Opinion of PCT/IL2012/000310, dated Feb. 21, 2014.
International Preliminary Report of PCT/IL2012/000310, dated Feb. 25, 2014.

\* cited by examiner

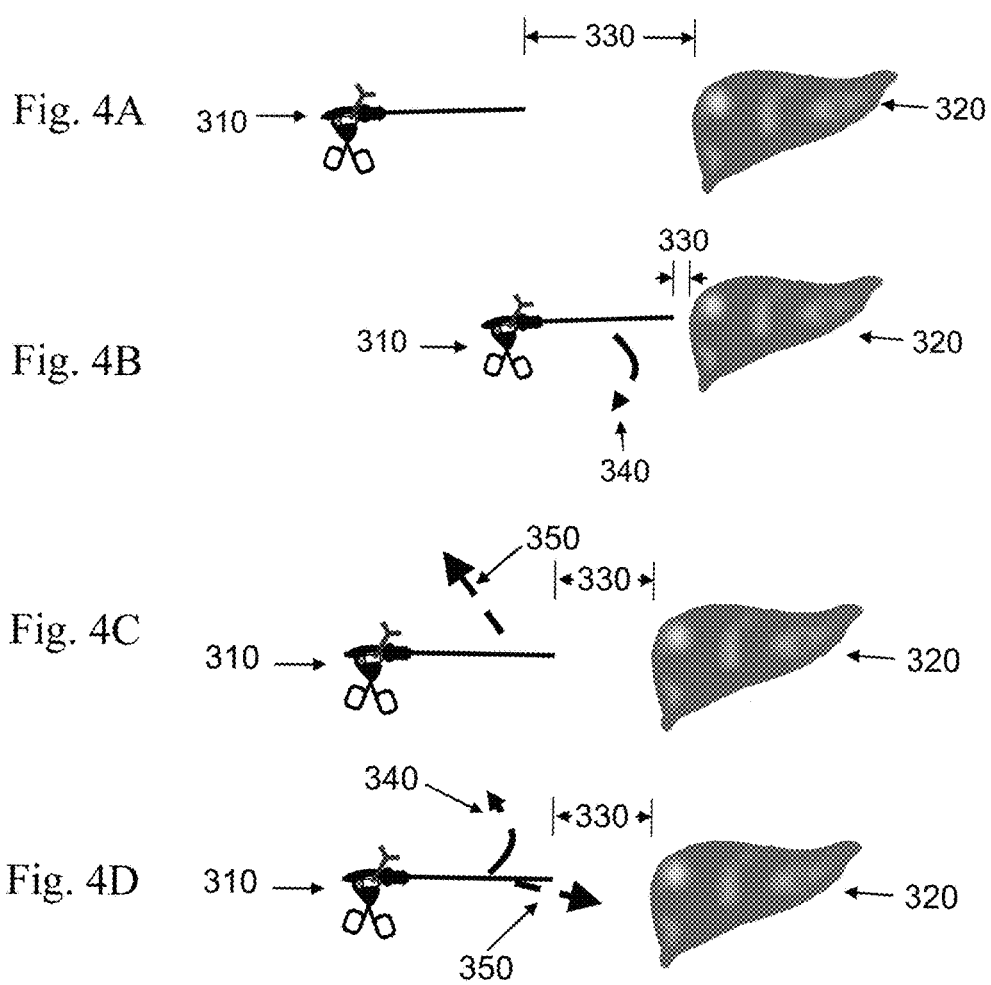

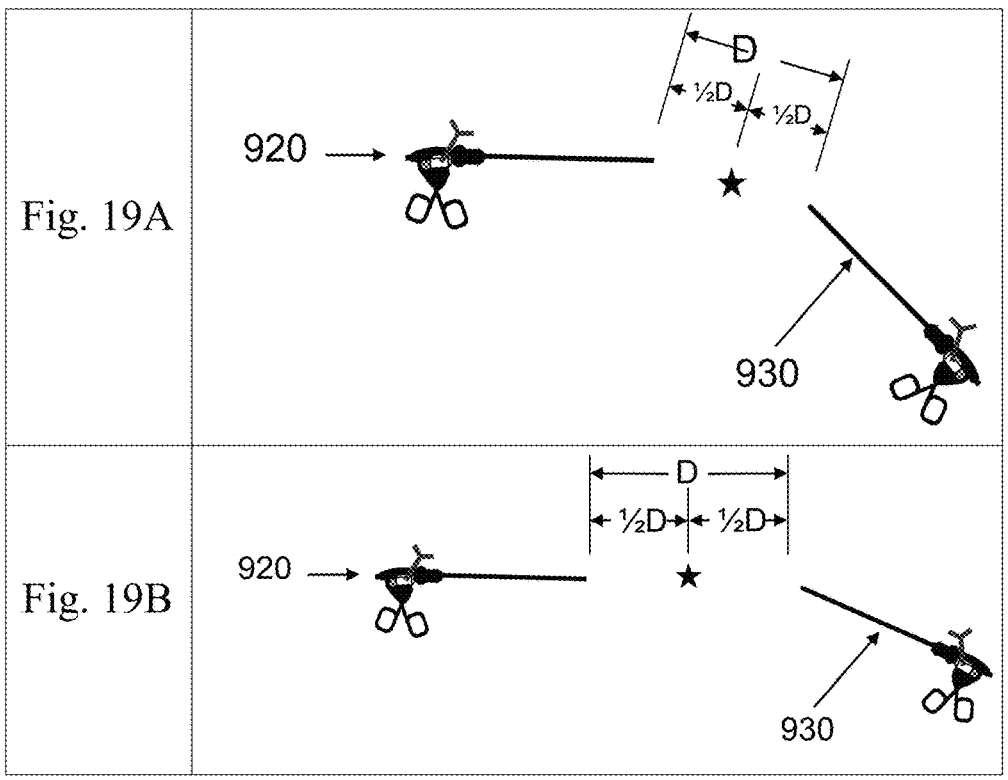

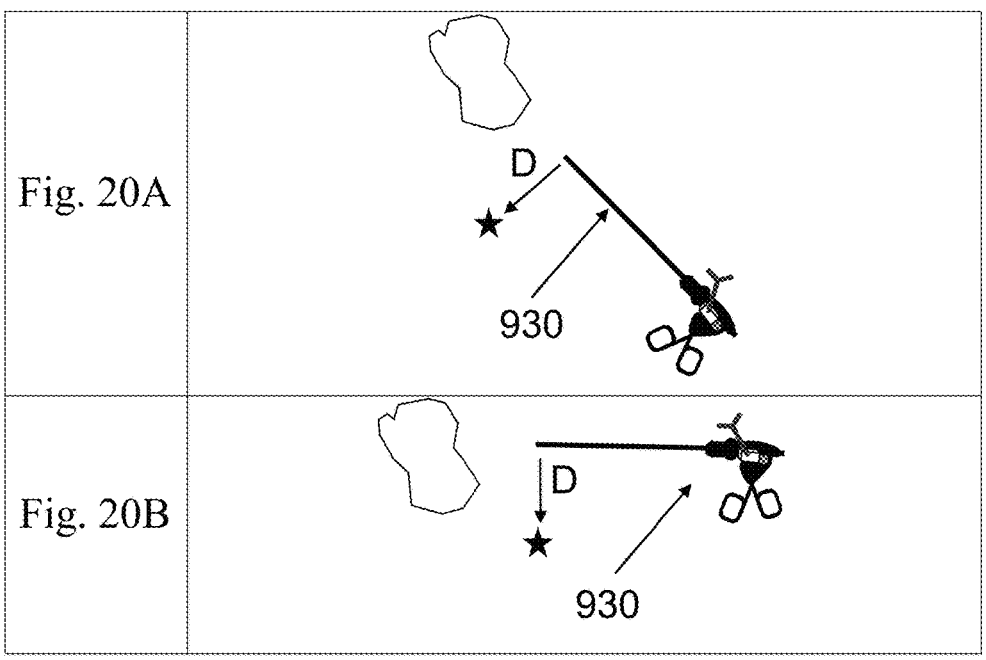

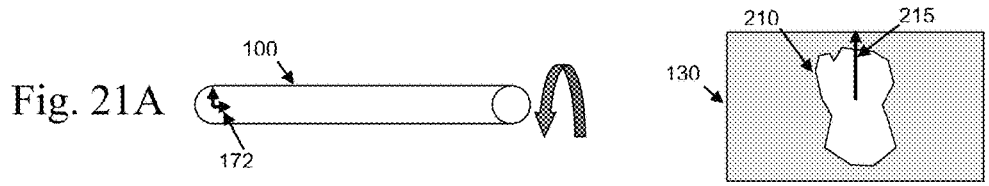
Fig. 21A
Fig. 21B
Fig. 21C
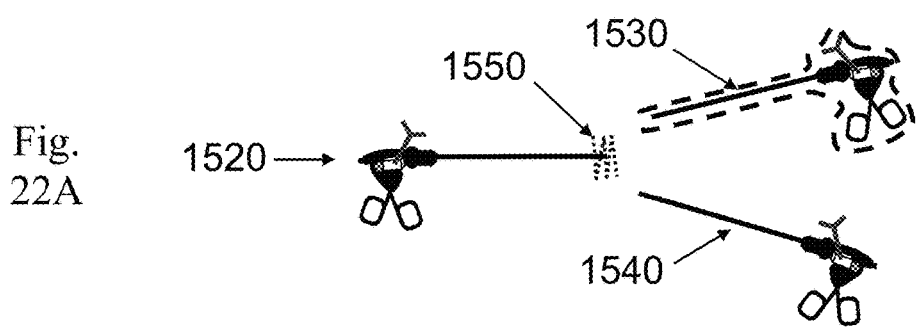
Fig. 22A

DEVICE AND METHOD FOR ASSISTING LAPAROSCOPIC SURGERY—RULE BASED APPROACH

CROSS REFERENCE TO RELATED APPLICATIONS

This application is a Continuation in Part of U.S. patent application Ser. No. 14/150,939, filed 9 Jan. 2014 (U.S. Pat. No. 9,204,939, granted 8 Dec. 2015), which claims priority from U.S. Provisional Application No. 61/750,856, filed 10 Jan. 2013, and is a Continuation-in-part Application of International (PCT) Application No. PCT/IL2012/000310, filed 21 Aug. 2012, which claims priority from U.S. Provisional Patent Application No. 61/525,787, filed 21 Aug. 2011, U.S. Provisional Patent Application No. 61/525,779, filed 21 Aug. 2011, and U.S. Provisional Patent Application No. 61/525,789, filed 21 Aug. 2011. All of these applications are hereby incorporated by reference in their entirety.

FIELD OF THE INVENTION

The present invention generally relates to means and methods for improving the interface between the surgeon and the operating medical assistant or between the surgeon and an endoscope system for laparoscopic surgery. Moreover, the present invention discloses a device useful for spatially repositioning an endoscope to a specific region in the human body during surgery.

BACKGROUND OF THE INVENTION

In laparoscopic surgery, the surgeon performs the operation through small holes using long instruments and observing the internal anatomy with an endoscope camera. The endoscope is conventionally held by a human camera assistant (i.e. operating medical assistant) since the surgeon must perform the operation using both hands. The surgeon's performance is largely dependent on the camera position relative to the instruments and on a stable image shown by the monitor. The main problem is that it is difficult for the operating medical assistant to hold the endoscope steady, keeping the scene upright.

Laparoscopic surgery is becoming increasingly popular with patients because the scars are smaller and their period of recovery is shorter. Laparoscopic surgery requires special training for the surgeon or gynecologist and the theatre nursing staff. The equipment is often expensive and is not available in all hospitals.

During laparoscopic surgery, it is often required to shift the spatial placement of the endoscope in order to present the surgeon with an optimal view. Conventional laparoscopic surgery makes use of either human assistants that manually shift the instrumentation or, alternatively, robotic automated assistants. Automated assistants utilize interfaces that enable the surgeon to direct the mechanical movement of the assistant, achieving a shift in the camera view.

U.S. Pat. No. 6,714,841 discloses an automated camera endoscope in which the surgeon is fitted with a head mounted light source that transmits the head movements to a sensor, forming an interface that converts the movements to directions for the mechanical movement of the automated assistant. Alternative automated assistants incorporate a voice operated interface, a directional key interface, or other navigational interfaces. The above interfaces share the following drawbacks:

a. A single directional interface that provide limited feedback to the surgeon.
b. A cumbersome serial operation for starting and stopping movement directions that requires the surgeon's constant attention, preventing the surgeon from keeping the flow of the surgical procedure.

Research has suggested that these systems divert the surgeon's focus from the major task at hand. Therefore, technologies assisted by magnets and image processing have been developed to simplify interfacing control. However, these improved technologies still fail to address another complicating interface aspect of laparoscopic surgery, in that they do not allow the surgeon to signal, to automated assistants or to human assistants or to surgical colleagues, which instrument his attention is focused on.

Hence, there is still a long felt need for a improving the interface between the surgeon and an endoscope system, surgical colleagues or human assistants for laparoscopic surgery.

SUMMARY OF THE INVENTION

It is one object of the present invention to provide a surgical controlling system, comprising:
 a. at least one surgical tool configured to be inserted into a surgical environment of a human body for assisting a surgical procedure;
 b. at least one location estimating means configured to real rime locate the 3D spatial position of the at least one surgical tool at any given time t;
 c. at least one movement detection means communicable with a movement's database and with said location estimating means; said movement's database is configured to store said 3D spatial position of said at least one surgical tool at time $t_f$ and at time $t_0$; where $t_f>t_0$; said movement detection means is configured to detect movement of said at least one surgical tool if the 3D spatial position of said at least one surgical tool at time $t_f$ is different than said 3D spatial position of said at least one surgical tool at time $t_0$; and,
 d. a controller having a processing means communicable with a controller's database, the controller configured to control the spatial position of the at least one surgical tool; said controller's database is in communication with said movement detection means;
 wherein the controller's database is configured to store a predetermined set of rules according to which allowed and restricted movements of the at least one surgical tool are determined, such that each detected movement by said movement detection means of said at least one surgical tool is determined as either an allowed movement or as a restricted movement according to said predetermined set of rules
 wherein said predetermined set of rules comprises at least one fixed point rule; said fixed point rule comprises a communicable database; said communicable database configured to receive at least one 3D position to be tracked; said fixed point rule is configured to determine said allowed and restricted movements according to said at least one 3D position to be tracked in said surgical environment, such that said allowed movements are movements in which said at least one surgical tool is located substantially in said at least one 3D position to be tracked, and said restricted movements are movements in which the location of said at least one surgical tool is substantially different from said 3D at least one 3D position to be tracked.

It is another object of the present invention to provide the surgical controlling system as defined above, wherein said at least one 3D position to be tracked is defined as a function of a predetermined position within said surgical environment; said predetermined position is selected from a group consisting of a tip of said at least one surgical tool, at least one position on at least one of said surgical tool; at least one position on at least one tissue; at least one tissue, at least one position on at least one organ; at least one organ, at least one 3D position within said surgical environment, and any combination thereof It is another object of the present invention to provide the surgical controlling system as defined above, wherein the predetermined set of rules further comprises at least one rule selected from a group consisting of: most used tool rule, right tool rule, left tool rule, field of view rule, no fly zone rule, route rule, environmental rule, operator input rule, proximity rule; collision prevention rule, history-based rule, tool-dependent allowed and restricted movements rule, preferred volume zone rule, preferred tool rule, a movement detection rule, tagged tool rule, change of speed rule and any combination thereof.

It is another object of the present invention to provide the surgical controlling system as defined above, wherein the route rule comprises a communicable database storing predefined route in which the at least one surgical tool is configured to move within the surgical environment; the predefined route comprises n 3D spatial positions of the at least one surgical tool; n is an integer greater than or equals to 2; the allowed movements are movements in which the at least one surgical tool is located substantially in at least one of the n 3D spatial positions of the predefined route, and the restricted movements are movements in which the location of the at least one surgical tool is substantially different from the n 3D spatial positions of the predefined route.

It is another object of the present invention to provide the surgical controlling system as defined above, wherein the environmental rule comprises a comprises a communicable database; the communicable database is configured to received real-time image of the surgical environment and is configured to perform real-time image processing of the same and to determine the 3D spatial position of hazards or obstacles in the surgical environment; the environmental rule is configured to determine the allowed and restricted movements according to the hazards or obstacles in the surgical environment, such that the restricted movements are movements in which the at least one surgical tool is located substantially in at least one of the 3D spatial positions, and the allowed movements are movements in which the location of the at least one surgical tool is substantially different from the 3D spatial positions.

It is another object of the present invention to provide the surgical controlling system as defined above, wherein the hazards or obstacles in the surgical environment are selected from a group consisting of tissue, a surgical tool, an organ, an endoscope and any combination thereof.

It is another object of the present invention to provide the surgical controlling system as defined above, wherein the operator input rule comprises a communicable database; the communicable database is configured to receive an input from the operator of the system regarding the allowed and restricted movements of the at least one surgical tool.

It is another object of the present invention to provide the surgical controlling system as defined above, wherein the input comprises n 3D spatial positions; n is an integer greater than or equals to 2; wherein at least one of which is defined as allowed location and at least one of which is defined as restricted location, such that the allowed movements are movements in which the at least one surgical tool is located substantially in at least one of the n 3D spatial positions, and the restricted movements are movements in which the location of the at least one surgical tool is substantially different from the n 3D spatial positions.

It is another object of the present invention to provide the surgical controlling system as defined above, wherein the input comprises at least one rule according to which allowed and restricted movements of the at least one surgical tool are determined, such that the spatial position of the at least one surgical tool is controlled by the controller according to the allowed and restricted movements.

It is another object of the present invention to provide the surgical controlling system as defined above, wherein the predetermined set of rules comprises at least one rule selected from the group consisting of: most used tool, right tool rule, left tool rule, field of view rule, no fly zone rule, a route rule, an environmental rule, an operator input rule, a proximity rule; a collision prevention rule, preferred volume zone rule, movement detection rule, a history based rule, a tool-dependent allowed and restricted movements rule, and any combination thereof.

It is another object of the present invention to provide the surgical controlling system as defined above, wherein the operator input rule converts an allowed movement to a restricted movement and a restricted movement to an allowed movement.

It is another object of the present invention to provide the surgical controlling system as defined above, wherein the proximity rule is configured to define a predetermined distance between at least two surgical tools; the allowed movements are movements which are within the range or out of the range of the predetermined distance, and the restricted movements which are out of the range or within the range of the predetermined distance.

It is another object of the present invention to provide the surgical controlling system as defined above, wherein the proximity rule is configured to define a predetermined angle between at least three surgical tools; the allowed movements are movements which are within the range or out of the range of the predetermined angle, and the restricted movements which are out of the range or within the range of the predetermined angle.

It is another object of the present invention to provide the surgical controlling system as defined above, wherein the collision prevention rule is configured to define a predetermined distance between the at least one surgical tool and an anatomical element within the surgical environment; the allowed movements are movements which are in a range that is larger than the predetermined distance, and the restricted movements are movements which is in a range that is smaller than the predetermined distance.

It is another object of the present invention to provide the surgical controlling system as defined above, wherein the anatomical element is selected from a group consisting of tissue, organ, another surgical tool or any combination thereof.

It is another object of the present invention to provide the surgical controlling system as defined above, wherein at least one of the following is being held true (a) said system additionally comprising an endoscope; said endoscope is configured to provide real-time image of said surgical environment; (b) at least one of said surgical tools is an endoscope configured to provide real-time image of said surgical environment.

It is another object of the present invention to provide the surgical controlling system as defined above, wherein the right tool rule is configured to determine the allowed movement of the endoscope according to the movement of the surgical tool positioned to right of the endoscope.

It is another object of the present invention to provide the surgical controlling system as defined above, wherein the left tool rule is configured to determine the allowed movement of the endoscope according to the movement of the surgical tool positioned to left of the endoscope.

It is another object of the present invention to provide the surgical controlling system as defined above, said a tagged tool rule comprises means configured to tag at least one surgical tool within said surgical environment and to determine said allowed movement of said endoscope according to the movement of said tagged surgical tool.

It is another object of the present invention to provide the surgical controlling system as defined above, wherein the field of view rule comprises a communicable database comprising n 3D spatial positions; n is an integer greater than or equals to 2; the combination of all of the n 3D spatial positions provides a predetermined field of view; the field of view rule is configured to determine the allowed movement of the endoscope within the n 3D spatial positions so as to maintain a constant field of view, such that the allowed movements are movements in which the endoscope is located substantially in at least one of the n 3D spatial positions, and the restricted movements are movements in which the location of the endoscope is substantially different from the n 3D spatial positions.

It is another object of the present invention to provide the surgical controlling system as defined above, wherein the preferred volume zone rule comprises a communicable database comprising n 3D spatial positions; n is an integer greater than or equals to 2; the n 3D spatial positions provides the preferred volume zone; the preferred volume zone rule is configured to determine the allowed movement of the endoscope within the n 3D spatial positions and restricted movement of the endoscope outside the n 3D spatial positions, such that the allowed movements are movements in which the endoscope is located substantially in at least one of the n 3D spatial positions, and the restricted movements are movements in which the location of the endoscope is substantially different from the n 3D spatial positions.

It is another object of the present invention to provide the surgical controlling system as defined above, wherein the preferred tool rule comprises a communicable database, the database stores a preferred tool; the preferred tool rule is configured to determine the allowed movement of the endoscope according to the movement of the preferred tool.

It is another object of the present invention to provide the surgical controlling system as defined above, wherein the no fly zone rule comprises a communicable database comprising n 3D spatial positions; n is an integer greater than or equals to 2; the n 3D spatial positions define a predetermined volume within the surgical environment; the no fly zone rule is configured to determine the restricted movement if the movement is within the no fly zone and the allowed movement if the movement is outside the no fly zone, such that the restricted movements are movements in which the at least one of the surgical tool is located substantially in at least one of the n 3D spatial positions, and the allowed movements are movements in which the location of the at least one surgical tool is substantially different from the n 3D spatial positions.

It is another object of the present invention to provide the surgical controlling system as defined above, wherein the most used tool rule comprises a communicable database counting the amount of movement of each of the surgical tools; the most used tool rule is configured to constantly position the endoscope to track the movement of the most moved surgical tool.

It is another object of the present invention to provide the surgical controlling system as defined above, wherein said system further comprising a maneuvering subsystem communicable with said controller, said maneuvering subsystem is configured to spatially reposition said at least one surgical tool during a surgery according to said predetermined set of rules; further wherein the system is configured to alert the physician of a restricted movements of the at least one surgical tool.

It is another object of the present invention to provide the surgical controlling system as defined above, wherein the alert is selected from a group consisting of audio signaling, voice signaling, light signaling, flashing signaling and any combination thereof.

It is another object of the present invention to provide the surgical controlling system as defined above, wherein the allowed movement is permitted by the controller and a restricted movement is denied by the controller.

It is another object of the present invention to provide the surgical controlling system as defined above, wherein the history based rule comprises a communicable database storing each 3D spatial position of each of the surgical tool, such that each movement of each surgical tool is stored; the history based rule is configured to determine the allowed and restricted movements according to historical movements of the at least one surgical tool, such that the allowed movements are movements in which the at least one surgical tool is located substantially in at least one of the 3D spatial positions, and the restricted movements are movements in which the location of the at least one surgical tool is substantially different from the n 3D spatial positions.

It is another object of the present invention to provide the surgical controlling system as defined above, wherein the tool-dependent allowed and restricted movements rule comprises a communicable database; the communicable database is configured to store predetermined characteristics of at least one of the surgical tool; the tool-dependent allowed and restricted movements rule is configured to determine the allowed and restricted movements according to the predetermined characteristics of the surgical tool.

It is another object of the present invention to provide the surgical controlling system as defined above, wherein the predetermined characteristics of the surgical tool are selected from the group consisting of: physical dimensions, structure, weight, sharpness, and any combination thereof.

It is another object of the present invention to provide the surgical controlling system as defined above, wherein the movement detection rule comprises a communicable database comprising the real-time 3D spatial positions of each of the surgical tool; and to detect movement of the at least one surgical tool when a change in the 3D spatial positions is received, such that the allowed movements are movements in which the endoscope is directed to focus on the moving surgical tool.

It is another object of the present invention to provide the surgical controlling system as defined above, further comprising a maneuvering subsystem communicable with the controller, the maneuvering subsystem is configured to spatially reposition the at least one surgical tool during a surgery according to the predetermined set of rules, such that if said movement of said at least one surgical tool is a restricted movement, said maneuvering subsystem prevents said movement.

It is another object of the present invention to provide the surgical controlling system as defined above, wherein the at least one location estimating means comprises at least one endoscope configured to acquire real-time images of the surgical environment within the human; and at least one surgical instrument spatial location software configured to receive said real-time images of said surgical environment and to estimate said 3D spatial position of said at least one surgical tool.

It is another object of the present invention to provide the surgical controlling system as defined above, wherein the at least one location estimating means are comprises (a) at least one element selected from a group consisting of optical imaging means, radio frequency transmitting and receiving means, at least one mark on the at least one surgical tool and any combination thereof; and, (b) at least one surgical instrument spatial location software configured to estimate said 3D spatial position of said at least one surgical tool by means of said element.

It is another object of the present invention to provide the surgical controlling system as defined above, wherein the at least one location estimating means are an interface subsystem between a surgeon and the at least one surgical tool, the interface subsystem comprises:
 a. at least one array comprising N regular or pattern light sources, where N is a positive integer;
 b. at least one array comprising M cameras, each of the M cameras, where M is a positive integer;
 c. optional optical markers and means for attaching the optical marker to the at least one surgical tool; and;
 d. a computerized algorithm operable via the controller, the computerized algorithm configured to record images received by each camera of each of the M cameras and to calculate therefrom the position of each of the tools, and further configured to provide automatically the results of the calculation to the human operator of the interface.

It is another object of the present invention to provide a method for assisting an operator to perform a surgical procedure, comprising steps of:
 a. providing a surgical controlling system, comprising: (i) at least one surgical tool; (ii) at least one location estimating means; (iii) at least one movement detection means; and, (iv) a controller having a processing means communicable with a controller's database;
 b. inserting the at least one surgical tool into a surgical environment of a human body;
 c. real-time estimating the location of the at least one surgical tool within the surgical environment at any given time t; and,
 d. detecting if there is movement of said at least one surgical tool if the 3D spatial position of said at least one surgical tool at time $t_f$ is different than said 3D spatial position of said at least one surgical tool at time $t_o$;
 e. controlling the spatial position of the at least one surgical tool within the surgical environment by means of the controller;
 wherein the step of controlling is performed by storing a predetermined set of rules in a controller's database; said predetermined set of rules comprises allowed and restricted movements of the at least one surgical tool, such that each detected movement by said movement detection means of said at least one surgical tool is determined as either an allowed movement or as a restricted movement according to said predetermined set of rules;
 wherein said predetermined set of rules comprises at least one fixed point rule; said fixed point rule comprises a communicable database; said communicable database configured to receive at least one 3D position to be tracked; said fixed point rule is configured to determine said allowed and restricted movements according to said at least one 3D position to be tracked in said surgical environment, such that said allowed movements are movements in which said at least one surgical tool is located substantially in said at least one 3D position to be tracked, and said restricted movements are movements in which the location of said at least one surgical tool is substantially different from said 3D at least one 3D position to be tracked.

It is another object of the present invention to provide the method as defined above, wherein said at least one 3D position to be tracked is defined as a function of a predetermined position within said surgical environment; said predetermined position is selected from a group consisting of a tip of said at least one surgical tool, at least one position on at least one of said surgical tool; at least one position on at least one tissue; at least one tissue, at least one position on at least one organ; at least one organ, at least one 3D position within said surgical environment, and any combination thereof It is another object of the present invention to provide the method as defined above, further comprising a step of selecting the predetermined set of rules from the group consisting of: most used tool, right tool rule, left tool rule, field of view rule, no fly zone rule, a route rule, an environmental rule, an operator input rule, a proximity rule; a collision prevention rule, preferred volume zone rule, preferred tool rule, movement detection rule, a history based rule, a tool-dependent allowed and restricted movements rule, tagged tool rule and any combination thereof.

It is another object of the present invention to provide the method as defined above, wherein the route rule comprises a communicable database storing predefined route in which the at least one surgical tool is configured to move within the surgical environment; the predefined route comprises n 3D spatial positions of the at least one surgical tool; n is an integer greater than or equals to 2; the allowed movements are movements in which the at least one surgical tool is located substantially in at least one of the n 3D spatial positions of the predefined route, and the restricted movements are movements in which the location of the at least one surgical tool is substantially different from the n 3D spatial positions of the predefined route.

It is another object of the present invention to provide the method as defined above, wherein the environmental rule comprises a comprises a communicable database; the communicable database is configured to received real-time image of the surgical environment and is configured to perform real-time image processing of the same and to determine the 3D spatial position of hazards or obstacles in the surgical environment; the environmental rule is configured to determine the allowed and restricted movements according to the hazards or obstacles in the surgical environment, such that the restricted movements are movements in which the at least one surgical tool is located substantially in at least one of the 3D spatial positions, and the allowed movements are movements in which the location of the at least one surgical tool is substantially different from the 3D spatial positions.

It is another object of the present invention to provide the method as defined above, wherein the hazards or obstacles in the surgical environment are selected from a group consisting of tissue, a surgical tool, an organ, an endoscope and any combination thereof It is another object of the present invention to provide the method as defined above, wherein the operator input rule comprises a communicable database; the communicable database is configured to receive an input from the operator of the system regarding the allowed and restricted movements of the at least one surgical tool.

It is another object of the present invention to provide the method as defined above, wherein the input comprises n 3D spatial positions; n is an integer greater than or equals to 2; wherein at least one of which is defined as allowed location and at least one of which is defined as restricted location, such that the allowed movements are movements in which the at least one surgical tool is located substantially in at least one of the n 3D spatial positions, and the restricted movements are movements in which the location of the at least one surgical tool is substantially different from the n 3D spatial positions.

It is another object of the present invention to provide the method as defined above, wherein the input comprises at least one predetermined rule according to which allowed and restricted movements of the at least one surgical tool are determined, such that the spatial position of the at least one surgical tool is controlled by the controller according to the allowed and restricted movements.

It is another object of the present invention to provide the method as defined above, wherein the predetermined rules is selected from the group consisting of: most used tool, right tool rule, left tool rule, field of view rule, no fly zone rule, preferred volume zone rule, a route rule, an environmental rule, an operator input rule, a proximity rule; a collision prevention rule, a history based rule, a tool-dependent allowed and restricted movements rule, and any combination thereof It is another object of the present invention to provide the method as defined above, wherein the operator input rule converts an allowed movement to a restricted movement and a restricted movement to an allowed movement.

It is another object of the present invention to provide the method as defined above, wherein the proximity rule is configured to define a predetermined distance between at least two surgical tools; the allowed movements are movements which are within the range or out of the range of the predetermined distance, and the restricted movements which are out of the range or within the range of the predetermined distance.

It is another object of the present invention to provide the method as defined above, wherein the proximity rule is configured to define a predetermined angle between at least three surgical tools; the allowed movements are movements which are within the range or out of the range of the predetermined angle, and the restricted movements which are out of the range or within the range of the predetermined angle It is another object of the present invention to provide the method as defined above, wherein the collision prevention rule is configured to define a predetermined distance between the at least one surgical tool and an anatomical element within the surgical environment; the allowed movements are movements which are in a range that is larger than the predetermined distance, and the restricted movements are movements which is in a range that is smaller than the predetermined distance.

It is another object of the present invention to provide the method as defined above, wherein the anatomical element is selected from a group consisting of tissue, organ, another surgical tool or any combination thereof.

It is another object of the present invention to provide the method as defined above, wherein at least one of the following is being held true (a) said system additionally comprising an endoscope; said endoscope is configured to provide real-time image of said surgical environment; (b) at least one of said surgical tools is an endoscope configured to provide real-time image of said surgical environment.

It is another object of the present invention to provide the method as defined above, wherein the right tool rule is configured to determine the allowed movement of the endoscope according to the movement of the surgical tool positioned to right of the endoscope.

It is another object of the present invention to provide the method as defined above, wherein the left tool rule is configured to determine the allowed movement of the endoscope according to the movement of the surgical tool positioned to left of the endoscope.

It is another object of the present invention to provide the method as defined above, wherein said a tagged tool rule comprises means configured to tag at least one surgical tool within said surgical environment and to determine said allowed movement of said endoscope according to the movement of said tagged surgical tool.

It is another object of the present invention to provide the method as defined above, wherein the field of view rule comprises n 3D spatial positions; n is an integer greater than or equals to 2; the combination of all of the n 3D spatial positions provides a predetermined field of view; the field of view rule is configured to determine the allowed movement of the endoscope within the n 3D spatial positions so as to maintain a constant field of view, such that the allowed movements are movements in which the endoscope is located substantially in at least one of the n 3D spatial positions, and the restricted movements are movements in which the location of the endoscope is substantially different from the n 3D spatial positions.

It is another object of the present invention to provide the method as defined above, wherein the preferred volume zone rule comprises a communicable database comprising n 3D spatial positions; n is an integer greater than or equals to 2; the n 3D spatial positions provides the preferred volume zone; the preferred volume zone rule is configured to determine the allowed movement of the endoscope within the n 3D spatial positions and restricted movement of the endoscope outside the n 3D spatial positions, such that the allowed movements are movements in which the endoscope is located substantially in at least one of the n 3D spatial positions, and the restricted movements are movements in which the location of the endoscope is substantially different from the n 3D spatial positions.

It is another object of the present invention to provide the method as defined above, wherein the preferred tool rule comprises a communicable database, the database stores a preferred tool; the preferred tool rule is configured to determine the allowed movement of the endoscope according to the movement of the preferred tool.

It is another object of the present invention to provide the method as defined above, wherein the no fly zone rule comprises n 3D spatial positions; n is an integer greater than or equals to 2; the n 3D spatial positions define a predetermined volume within the surgical environment; the no fly zone rule is configured to determine the restricted movement if the movement is within the no fly zone and the allowed movement if the movement is outside the no fly zone, such that the restricted movements are movements in which the at least one of the surgical tool is located substantially in at least one of the n 3D spatial positions, and the allowed movements are movements in which the location of the at least one surgical tool is substantially different from the n 3D spatial positions.

It is another object of the present invention to provide the method as defined above, wherein the most used tool rule comprises a database counting the amount of movement of each of the surgical tools; the most used tool rule is configured to constantly position the endoscope to track the movement of the most moved surgical tool.

It is another object of the present invention to provide the method as defined above, additionally comprising step of alerting the physician of a restricted movements of the at least one surgical tool.

It is another object of the present invention to provide the method as defined above, wherein the step of alerting is performed by at least one selected from a group consisting of audio signaling, voice signaling, light signaling, flashing signaling and any combination thereof.

It is another object of the present invention to provide the method as defined above, wherein the allowed movement is permitted by the controller and a restricted movement is denied by the controller.

It is another object of the present invention to provide the method as defined above, wherein the history based rule comprises a communicable database storing each 3D spatial position of each of the surgical tool, such that each movement of each surgical tool is stored; the history based rule is configured to determine the allowed and restricted movements according to historical movements of the at least one surgical tool, such that the allowed movements are movements in which the at least one surgical tool is located substantially in at least one of the 3D spatial positions, and the restricted movements are movements in which the location of the at least one surgical tool is substantially different from the n 3D spatial positions.

It is another object of the present invention to provide the method as defined above, wherein the tool-dependent allowed and restricted movements rule comprises a communicable database; the communicable database is configured to store predetermined characteristics of at least one of the surgical tool; the tool-dependent allowed and restricted movements rule is configured to determine the allowed and restricted movements according to the predetermined characteristics of the surgical tool.

It is another object of the present invention to provide the method as defined above, wherein the predetermined characteristics of the surgical tool are selected from the group consisting of: physical dimensions, structure, weight, sharpness, and any combination thereof.

It is another object of the present invention to provide the method as defined above, wherein the movement detection rule comprises a communicable database comprising the real-time 3D spatial positions of each of the surgical tool; and to detect movement of the at least one surgical tool when a change in the 3D spatial positions is received, such that the allowed movements are movements in which the endoscope is directed to focus on the moving surgical tool.

It is another object of the present invention to provide the method as defined above, further comprising a step of providing a maneuvering subsystem communicable with the controller, the maneuvering subsystem is configured to spatially reposition the at least one surgical tool during a surgery according to the predetermined set of rules.

It is another object of the present invention to provide the method as defined above, wherein the at least one location estimating means comprises at least one endoscope configured to acquire real-time images of a surgical environment within the human body; and at least one surgical instrument spatial location software configured to receive said real-time images of said surgical environment and to estimate said 3D spatial position of said at least one surgical tool.

It is another object of the present invention to provide the method as defined above, wherein the at least one location estimating means are comprises (a) at least one element selected from a group consisting of optical imaging means, radio frequency transmitting and receiving means, at least one mark on the at least one surgical tool and any combination thereof; and, (b) at least one surgical instrument spatial location software configured to estimate said 3D spatial position of said at least one surgical tool by means of said element.

It is another object of the present invention to provide the method as defined above, wherein the at least one location estimating means are an interface subsystem between a surgeon and the at least one surgical tool, the interface subsystem comprises:
  a. at least one array comprising N regular or pattern light sources, where N is a positive integer;
  b. at least one array comprising M cameras, each of the M cameras, where M is a positive integer;
  c. optional optical markers and means for attaching the optical marker to the at least one surgical tool; and,
  d. a computerized algorithm operable via the controller, the computerized algorithm configured to record images received by each camera of each of the M cameras and to calculate therefrom the position of each of the tools, and further configured to provide automatically the results of the calculation to the human operator of the interface.

It is another object of the present invention to provide a surgical tracking system for assisting an operator to perform a laparoscopic surgery of a human body, the surgical tracking system comprising:
  a. at least one endoscope configured to acquire real-time images of a surgical environment within the human body;
  b. a maneuvering subsystem configured to control the spatial position of the endoscope during the laparoscopic surgery; and,
  c. a tracking subsystem in communication with the maneuvering subsystem, configured to control the maneuvering system so as to direct and modify the spatial position of the endoscope to a region of interest;
  wherein the tracking subsystem comprises a data processor; the data processor is configured to perform real-time image processing of the surgical environment and to instruct the maneuvering subsystem to modify the spatial position of the endoscope according to input received from a maneuvering function f(t); the maneuvering function f(t) is configured to (a) receive input from at least two instructing functions $g_i(t)$, where i is 1, . . . , n and n≥2; where t is time; i and n are integers; and, to (b) output instructions to the maneuvering subsystem based on the input from the at least two instructing functions $g_i(t)$, so as to spatially position the endoscope to the region of interest.

It is another object of the present invention to provide the surgical tracking system as defined above, wherein each of the instructing functions $g_i(t)$ is provided with $\alpha_i(t)$ where i is an integer greater than or equals to 1; where $\alpha_i(t)$ are weighting functions of each $g_i(t)$, and a n is total number of instruction functions.

It is another object of the present invention to provide the surgical tracking system as defined above, wherein each of the instructing functions $g_i(t)$ is selected from a group consisting of: most used tool function, a right tool function, left tool function, field of view function, preferred volume zone function, preferred tool function, no fly zone function, a tool detection function, a movement detection function, an organ detection function, a collision detection function, an operator input function, a prediction function, a past statistical analysis function, proximity function, a tagged tool function, and any combination thereof.

It is another object of the present invention to provide the surgical tracking system as defined above, wherein the weighting functions $\alpha_i(t)$ are time-varying functions, wherein the value of which is determined by the operators.

It is another object of the present invention to provide the surgical tracking system as defined above, wherein the tool detection function is configured to detect surgical tools in the surgical environment and to output instruction to the tracking subsystem to instruct the maneuvering system to direct the endo scope on the detected surgical tools.

It is another object of the present invention to provide the surgical tracking system as defined above, wherein the movement detection function comprises a communicable database comprising the real-time 3D spatial positions of each of the surgical tool in the surgical environment; and to detect movement of the at least one surgical tool when a change in the 3D spatial positions is received, and to output instructions to the tracking subsystem to instruct the maneuvering system to direct the endoscope on the moved surgical tool.

It is another object of the present invention to provide the surgical tracking system as defined above, wherein the organ detection function is configured to detect organs in the surgical environment and to output instructions to the tracking subsystem to instruct the maneuvering system to direct the endo scope on the detected organs.

It is another object of the present invention to provide the surgical tracking system as defined above, wherein the right tool function is configured to detect surgical tool positioned to right of the endoscope and to output instructions to the tracking subsystem to instruct the maneuvering system to constantly direct the endoscope on the right tool and to track the right tool.

It is another object of the present invention to provide the surgical tracking system as defined above, wherein the left tool function is configured to detect surgical tool positioned to left of the endoscope and to output instructions to the tracking subsystem to instruct the maneuvering system to constantly direct the endoscope on the left tool and to track the left tool.

It is another object of the present invention to provide the surgical tracking system as defined above, wherein the operator input function comprises a communicable database; the communicable database is configured to receive an input from the operator of the system; the input comprising n 3D spatial positions; n is an integer greater than or equals to 2; and to output instructions to the tracking subsystem to instruct the maneuvering system to direct the endoscope to the at least one 3D spatial position received.

It is another object of the present invention to provide the surgical tracking system as defined above, wherein the proximity function is configured to define a predetermined distance between at least two surgical tools; and to output instructions to the tracking subsystem to instruct the maneuvering system to direct the endoscope to the two surgical tools if the distance between the two surgical tools is less than the predetermined distance.

It is another object of the present invention to provide the surgical tracking system as defined above, wherein the proximity function is configured to define a predetermined angle between at least three surgical tools; and to output instructions to the tracking subsystem to instruct the maneuvering system to direct the endoscope to the three surgical tools if the angle between the two surgical tools is less than or greater than the predetermined angle.

It is another object of the present invention to provide the surgical tracking system as defined above, wherein the preferred volume zone function comprises communicable database comprising n 3D spatial positions; n is an integer greater than or equals to 2; the n 3D spatial positions provides the preferred volume zone; the preferred volume zone function is configured to output instructions to the tracking subsystem to instruct the maneuvering system to direct the endoscope to the preferred volume zone.

It is another object of the present invention to provide the surgical tracking system as defined above, wherein the preferred tool function comprises a communicable database, the database stores a preferred tool; the preferred tool function is configured to output instructions to the tracking subsystem to instruct the maneuvering system to direct the endoscope to the preferred tool.

It is another object of the present invention to provide the surgical tracking system as defined above, wherein the collision prevention function is configured to define a predetermined distance between the at least one surgical tool and an anatomical element within the surgical environment; and to output instructions to the tracking subsystem to instruct the maneuvering system to direct the endoscope to the surgical tool and the anatomical element within the surgical environment if the distance between the at least one surgical tool and an anatomical element is less than the predetermined distance.

It is another object of the present invention to provide the surgical tracking system as defined above, wherein the anatomical element is selected from a group consisting of tissue, organ, another surgical tool or any combination thereof.

It is another object of the present invention to provide the surgical tracking system as defined above, wherein the field of view function comprises a communicable database comprising n 3D spatial positions; n is an integer greater than or equals to 2; the combination of all of the n 3D spatial positions provides a predetermined field of view; the field of view function is configured to output instructions to the tracking subsystem to instruct the maneuvering system to direct the endoscope to at least one 3D spatial position substantially within the n 3D spatial positions so as to maintain a constant field of view.

It is another object of the present invention to provide the surgical tracking system as defined above, wherein the no fly zone function comprises a communicable database comprising n 3D spatial positions; n is an integer greater than or equals to 2; the n 3D spatial positions define a predetermined volume within the surgical environment; the no fly zone function is configured to output instructions to the tracking subsystem to instruct the maneuvering system to direct the endoscope to at least one 3D spatial position substantially different from all the n 3D spatial positions.

It is another object of the present invention to provide the surgical tracking system as defined above, wherein the most used tool function comprises a communicable database counting the amount of movement of each surgical tool located within the surgical environment; the most used tool function is configured to output instructions to the tracking subsystem to instruct the maneuvering system to direct the endoscope to constantly position the endoscope to track the movement of the most moved surgical tool.

It is another object of the present invention to provide the surgical tracking system as defined above, wherein the prediction function comprises a communicable database storing each 3D spatial position of each of surgical tool within the surgical environment, such that each movement of each surgical tool is stored; the prediction function is configured to (a) to predict the future 3D spatial position of each of the surgical tools; and, (b) to output instructions to the tracking subsystem to instruct the maneuvering system to direct the endoscope to the future 3D spatial position.

It is another object of the present invention to provide the surgical tracking system as defined above, wherein the past statistical analysis function comprises a communicable database storing each 3D spatial position of each of surgical tool within the surgical environment, such that each movement of each surgical tool is stored; the past statistical analysis function is configured to (a) statistical analyze the 3D spatial positions of each of the surgical tools; and, (b) to predict the future 3D spatial position of each of the surgical tools; and, (c) to output instructions to the tracking subsystem to instruct the maneuvering system to direct the endoscope to the future 3D spatial position.

It is another object of the present invention to provide the surgical tracking system as defined above, wherein the a tagged tool function comprises means configured to tag at least one surgical tool within the surgical environment and to output instructions to the tracking subsystem to instruct the maneuvering system to constantly direct the endoscope to the tagged surgical tool.

It is another object of the present invention to provide the surgical tracking system as defined above, wherein the means are configured to constantly tag the at least one of surgical tool within the surgical environment.

It is another object of the present invention to provide the surgical tracking system as defined above, wherein means are configured to re-tag the at least one of the surgical tools until a desired tool is selected.

It is another object of the present invention to provide the surgical tracking system as defined above, additionally comprising means configured to toggle the surgical tools.

It is another object of the present invention to provide the surgical tracking system as defined above, wherein the toggling is performed manually or automatically.

It is another object of the present invention to provide the surgical tracking system as defined above, wherein the image processing is obtained by at least one algorithm selected from the group consisting of: image stabilization algorithm, image improvement algorithm, image compilation algorithm, image enhancement algorithm, image detection algorithm, image classification algorithm, image correlation with the cardiac cycle or the respiratory cycle of the human body, smoke or vapor, steam reduction from the endoscope and any combination thereof.

It is another object of the present invention to provide the surgical tracking system as defined above, wherein the endoscope comprises an image acquisition device selected from the group consisting of: a camera, a video camera, an electromagnetic sensor, a computer tomography imaging device, a fluoroscopic imaging device, an ultrasound imaging device, and any combination thereof.

It is another object of the present invention to provide the surgical tracking system as defined above, further comprising a display configured to provide input or output to the operator regarding the operation of the system.

It is another object of the present invention to provide the surgical tracking system as defined above, wherein the display is used for visualizing the region of interest by the operator.

It is another object of the present invention to provide the surgical tracking system as defined above, wherein the display is configured to output the acquired real-time images of a surgical environment with augmented reality elements.

It is another object of the present invention to provide the surgical tracking system as defined above, wherein the image processing algorithm is configured to analyze 2D or 3D representation rendered from the real-time images of the surgical environment.

It is another object of the present invention to provide the surgical tracking system as defined above, wherein the data processor is further configured to operate a pattern recognition algorithm for assisting the operation of the instructing functions $g_i(t)$.

It is another object of the present invention to provide the surgical tracking system as defined above, additionally comprising at least one location estimating means for locating the position of at least one surgical tool in the surgical environment.

It is another object of the present invention to provide the surgical tracking system as defined above, wherein the at least one location estimating means are an interface subsystem between a surgeon and the at least one surgical tool, the interface subsystem comprises:
   a. at least one array comprising N regular or pattern light sources, where N is a positive integer;
   b. at least one array comprising M cameras, each of the M cameras, where M is a positive integer;
   c. optional optical markers and means for attaching the optical marker to the at least one surgical tool; and,
   d. a computerized algorithm operable via the controller, the computerized algorithm configured to record images received by each camera of each of the M cameras and to calculate therefrom the position of each of the tools, and further configured to provide automatically the results of the calculation to the human operator of the interface.

It is another object of the present invention to provide a method for assisting an operator to perform a laparoscopic surgery of a human body, the method comprising steps of:
   a. providing a surgical tracking system, comprising: (i) at least one endoscope configured to acquire real-time images of a surgical environment within the human body; (ii) a maneuvering subsystem in communication with the endoscope; and, (iii) a tracking subsystem in communication with the maneuvering subsystem, the tracking subsystem comprises a data processor;
   b. performing real-time image processing of the surgical environment;
   c. controlling the maneuvering system via the tracking subsystem, thereby directing and modifying the spatial position of the endoscope to a region of interest according to input received from a maneuvering function f(t);
   wherein the maneuvering function f(t) is configured to (a) receive input from at least two instructing functions $g_i(t)$, where i is 1, . . . , n and n≥2; where t is time; i and n are integers; and, to (b) output instructions to the maneuvering subsystem based on the input from the at least two instructing functions $g_i(t)$, so as to spatially position the endoscope to the region of interest.

It is another object of the present invention to provide the method as defined above, wherein each of the instructing functions $g_i(t)$ is provided with $\alpha_i(t)$ where i is an integer greater than or equals to 1; where $\alpha_i(t)$ are weighting functions of each $g_i(t)$, and a n is total number of instruction functions.

It is another object of the present invention to provide the method as defined above, wherein each of the instructing functions $g_i(t)$ is selected from a group consisting of: most used tool function, a right tool function, left tool function, field of view function, preferred volume zone function, preferred tool function, no fly zone function, a tool detection function, a movement detection function, an organ detection function, a collision detection function, an operator input function, a prediction function, a past statistical analysis function, proximity function, a tagged tool function, and any combination thereof.

It is another object of the present invention to provide the method as defined above, wherein the weighting functions $\alpha_i(t)$ are time-varying functions, wherein the value of which is determined by the operators.

It is another object of the present invention to provide the method as defined above, wherein the tool detection function is configured to detect surgical tools in the surgical environment and to output instructions to the tracking subsystem to instruct the maneuvering system to direct the endoscope on the detected surgical tools.

It is another object of the present invention to provide the method as defined above, wherein the movement detection function comprises a communicable database comprising the real-time 3D spatial positions of each of the surgical tool in the surgical environment; and to detect movement of the at least one surgical tool when a change in the 3D spatial positions is received, and to output instructions to the tracking subsystem to instruct the maneuvering system to direct the endoscope on the moved surgical tool.

It is another object of the present invention to provide the method as defined above, wherein the organ detection function is configured to detect organs in the surgical environment and to output instructions to the tracking subsystem to instruct the maneuvering system to direct the endoscope on the detected organs.

It is another object of the present invention to provide the method as defined above, wherein the right tool function is configured to detect surgical tool positioned to right of the endoscope and to output instructions to the tracking subsystem to instruct the maneuvering system to constantly direct the endoscope on the right tool and to track the right tool.

It is another object of the present invention to provide the method as defined above, wherein the left tool function is configured to detect surgical tool positioned to left of the endoscope and to output instructions to the tracking subsystem to instruct the maneuvering system to constantly direct the endoscope on the left tool and to track the left tool.

It is another object of the present invention to provide the method as defined above, wherein the operator input function comprises a communicable database; the communicable database is configured to receive an input from the operator of the system; the input comprising n 3D spatial positions; n is an integer greater than or equals to 2; and to output instructions to the tracking subsystem to instruct the maneuvering system to direct the endoscope to the at least one 3D spatial position received.

It is another object of the present invention to provide the method as defined above, wherein the proximity function is configured to define a predetermined distance between at least two surgical tools; and to output instructions to the tracking subsystem to instruct the maneuvering system to direct the endoscope to the two surgical tools if the distance between the two surgical tools is less than the predetermined distance.

It is another object of the present invention to provide the method as defined above, wherein the proximity function is configured to define a predetermined angle between at least three surgical tools; and to output instructions to the tracking subsystem to instruct the maneuvering system to direct the endoscope to the three surgical tools if the angle between the two surgical tools is less than or greater than the predetermined angle.

It is another object of the present invention to provide the method as defined above, wherein the preferred volume zone function comprises communicable database comprising n 3D spatial positions; n is an integer greater than or equals to 2; the n 3D spatial positions provides the preferred volume zone; the preferred volume zone function is configured to output instructions to the tracking subsystem to instruct the maneuvering system to direct the endoscope to the preferred volume zone.

It is another object of the present invention to provide the method as defined above, wherein the preferred tool function comprises a communicable database, the database stores a preferred tool; the preferred tool function is configured to output instructions to the tracking subsystem to instruct the maneuvering system to direct the endoscope to the preferred tool.

It is another object of the present invention to provide the method as defined above, wherein the collision prevention function is configured to define a predetermined distance between the at least one surgical tool and an anatomical element within the surgical environment; and to output instructions to the tracking subsystem to instruct the maneuvering system to direct the endoscope to the surgical tool and the anatomical element within the surgical environment if the distance between the at least one surgical tool and an anatomical element is less than the predetermined distance.

It is another object of the present invention to provide the method as defined above, wherein the anatomical element is selected from a group consisting of tissue, organ, another surgical tool or any combination thereof.

It is another object of the present invention to provide the method as defined above, wherein the field of view function comprises a communicable database comprising n 3D spatial positions; n is an integer greater than or equals to 2; the combination of all of the n 3D spatial positions provides a predetermined field of view; the field of view function is configured to output instructions to the tracking subsystem to instruct the maneuvering system to direct the endoscope to at least one 3D spatial position substantially within the n 3D spatial positions so as to maintain a constant field of view.

It is another object of the present invention to provide the method as defined above, wherein the no fly zone function comprises a communicable database comprising n 3D spatial positions; n is an integer greater than or equals to 2; the n 3D spatial positions define a predetermined volume within the surgical environment; the no fly zone function is configured to output instructions to the tracking subsystem to instruct the maneuvering system to direct the endoscope to at least one 3D spatial position substantially different from all the n 3D spatial positions.

It is another object of the present invention to provide the method as defined above, wherein the most used tool function comprises a communicable database counting the amount of movement of each surgical tool located within the surgical environment; the most used tool function is configured to output instructions to the tracking subsystem to instruct the maneuvering system to direct the endoscope to constantly position the endoscope to track the movement of the most moved surgical tool.

It is another object of the present invention to provide the method as defined above, wherein the prediction function comprises a communicable database storing each 3D spatial position of each of surgical tool within the surgical environment, such that each movement of each surgical tool is stored; the prediction function is configured to (a) to predict the future 3D spatial position of each of the surgical tools; and, (b) to output instructions to the tracking subsystem to instruct the maneuvering system to direct the endoscope to the future 3D spatial position.

It is another object of the present invention to provide the method as defined above, wherein the past statistical analysis function comprises a communicable database storing each 3D spatial position of each of surgical tool within the surgical environment, such that each movement of each surgical tool is stored; the past statistical analysis function is configured to (a) statistical analyze the 3D spatial positions of each of the surgical tools; and, (b) to predict the future 3D spatial position of each of the surgical tools; and, (c) to output instructions to the tracking subsystem to instruct the maneuvering system to direct the endoscope to the future 3D spatial position.

It is another object of the present invention to provide the method as defined above, wherein the a tagged tool function comprises means configured to tag at least one surgical tool within the surgical environment and to output instructions to the tracking subsystem to instruct the maneuvering system to constantly direct the endoscope to the tagged surgical tool.

It is another object of the present invention to provide the method as defined above, wherein the means are configured to constantly tag the at least one of surgical tool within the surgical environment.

It is another object of the present invention to provide the method as defined above, wherein means are configured to re-tag the at least one of the surgical tools until a desired tool is selected.

It is another object of the present invention to provide the method as defined above, additionally comprising step of providing means configured to toggle the surgical tools.

It is another object of the present invention to provide the method as defined above, wherein the toggling is performed manually or automatically.

It is another object of the present invention to provide the method as defined above, wherein the image processing is obtained by at least one algorithm selected from the group consisting of: image stabilization algorithm, image improvement algorithm, image compilation algorithm, image enhancement algorithm, image detection algorithm, image classification algorithm, image correlation with the cardiac cycle or the respiratory cycle of the human body, smoke or vapor, steam reduction from the endoscope and any combination thereof.

It is another object of the present invention to provide the method as defined above, wherein the endoscope comprises an image acquisition device selected from the group consisting of: a camera, a video camera, an electromagnetic sensor, a computer tomography imaging device, a fluoroscopic imaging device, an ultrasound imaging device, and any combination thereof.

It is another object of the present invention to provide the method as defined above, further comprising step of providing a display configured to provide input or output to the operator regarding the operation of the system.

It is another object of the present invention to provide the method as defined above, wherein the display is used for visualizing the region of interest by the operator.

It is another object of the present invention to provide the method as defined above, wherein the display is configured to output the acquired real-time images of a surgical environment with augmented reality elements.

It is another object of the present invention to provide the method as defined above, wherein the image processing algorithm is configured to analyze 2D or 3D representation rendered from the real-time images of the surgical environment.

It is another object of the present invention to provide the method as defined above, wherein the data processor is further configured to operate a pattern recognition algorithm for assisting the operation of the instructing functions $g_i(t)$.

It is another object of the present invention to provide the method as defined above, additionally comprising step of preliminary tagging at least one of the surgical tools.

It is another object of the present invention to provide the method as defined above, additionally comprising step of constantly tagging at least one of the surgical tools.

It is another object of the present invention to provide the method as defined above, additionally comprising step of re-tagging the at least one of the surgical tools until a desired tool is selected.

It is another object of the present invention to provide the method as defined above, additionally comprising step of toggling the surgical tools.

It is another object of the present invention to provide the method as defined above, wherein the toggling is performed manually or automatically.

It is another object of the present invention to provide the method as defined above, additionally comprising step of locating the 3D position of at least one surgical tool in the surgical environment.

It is another object of the present invention to provide the method as defined above, wherein the step of locating the 3D position of at least one surgical tool is provided by at least one location estimating means; the at least one location estimating means are an interface subsystem between a surgeon and the at least one surgical tool, the interface subsystem comprises:
  a. at least one array comprising N regular or pattern light sources, where N is a positive integer;
  b. at least one array comprising M cameras, each of the M cameras, where M is a positive integer;
  c. optional optical markers and means for attaching the optical marker to the at least one surgical tool; and,
  d. a computerized algorithm operable via the controller, the computerized algorithm configured to record images received by each camera of each of the M cameras and to calculate therefrom the position of each of the tools, and further configured to provide automatically the results of the calculation to the human operator of the interface.

It is another object of the present invention to provide a surgical controlling system, comprising:
  a. at least one endoscope configured to provide real-time image of surgical environment of a human body;
  b. at least one processing means, configured to real time define n element within the real-time image of surgical environment of a human body; each of the elements is characterized by predetermined characteristics;

c. image processing means in communication with the endoscope, configured to image process the real-time image and to provide real time updates of the predetermined characteristics;

d. a communicable database, in communication with the processing means and the image processing means, configured to store the predetermined characteristics and the updated characteristics;

wherein the system is configured to notify if the updated characteristics are substantially different from the predetermined characteristics.

It is another object of the present invention to provide the surgical controlling system as defined above, wherein the predetermined characteristics are selected from a group consisting of color of the element, 3D spatial location of the element, contours of the element, and any combination thereof.

It is another object of the present invention to provide the surgical controlling system as defined above, additionally comprising at least one surgical tool configured to be inserted into a surgical environment of a human body for assisting a surgical procedure.

It is another object of the present invention to provide the surgical controlling system as defined above, additionally comprising (a) at least one location estimating means configured to real-time estimate the location of the at least one surgical tool at any given time t; and, (b) at least one movement detection means communicable with a movement's database and with said location estimating means; said movement's database is configured to store said 3D spatial position of said at least one surgical tool at time $t_f$ and at time $t_0$; where $t_f > t_0$; said movement detection means is configured to detect movement of said at least one surgical tool if the 3D spatial position of said at least one surgical tool at time $t_f$ is different than said 3D spatial position of said at least one surgical tool at time $t_0$.

It is another object of the present invention to provide the surgical controlling system as defined above, additionally comprising a controller having a processing means communicable with a controller's database, the controller configured to control the spatial position of the at least one surgical tool.

It is another object of the present invention to provide the surgical controlling system as defined above, wherein the controller's database is configured to store a predetermined set of rules according to which allowed and restricted movements of the at least one surgical tool are determined, such that each detected movement by said movement detection means of said at least one surgical tool is determined as either an allowed movement or as a restricted movement according to said predetermined set of rules.

It is another object of the present invention to provide the surgical controlling system as defined above, wherein the predetermined set of rules comprises at least one rule selected from the group consisting of: most used tool rule, right tool rule, left tool rule, field of view rule, no fly zone rule, route rule, environmental rule, operator input rule, proximity rule; collision prevention rule, history based rule, tool-dependent allowed and restricted movements rule, preferred volume zone rule, preferred tool rule, movement detection rule, and any combination thereof.

It is another object of the present invention to provide the surgical controlling system as defined above, wherein the route rule comprises a communicable database storing predefined route in which the at least one surgical tool is configured to move within the surgical environment; the predefined route comprises n 3D spatial positions of the at least one surgical tool; n is an integer greater than or equals to 2; the allowed movements are movements in which the at least one surgical tool is located substantially in at least one of the n 3D spatial positions of the predefined route, and the restricted movements are movements in which the location of the at least one surgical tool is substantially different from the n 3D spatial positions of the predefined route.

It is another object of the present invention to provide the surgical controlling system as defined above, wherein the environmental rule comprises a comprises a communicable database; the communicable database is configured to received real-time image of the surgical environment and is configured to perform real-time image processing of the same and to determined the 3D spatial position of hazards or obstacles in the surgical environment; the environmental rule is configured to determine the allowed and restricted movements according to the hazards or obstacles in the surgical environment, such that the restricted movements are movements in which the at least one surgical tool is located substantially in at least one of the 3D spatial positions, and the allowed movements are movements in which the location of the at least one surgical tool is substantially different from the 3D spatial positions.

It is another object of the present invention to provide the surgical controlling system as defined above, wherein the hazards or obstacles in the surgical environment are selected from a group consisting of tissue, a surgical tool, an organ, an endoscope and any combination thereof.

It is another object of the present invention to provide the surgical controlling system as defined above, wherein the operator input rule comprises a communicable database; the communicable database is configured to receive an input from the operator of the system regarding the allowed and restricted movements of the at least one surgical tool.

It is another object of the present invention to provide the surgical controlling system as defined above, wherein the input comprises n 3D spatial positions; n is an integer greater than or equals to 2; wherein at least one of which is defined as allowed location and at least one of which is defined as restricted location, such that the allowed movements are movements in which the at least one surgical tool is located substantially in at least one of the n 3D spatial positions, and the restricted movements are movements in which the location of the at least one surgical tool is substantially different from the n 3D spatial positions.

It is another object of the present invention to provide the surgical controlling system as defined above, wherein the input comprises at least one rule according to which allowed and restricted movements of the at least one surgical tool are determined, such that the spatial position of the at least one surgical tool is controlled by the controller according to the allowed and restricted movements.

It is another object of the present invention to provide the surgical controlling system as defined above, wherein the predetermined set of rules comprises at least one rule selected from the group consisting of: most used tool, right tool rule, left tool rule, field of view rule, no fly zone rule, a route rule, an environmental rule, an operator input rule, a proximity rule; a collision prevention rule, preferred volume zone rule, movement detection rule, a history based rule, a tool-dependent allowed and restricted movements rule, and any combination thereof.

It is another object of the present invention to provide the surgical controlling system as defined above, wherein the operator input rule converts an allowed movement to a restricted movement and a restricted movement to an allowed movement.

It is another object of the present invention to provide the surgical controlling system as defined above, wherein the proximity rule is configured to define a predetermined distance between at least two surgical tools; the allowed movements are movements which are within the range or out of the range of the predetermined distance, and the restricted movements which are out of the range or within the range of the predetermined distance.

It is another object of the present invention to provide the surgical controlling system as defined above, wherein the proximity rule is configured to define a predetermined angle between at least three surgical tools; the allowed movements are movements which are within the range or out of the range of the predetermined angle, and the restricted movements which are out of the range or within the range of the predetermined angle.

It is another object of the present invention to provide the surgical controlling system as defined above, wherein the collision prevention rule is configured to define a predetermined distance between the at least one surgical tool and an anatomical element within the surgical environment; the allowed movements are movements which are in a range that is larger than the predetermined distance, and the restricted movements are movements which is in a range that is smaller than the predetermined distance.

It is another object of the present invention to provide the surgical controlling system as defined above, wherein the anatomical element is selected from a group consisting of tissue, organ, another surgical tool or any combination thereof.

It is another object of the present invention to provide the surgical controlling system as defined above, wherein at least one of the following is being held true (a) said system additionally comprising an endoscope; said endoscope is configured to provide real-time image of said surgical environment; (b) at least one of said surgical tools is an endoscope configured to provide real-time image of said surgical environment.

It is another object of the present invention to provide the surgical controlling system as defined above, wherein the right tool rule is configured to determine the allowed movement of the endoscope according to the movement of the surgical tool positioned to right of the endoscope.

It is another object of the present invention to provide the surgical controlling system as defined above, wherein the left tool rule is configured to determine the allowed movement of the endoscope according to the movement of the surgical tool positioned to left of the endoscope.

It is another object of the present invention to provide the surgical controlling system as defined above, wherein the field of view rule comprises a communicable database comprising n 3D spatial positions; n is an integer greater than or equals to 2; the combination of all of the n 3D spatial positions provides a predetermined field of view; the field of view rule is configured to determine the allowed movement of the endoscope within the n 3D spatial positions so as to maintain a constant field of view, such that the allowed movements are movements in which the endoscope is located substantially in at least one of the n 3D spatial positions, and the restricted movements are movements in which the location of the endoscope is substantially different from the n 3D spatial positions.

It is another object of the present invention to provide the surgical controlling system as defined above, wherein the preferred volume zone rule comprises a communicable database comprising n 3D spatial positions; n is an integer greater than or equals to 2; the n 3D spatial positions provides the preferred volume zone; the preferred volume zone rule is configured to determine the allowed movement of the endoscope within the n 3D spatial positions and restricted movement of the endoscope outside the n 3D spatial positions, such that the allowed movements are movements in which the endoscope is located substantially in at least one of the n 3D spatial positions, and the restricted movements are movements in which the location of the endoscope is substantially different from the n 3D spatial positions.

It is another object of the present invention to provide the surgical controlling system as defined above, wherein the preferred tool rule comprises a communicable database, the database stores a preferred tool; the preferred tool rule is configured to determine the allowed movement of the endoscope according to the movement of the preferred tool.

It is another object of the present invention to provide the surgical controlling system as defined above, wherein the no fly zone rule comprises a communicable database comprising n 3D spatial positions; n is an integer greater than or equals to 2; the n 3D spatial positions define a predetermined volume within the surgical environment; the no fly zone rule is configured to determine the restricted movement if the movement is within the no fly zone and the allowed movement if the movement is outside the no fly zone, such that the restricted movements are movements in which the at least one of the surgical tool is located substantially in at least one of the n 3D spatial positions, and the allowed movements are movements in which the location of the at least one surgical tool is substantially different from the n 3D spatial positions.

It is another object of the present invention to provide the surgical controlling system as defined above, wherein the most used tool rule comprises a communicable database counting the amount of movement of each of the surgical tools; the most used tool rule is configured to constantly position the endoscope to track the movement of the most moved surgical tool.

It is another object of the present invention to provide the surgical controlling system as defined above, wherein said system further comprising a maneuvering subsystem communicable with said controller, said maneuvering subsystem is configured to spatially reposition said at least one surgical tool during a surgery according to said predetermined set of rules; further wherein the system is configured to alert the physician of a restricted movements of the at least one surgical tool.

It is another object of the present invention to provide the surgical controlling system as defined above, wherein the alert is selected from a group consisting of audio signaling, voice signaling, light signaling, flashing signaling and any combination thereof.

It is another object of the present invention to provide the surgical controlling system as defined above, wherein the allowed movement is permitted by the controller and a restricted movement is denied by the controller.

It is another object of the present invention to provide the surgical controlling system as defined above, wherein the history based rule comprises a communicable database storing each 3D spatial position of each of the surgical tool, such that each movement of each surgical tool is stored; the history based rule is configured to determine the allowed and restricted movements according to historical movements of the at least one surgical tool, such that the allowed movements are movements in which the at least one surgical tool is located substantially in at least one of the 3D spatial positions, and the restricted movements are movements in which the location of the at least one surgical tool is substantially different from the n 3D spatial positions.

It is another object of the present invention to provide the surgical controlling system as defined above, wherein the tool-dependent allowed and restricted movements rule comprises a communicable database; the communicable database is configured to store predetermined characteristics of at least one of the surgical tool; the tool-dependent allowed and restricted movements rule is configured to determine the allowed and restricted movements according to the predetermined characteristics of the surgical tool.

It is another object of the present invention to provide the surgical controlling system as defined above, wherein the predetermined characteristics of the surgical tool are selected from the group consisting of: physical dimensions, structure, weight, sharpness, and any combination thereof.

It is another object of the present invention to provide the surgical controlling system as defined above, wherein the movement detection rule comprises a communicable database comprising the real-time 3D spatial positions of each of the surgical tool; and to detect movement of the at least one surgical tool when a change in the 3D spatial positions is received, such that the allowed movements are movements in which the endoscope is directed to focus on the moving surgical tool.

It is another object of the present invention to provide the surgical controlling system as defined above, further comprising a maneuvering subsystem communicable with the controller, the maneuvering subsystem is configured to spatially reposition at least one surgical tool during a surgery according to the predetermined set of rules, such that if said movement of said at least one surgical tool is a restricted movement, said maneuvering subsystem prevents said movement.

It is another object of the present invention to provide the surgical controlling system as defined above, further comprising at least one location estimating means configured to acquire real-time images of the surgical environment within the human body for the estimation of the 3D spatial position of at least one surgical tool.

It is another object of the present invention to provide the surgical controlling system as defined above, wherein the at least one location estimating means are comprises at least one selected from a group consisting of optical imaging means, radio frequency transmitting and receiving means, at least one mark on the at least one surgical tool and any combination thereof.

It is another object of the present invention to provide a method for controlling surgical surgery, comprising step of:
  a. obtaining a system comprising:
    i. at least one endoscope configured to provide real-time image of surgical environment of a human body;
    ii. at least one processing means, configured to real time define n element within the real-time image of surgical environment of a human body; each of the elements is characterized by predetermined characteristics;
    iii. image processing means in communication with the endoscope, configured to image process the real-time image and to provide real time updates of the predetermined characteristics;
    iv. a communicable database, in communication with the processing means and the image processing means, configured to store the predetermined characteristics and the updated characteristics;
  b. providing a real-time image of surgical environment of a human body;
  c. defining the n element;
  d. characterizing each of the element with predetermined characteristics;
  e. providing a real-time update of the predetermined characteristics;
  f. notifying the user if the updated characteristics are substantially different from the predetermined characteristics.

It is another object of the present invention to provide the method as defined above, wherein the predetermined characteristics are selected from a group consisting of color of the element, 3D spatial location of the element, contours of the element, and any combination thereof.

It is another object of the present invention to provide the method as defined above, additionally comprising at least one surgical tool configured to be inserted into a surgical environment of a human body for assisting a surgical procedure.

It is another object of the present invention to provide the method as defined above, additionally comprising (a) at least one location estimating means configured to real-time estimate the location of the at least one surgical tool at any given time t; and, (b) at least one movement detection means communicable with a movement's database and with said location estimating means; said movement's database is configured to store said 3D spatial position of said at least one surgical tool at time $t_f$ and at time $t_0$; where $t_f > t_0$; said movement detection means is configured to detect movement of said at least one surgical tool if the 3D spatial position of said at least one surgical tool at time $t_f$ is different than said 3D spatial position of said at least one surgical tool at time $t_0$.

It is another object of the present invention to provide the method as defined above, additionally comprising a controller having a processing means communicable with a controller's database, the controller configured to control the spatial position of the at least one surgical tool.

It is another object of the present invention to provide the method as defined above, wherein the controller's database is configured to store a predetermined set of rules according to which allowed and restricted movements of the at least one surgical tool are determined, such that each detected movement by said movement detection means of said at least one surgical tool is determined as either an allowed movement or as a restricted movement according to said predetermined set of rules.

It is another object of the present invention to provide the method as defined above, wherein the predetermined set of rules comprises at least one rule selected from the group consisting of: most used tool, right tool rule, left tool rule, field of view rule, no fly zone rule, a route rule, an environmental rule, an operator input rule, a proximity rule; a collision prevention rule, preferred volume zone rule, preferred tool rule, movement detection rule, a history based rule, a tool-dependent allowed and restricted movements rule, and any combination thereof.

It is another object of the present invention to provide the method as defined above, wherein the route rule comprises a communicable database storing predefined route in which the at least one surgical tool is configured to move within the surgical environment; the predefined route comprises n 3D spatial positions of the at least one surgical tool; n is an integer greater than or equals to 2; the allowed movements are movements in which the at least one surgical tool is located substantially in at least one of the n 3D spatial positions of the predefined route, and the restricted movements are movements in which the location of the at least one surgical tool is substantially different from the n 3D spatial positions of the predefined route.

It is another object of the present invention to provide the method as defined above, wherein the environmental rule comprises a comprises a communicable database; the communicable database is configured to received real-time image of the surgical environment and is configured to perform real-time image processing of the same and to determined the 3D spatial position of hazards or obstacles in the surgical environment; the environmental rule is configured to determine the allowed and restricted movements according to the hazards or obstacles in the surgical environment, such that the restricted movements are movements in which the at least one surgical tool is located substantially in at least one of the 3D spatial positions, and the allowed movements are movements in which the location of the at least one surgical tool is substantially different from the 3D spatial positions.

It is another object of the present invention to provide the method as defined above, wherein the hazards or obstacles in the surgical environment are selected from a group consisting of tissue, a surgical tool, an organ, an endoscope and any combination thereof.

It is another object of the present invention to provide the method as defined above, wherein the operator input rule comprises a communicable database; the communicable database is configured to receive an input from the operator of the system regarding the allowed and restricted movements of the at least one surgical tool.

It is another object of the present invention to provide the method as defined above, wherein the input comprises n 3D spatial positions; n is an integer greater than or equals to 2; wherein at least one of which is defined as allowed location and at least one of which is defined as restricted location, such that the allowed movements are movements in which the at least one surgical tool is located substantially in at least one of the n 3D spatial positions, and the restricted movements are movements in which the location of the at least one surgical tool is substantially different from the n 3D spatial positions.

It is another object of the present invention to provide the method as defined above, wherein the input comprises at least one predetermined rule according to which allowed and restricted movements of the at least one surgical tool are determined, such that the spatial position of the at least one surgical tool is controlled by the controller according to the allowed and restricted movements.

It is another object of the present invention to provide the method as defined above, wherein the predetermined rule is selected from the group consisting of: most used tool, right tool rule, left tool rule, field of view rule, no fly zone rule, a route rule, an environmental rule, an operator input rule, a proximity rule; a collision prevention rule, preferred volume zone rule, preferred tool rule, movement detection rule, a history based rule, a tool-dependent allowed and restricted movements rule, and any combination thereof.

It is another object of the present invention to provide the method as defined above, wherein the operator input rule converts an allowed movement to a restricted movement and a restricted movement to an allowed movement.

It is another object of the present invention to provide the method as defined above, wherein the proximity rule is configured to define a predetermined distance between at least two surgical tools; the allowed movements are movements which are within the range or out of the range of the predetermined distance, and the restricted movements which are out of the range or within the range of the predetermined distance.

It is another object of the present invention to provide the method as defined above, wherein the proximity rule is configured to define a predetermined angle between at least three surgical tools; the allowed movements are movements which are within the range or out of the range of the predetermined angle, and the restricted movements which are out of the range or within the range of the predetermined angle.

It is another object of the present invention to provide the method as defined above, wherein the collision prevention rule is configured to define a predetermined distance between the at least one surgical tool and an anatomical element within the surgical environment; the allowed movements are movements which are in a range that is larger than the predetermined distance, and the restricted movements are movements which is in a range that is smaller than the predetermined distance.

It is another object of the present invention to provide the method as defined above, wherein the anatomical element is selected from a group consisting of tissue, organ, another surgical tool or any combination thereof.

It is another object of the present invention to provide the method as defined above, wherein at least one of the following is being held true (a) said system additionally comprising an endoscope; said endoscope is configured to provide real-time image of said surgical environment; (b) at least one of said surgical tools is an endoscope configured to provide real-time image of said surgical environment.

It is another object of the present invention to provide the method as defined above, wherein the right tool rule is configured to determine the allowed movement of the endoscope according to the movement of the surgical tool positioned to right of the endoscope.

It is another object of the present invention to provide the method as defined above, wherein the left tool rule is configured to determine the allowed movement of the endoscope according to the movement of the surgical tool positioned to left of the endoscope.

It is another object of the present invention to provide the method as defined above, wherein the field of view rule comprises a communicable database comprising n 3D spatial positions; n is an integer greater than or equals to 2; the combination of all of the n 3D spatial positions provides a predetermined field of view; the field of view rule is configured to determine the allowed movement of the endoscope within the n 3D spatial positions so as to maintain a constant field of view, such that the allowed movements are movements in which the endoscope is located substantially in at least one of the n 3D spatial positions, and the restricted movements are movements in which the location of the endoscope is substantially different from the n 3D spatial positions.

It is another object of the present invention to provide the method as defined above, wherein the preferred volume zone rule comprises a communicable database comprising n 3D spatial positions; n is an integer greater than or equals to 2; the n 3D spatial positions provides the preferred volume zone; the preferred volume zone rule is configured to determine the allowed movement of the endoscope within the n 3D spatial positions and restricted movement of the endoscope outside the n 3D spatial positions, such that the allowed movements are movements in which the endoscope is located substantially in at least one of the n 3D spatial positions, and the restricted movements are movements in which the location of the endoscope is substantially different from the n 3D spatial positions.

It is another object of the present invention to provide the method as defined above, wherein the preferred tool rule comprises a communicable database, the database stores a preferred tool; the preferred tool rule is configured to determine the allowed movement of the endoscope according to the movement of the preferred tool.

It is another object of the present invention to provide the method as defined above, wherein the no fly zone rule comprises a communicable database comprising n 3D spatial positions; n is an integer greater than or equals to 2; the n 3D spatial positions define a predetermined volume within the surgical environment; the no fly zone rule is configured to determine the restricted movement if the movement is within the no fly zone and the allowed movement if the movement is outside the no fly zone, such that the restricted movements are movements in which the at least one of the surgical tool is located substantially in at least one of the n 3D spatial positions, and the allowed movements are movements in which the location of the at least one surgical tool is substantially different from the n 3D spatial positions.

It is another object of the present invention to provide the method as defined above, wherein the most used tool rule comprises a communicable database counting the amount of movement of each of the surgical tools; the most used tool rule is configured to constantly position the endoscope to track the movement of the most moved surgical tool.

It is another object of the present invention to provide the method as defined above, additionally comprising step of alerting the physician of a restricted movement of the at least one surgical tool.

It is another object of the present invention to provide the method as defined above, wherein the alert is selected from a group consisting of audio signaling, voice signaling, light signaling, flashing signaling and any combination thereof.

It is another object of the present invention to provide the method as defined above, wherein the allowed movement is permitted by the controller and a restricted movement is denied by the controller.

It is another object of the present invention to provide the method as defined above, wherein the history based rule comprises a communicable database storing each 3D spatial position of each of the surgical tool, such that each movement of each surgical tool is stored; the history based rule is configured to determine the allowed and restricted movements according to historical movements of the at least one surgical tool, such that the allowed movements are movements in which the at least one surgical tool is located substantially in at least one of the 3D spatial positions, and the restricted movements are movements in which the location of the at least one surgical tool is substantially different from the n 3D spatial positions.

It is another object of the present invention to provide the method as defined above, wherein the tool-dependent allowed and restricted movements rule comprises a communicable database; the communicable database is configured to store predetermined characteristics of at least one of the surgical tool; the tool-dependent allowed and restricted movements rule is configured to determine the allowed and restricted movements according to the predetermined characteristics of the surgical tool.

It is another object of the present invention to provide the method as defined above, wherein the predetermined characteristics of the surgical tool are selected from the group consisting of: physical dimensions, structure, weight, sharpness, and any combination thereof.

It is another object of the present invention to provide the method as defined above, wherein the movement detection rule comprises a communicable database comprising the real-time 3D spatial positions of each of the surgical tool; and to detect movement of the at least one surgical tool when a change in the 3D spatial positions is received, such that the allowed movements are movements in which the endoscope is directed to focus on the moving surgical tool.

It is another object of the present invention to provide the method as defined above, further comprising step of proving a maneuvering subsystem communicable with the controller, the maneuvering subsystem is configured to spatially reposition the at least one surgical tool during a surgery according to the predetermined set of rules.

It is another object of the present invention to provide a surgical controlling system, comprising:
  (a) at least one surgical tool configured to be inserted into a surgical environment of a human body for assisting a surgical procedure;
  (b) at least one endoscope configured to provide real-time image of said surgical environment;
  (c) at least one location estimating means configured to real-time locate the 3D spatial position of said at least one surgical tool at any given time t;
  (d) at least one movement detection means communicable with a movement's database and with said location estimating means; said movement's database is configured to store said 3D spatial position of said at least one surgical tool at time $t_f$ and at time $t_0$; where $t_f > t_0$; said movement detection means is configured to detect movement of said at least one surgical tool if the 3D spatial position of said at least one surgical tool at time $t_f$ is different than said 3D spatial position of said at least one surgical tool at time $t_0$; and,
  (e) a controller having a processing means communicable with a controller's database, said controller configured to control the spatial position of said at least one surgical tool; said controller's database is in communication with said movement detection means;
wherein said controller's database comprising n 3D spatial positions; n is an integer greater than or equal to 2; the combination of all of said n 3D spatial positions provides a predetermined field of view; said controller is configured to relocate the 3D spatial positions of said endoscope if movement has been detected by said detection means, such that said field of view is maintained.

It is another object of the present invention to provide the surgical controlling system as defined above, wherein controller's database comprises n 3D spatial positions; n is an integer greater than or equal to 2; the combination of all of said n 3D spatial positions provides a predetermined field of view; said field of view rule is configured to relocate said endoscope if movement of at least one of said surgical tools has been detected by said detection means, such that said field of view is maintained.

It is another object of the present invention to provide the method as defined above, wherein controller's database comprises n 3D spatial positions; n is an integer greater than or equal to 2; the combination of all of said n 3D spatial positions provides a predetermined field of view; said field of view rule is configured to relocate said endoscope if movement of at least one of said surgical tools has been detected by said detection means, such that said field of view is maintained.

It is another object of the present invention to provide the surgical tracking system as defined above, wherein controller's database comprises n 3D spatial positions; n is an integer greater than or equal to 2; the combination of all of said n 3D spatial positions provides a predetermined field of view; said field of view rule is configured to relocate said endoscope if movement of at least one of said surgical tools has been detected by said detection means, such that said field of view is maintained.

It is another object of the present invention to provide the method as defined above, wherein controller's database comprises n 3D spatial positions; n is an integer greater than or equal to 2; the combination of all of said n 3D spatial positions provides a predetermined field of view; said field of view rule is configured to relocate said endoscope if movement of at least one of said surgical tools has been detected by said detection means, such that said field of view is maintained.

It is another object of the present invention to provide the surgical controlling system as defined above, wherein controller's database comprises n 3D spatial positions; n is an integer greater than or equal to 2; the combination of all of said n 3D spatial positions provides a predetermined field of view; said field of view rule is configured to relocate said endoscope if movement of at least one of said surgical tools has been detected by said detection means, such that said field of view is maintained.

It is another object of the present invention to provide the method as defined above, wherein controller's database comprises n 3D spatial positions; n is an integer greater than or equal to 2; the combination of all of said n 3D spatial positions provides a predetermined field of view; said field of view rule is configured to relocate said endoscope if movement of at least one of said surgical tools has been detected by said detection means, such that said field of view is maintained.

BRIEF DESCRIPTION OF THE FIGURES

In order to understand the invention and to see how it may be implemented in practice, and by way of non-limiting example only, with reference to the accompanying drawing, in which

FIG. 4A-D schematically illustrates operation of an embodiment of a tracking system with collision avoidance system;

FIGS. 18A-B, 19A-B and 20A-B schematically illustrate embodiments of a tracking system with a fixed point rule/function;

FIGS. 21A-C schematically illustrate an embodiment of a tracking system with a virtual rotation of scene rule/function;

FIGS. 22A-B and 23 A-B schematically illustrate an embodiment of a tracking system with an input protocol in which a tool is moved;

DETAILED DESCRIPTION OF THE PREFERRED EMBODIMENTS

Figure 1:
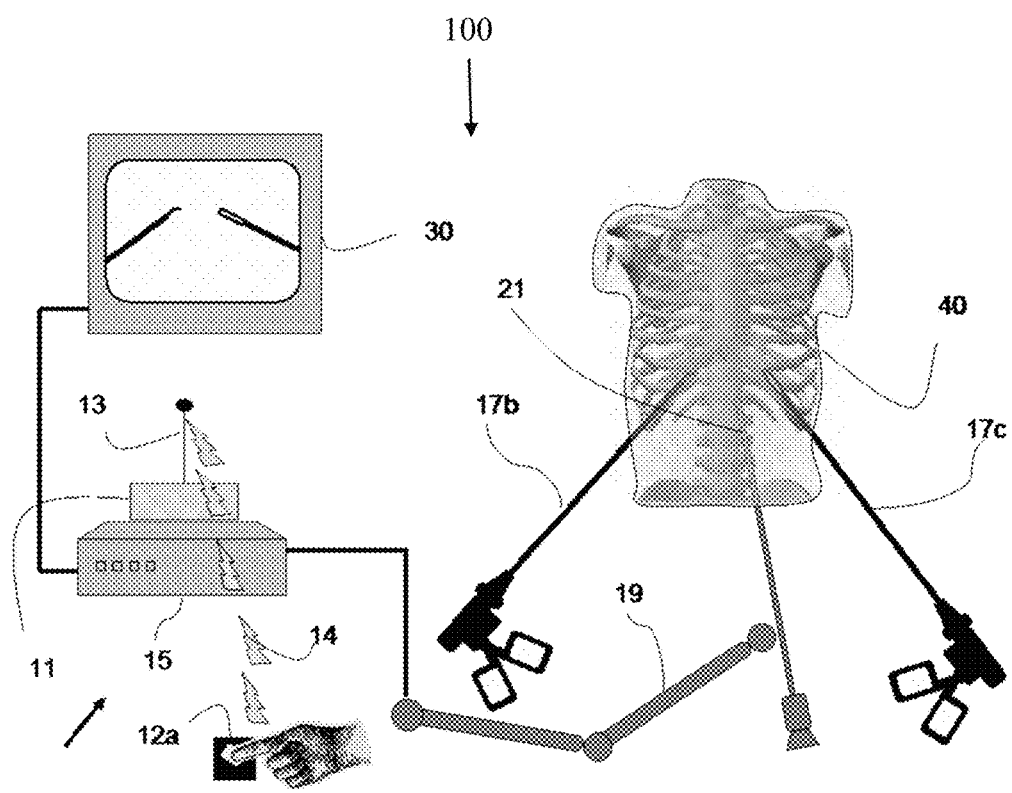
FIGS. 1-2 illustrate an embodiment of the present invention.

Before explaining at least one embodiment of the invention in detail, it is to be understood that the invention is not limited in its application to the details of construction and the arrangement of the components set forth in the following description or illustrated in the drawings. The invention is applicable to other embodiments or of being practiced or carried out in various ways. Also, it is to be understood that the phraseology and terminology employed herein is for the purpose of description and should not be regarded as limiting.

The term 'toggle' refers hereinafter to switching between one tagged surgical tool to another.

The term 'surgical environment' refers hereinafter to any anatomical part within the human body which may be in surrounding a surgical instrument. The environment may comprise: organs, body parts, walls of organs, arteries, veins, nerves, a region of interest, or any other anatomical part of the human body.

The term 'endoscope' refers hereinafter to any means configured for looking inside the body for medical reasons. This may be any instrument used to examine the interior of a hollow organ or cavity of the body. The endoscope may also refer to any kind of a laparascope. It should be pointed that the following description may refer to an endoscope as a surgical tool.

The term 'region of interest' refers hereinafter to any region within the human body which may be of interest to the operator of the system of the present invention. The region of interest may be, for example, an organ to be operated on, a restricted area to which approach of a surgical instrument is restricted, a surgical instrument, or any other region within the human body.

The term 'spatial position' refers hereinafter to a predetermined spatial location and/or orientation of an object (e.g., the spatial location of the endoscope, the angular orientation of the endoscope, and any combination thereof).

The term 'prohibited area' refers hereinafter to a predetermined area to which a surgical tool (e.g., an endoscope) is prohibited to be spatially positioned in.

The term 'preferred area' refers hereinafter to predetermined area to which a surgical tool (e.g., an endoscope) is allowed and/or preferred to be spatially positioned in.

The term 'automated assistant' refers hereinafter to any mechanical device (including but not limited to a robotic device) that can maneuver and control the position of a surgical or endoscopic instrument, and that can in addition be configured to receive commands from a remote source.

The term 'tool' or 'surgical instrument' refers hereinafter to any instrument or device introducible into the human body. The term may refer to any location on the tool. For example it can refer to the tip of the same, the body of the same and any combination thereof. It should be further pointed that the following description may refer to a surgical tool/instrument as an endoscope.

The term 'provide' refers hereinafter to any process (visual, tactile, or auditory) by which an instrument, computer, controller, or any other mechanical or electronic device can report the results of a calculation or other operation to a human operator.

The term 'automatic' or 'automatically' refers to any process that proceeds without the necessity of direct intervention or action on the part of a human being.

The term 'allowed movement' refers hereinafter to any movement of a surgical tool which is permitted according to a predetermined set of rules.

The term 'restricted movement' refers hereinafter to any movement of a surgical tool which is forbidden according to a predetermined set of rules. For example, one rule, according to the present invention, provides a preferred volume zone rule which defines a favored zone within the surgical environment. Thus, according to the present invention an allowed movement of a surgical tool or the endoscope is a movement which maintains the surgical tool within the favored zone; and a restricted movement of a surgical tool is a movement which extracts (or moves) the surgical tool outside the favored zone.

The term 'time step' refers hereinafter to the working time of the system. At each time step, the system receives data from sensors and commands from operators and processes the data and commands and executes actions. The time step size is the elapsed time between time steps.

The term 'location' refers hereinafter to any point, 3D point, area or volume of an element. Laparoscopic surgery, also called minimally invasive surgery (MIS), is a modern surgical technique in which operations in the abdomen are performed through small incisions (usually 0.5-1.5 cm) as compared to larger incisions needed in traditional surgical procedures. The key element in laparoscopic surgery is the use of a laparoscope, which is a device configured for viewing the scene within the body, at the distal end of the laparoscope. Either an imaging device is placed at the end of the laparoscope, or a rod lens system or fiber optic bundle is used to direct this image to the proximal end of the laparoscope. Also attached is a light source to illuminate the operative field, inserted through a 5 mm or 10 mm cannula or trocar to view the operative field.

The term 'moving element' refers hereinafter to either an object whose movement can be sensed or a means of sensing future movement of the object. A movement of a moving element can include, but is not limited to, movement of at least a portion of at surgical tool (such as, for non-limiting example the distal end of a surgical tool), movement of at least a portion of the body of at least one operator, intended movement of at least a portion of the body of at least one operator, a brain signal from at least one operator, a sound signal and any combination thereof. Movement of the portion of the body can be determined, for non-limiting example, via brain signals (e.g., the brain signals commanding a movement), via sensors measuring the movement of the portion of the body, or via electrical or magnetic signals indicating change in at least one muscle. Intended movement can be measured via brain signals from the operator (for non-limiting examples, "next, I will open that grasper", or "that's dangerous—we had better stop it"). sound signals can include voice commands or other predetermined sound patterns.

The term 'article' refers hereinafter to an object in the surgical environment. Articles can include, but are not limited to, of at least a portion of a tool, at least a portion of an endoscope, at least a portion of a body, at least a portion of an organ, at least a portion of a tissue, at least a portion of an object and any combination thereof, where tissue refers to a structure in the body including, but not limited to, a membrane, a ligament, fat, mesentery, a blood vessel, a nerve, bone, cartilage, a tumor, a cyst and any combination thereof and an object can include a swab, suture thread, a towel, a sponge, a knife blade, a scalpel blade, a pin, a safety pin, a tip, a tube, an adapter, a guide such as a cutting guide, a measurement device and any combination thereof.

The term 'output protocol' refers hereinafter to an action or set of actions carried out by the system. Output protocols can comprise, but are not limited to, tagging an article in the surgical environment, tracking an article in the surgical environment, zooming an endoscope, activating or deactivating a tool or an endoscope, articulating a tool or endoscope, and any combination thereof, The term 'input protocol' refers hereinafter to a command or set of commands which indicate to the system that a predefined output protocol is to be carried out. Input protocols can include, but are not limited to, shaking the tool or other moving element, moving a tool or other moving element in at least a portion of a circle, moving a tool or other moving element in at least a portion of an oval, moving a tool or other moving element in at least a portion of an ellipse, moving a tool or other moving element in a straight line, moving a tool or other moving element in a zigzag, rotating a tool or other moving element in a predetermined manner, translating a tool or other moving element in a predetermined manner, The abdomen is usually injected with carbon dioxide gas to create a working and viewing space. The abdomen is essentially blown up like a balloon (insufflated), elevating the abdominal wall above the internal organs like a dome. Within this space, various medical procedures can be carried out.

In many cases, the laparoscope cannot view the entire working space within the body, so the laparoscope is repositioned to allow the surgeon to view regions of interest within the space. The present invention discloses a surgical controlling system configured to control the position of at least one surgical tool during a surgery of the human body. The system may perform the control by identifying the location of the surgical tool, and provide instruction to the operator to which direction the surgical tool may or should be directed, and to which direction the surgical tool is restricted from being moved to.

According to some embodiments of the present invention, the surgical controlling system comprises the following components:
 a. at least one surgical tool configured to be inserted into a surgical environment of a human body for assisting a surgical procedure;
 b. at least one location estimating means configured to real-time estimate/locate the location (i.e., the 3D spatial position) of the at least one surgical tool at any given time t;
 c. at least one movement detection means communicable with a movement-database and with said location estimating means; said movement-database is configured to store said 3D spatial position of said at least one surgical tool at time $t_f$ and at time $t_0$; where $t_f > t_0$; said movement detection means is configured to detect movement of said at least one surgical tool if the 3D spatial position of said at least one surgical tool at time $t_f$ is different than said 3D spatial position of said at least one surgical tool at time $t_O$; and,
 d. a controller having a processing means communicable with a database, the controller configured to control the spatial position of the at least one surgical tool;

It is within the scope of the present invention that the database is configured to store a predetermined set of rules according to which allowed and restricted movements of the at least one surgical tool are determined, such that the spatial position of the at least one surgical tool is controlled by the controller according to the allowed and restricted movements. In other words, each detected movement by said movement detection means of said at least one surgical tool is determined as either an allowed movement or as a restricted movement according to said predetermined set of rules.

Thus, the present invention stores the 3D spatial position of each of said surgical tools at a current at time $t_f$ and at time $t_0$; where $t_f > t_0$. If the 3D spatial position of said at least one surgical tool at time $t_f$ is different than said 3D spatial position of said at least one surgical tool at time $t_O$ movement of the tool is detected. Next the system analyses said movement according to said set of rule and process whether said movement is allowed movement or restricted movement.

According to some embodiments of the present invention, the system prevents said movement, if said movement is a restricted movement. Said movement prevention is obtained by controlling a maneuvering system which prevents the movement of said surgical tool.

According to some embodiments of the present invention, the system does not prevent said movement, (if said movement is a restricted movement), but merely signals/alerts the user (i.e., the physician) of said restricted movement.

According to some embodiments of the present invention, said surgical tool is an endoscope.

According to some embodiments of the present invention, the controller may provide a suggestion to the operator as to which direction the surgical tool has to move to or may be moved to.

Thus, according to a preferred embodiment of the present invention, the present invention provides a predetermined set of rules which define what is an "allowed movement" of any surgical tool within the surgical environment and what is a "restricted movement" of any surgical tool within the surgical environment.

According to some embodiments the system of the present invention comprises a maneuvering subsystem communicable with the controller, the maneuvering subsystem is configured to spatially reposition the at least one surgical tool during surgery according to the predetermined set of rules.

According to some embodiments, the controller may provide instructions to a maneuvering subsystem for spatially repositioning the location of the surgical tool. According to these instructions, only allowed movements of the surgical tool will be performed. Preventing restricted movements is performed by: detecting the location of the surgical tool; processing all current rules; analyzing the movement of the surgical tool and preventing the movement if the tool's movement is a restricted movement.

According to some embodiments, system merely alerts the physician of a restricted movement of at least one surgical tool (instead of preventing said restricted movement).

Alerting the physician of restricted movements (or, alternatively preventing a restricted movement) is performed by: detecting the location of the surgical tool; processing all current rules; analyzing the movement of the surgical tool and informing the surgeon (the user of the system) if the tool's movement is an allowed movement or a restricted movement.

Thus, according to a preferred embodiment of the present invention, if restricted movements are prevented, the same process (of detecting the location of the surgical tool; processing all current rules and analyzing the movement of the surgical tool) is followed except for the last movement, where the movement is prevented if the tool's movement is a restricted movement. The surgeon can also be informed that the movement is being prevented.

According to some embodiments, the above (alerting the physician and/or preventing the movement) is performed by detecting the location of the surgical tool and analyzing the surgical environment of the surgical tool. Following analysis of the surgical environment and detection of the location of the surgical tool, the system may assess all the risks which may follow a movement of the surgical tool in the predetermined direction. Therefore, each location in the surgical environment has to be analyzed so that any possible movement of the surgical tool will be classified as an allowed movement or a restricted movement.

According to some embodiments of the present invention, the location of each tool is determined using image processing means and determining in real-time what is the 3D spatial location of each tool. It should be understood that the above mentioned "tool" may refer to the any location on the tool. For example, it can refer to the tip of the same, the body of the same and any combination thereof.

The predetermined set of rules which are the essence of the present invention are configured to take into consideration all the possible factors which may be important during the surgical procedure. The predetermined set of rules may comprise the following rules or any combination thereof:
a. a route rule;
b. an environment rule;
c. an operator input rule;
d. a proximity rule;
e. a collision prevention rule;
f. a history based rule;
g. a tool-dependent allowed and restricted movements rule.
h. a most used tool rule;
i. a right tool rule;
j. a left tool rule;
k. a field of view rule;
l. a no fly zone rule;
m. an operator input rule;
n. a preferred volume zone rule;
o. a preferred tool rule;
p. a movement detection rule;
q. a maximum speed rule;
r. a fixed point rule;
s. a physical/virtual zoom rule; and
t. a virtual rotation of scene rule.

Thus, for example, the collision prevention rule defines a minimum distance below which two or more tools should not be brought together (i.e., there is minimum distance between two or more tools that should be maintained). If the movement of one tool will cause it to come dangerously close to another tool (i.e., the distance between them, after the movement, is smaller than the minimum distance defined by the collision prevention rule), the controller either alerts the user that the movement is a restricted movement or does not permit the movement.

It should be emphasized that all of the above (and the following disclosure) is enabled by constantly monitoring the surgical environment, and identifying and locating the 3D spatial location of each element/tool in the surgical environment.

The identification is provided by conventional means known to any skilled in the art (e.g., image processing, optical means etc.).

The following provides explanations for each of the above mentioned rules and its functions:

According to some embodiments, the route rule comprises a predefined route in which the at least one surgical tool is configured to move within the surgical environment; the allowed movements are movements in which the at least one surgical tool is located within the borders of the predefined route, and the restricted movements are movements in which the at least one surgical tool is located out of the borders of the predefined route. Thus, according to this embodiment, the route rule comprises a communicable database storing at least one predefined route in which the at least one surgical tool is configured to move within the surgical environment; the predefined route comprises n 3D spatial positions of the at least one surgical tool in the route; n is an integer greater than or equal to 2; allowed movements are movements in which the at least one surgical tool is located substantially in at least one of the n 3D spatial positions of the predefined route, and restricted movements are movements in which the location of the at least one surgical tool is substantially different from the n 3D spatial positions of the predefined route.

In other words, according to the route rule, each of the surgical tool's courses (and path in any surgical procedure) is stored in a communicable database. allowed movements are defined as movements in which the at least one surgical tool is located substantially in at least one of the stored routes; and restricted movements are movements in which the at least one surgical tool is in a substantially different location than any location in any stored route.

According to some embodiments, the environmental rule is configured to determine allowed and restricted movements according to hazards or obstacles in the surgical environment as received from an endoscope or other sensing means. Thus, according to this embodiment, the environmental rule comprises a comprises a communicable database; the communicable database is configured to received real-time images of the surgical environment and is configured to perform real-time image processing of the same and to determine the 3D spatial position of hazards or obstacles in the surgical environment; the environmental rule is configured to determine allowed and restricted movements according to hazards or obstacles in the surgical environment, such that restricted movements are movements in which at least one surgical tool is located substantially in at least one of the 3D spatial positions, and allowed movements are movements in which the location of at least one surgical tool is substantially different from the 3D spatial positions.

In other words, according to the environment rule, each element in the surgical environment is identified so as to establish which is a hazard or obstacle (and a path in any surgical procedure) and each hazard and obstacle (and path) is stored in a communicable database. restricted movements are defined as movements in which the at least one surgical tool is located substantially in the same location as that of the hazards or obstacles; and the allowed movements are movements in which the location of the at least one surgical tool is substantially different from that of all of the hazards or obstacles.

According to other embodiments, hazards and obstacles in the surgical environment are selected from a group consisting of tissues, surgical tools, organs, endoscopes and any combination thereof.

According to some embodiments, the operator input rule is configured to receive an input from the operator of the system regarding the allowed and restricted movements of the at least one surgical tool. Thus, according to this embodiment, the operator input rule comprises a communicable database; the communicable database is configured to receive an input from the operator of the system regarding allowed and restricted movements of the at least one surgical tool.

According to other embodiments, the input comprises n 3D spatial positions; n is an integer greater than or equal to 2; wherein at least one of which is defined as an allowed location and at least one of which is defined as a restricted location, such that the allowed movements are movements in which the at least one surgical tool is located substantially in at least one of the n 3D allowed spatial positions, and the restricted movements are movements in which the location of the at least one surgical tool is substantially different from the n 3D allowed spatial positions.

According to other embodiments, the input comprises at least one rule according to which allowed and restricted movements of the at least one surgical tool are determined, such that the spatial position of the at least one surgical tool is controlled by the controller according to the allowed and restricted movements.

According to other embodiments, the operator input rule can convert an allowed movement to a restricted movement and a restricted movement to an allowed movement.

According to some embodiments, the proximity rule is configured to define a predetermined distance between the at least one surgical tool and at least one another surgical tool; the allowed movements are movements which are within the range or out of the range of the predetermined distance, and the restricted movements which are out of the range or within the range of the predetermined distance; the allowed movements and the restricted movements are defined according to different ranges. Thus, according to this embodiment, the proximity rule is configured to define a predetermined distance between at least two surgical tools. In a preferred embodiment, the allowed movements are movements which are within the range of the predetermined distance, while the restricted movements which are out of the range of the predetermined distance. In another preferred embodiment, the allowed movements are movements which are out of the range of the predetermined distance, while the restricted movements are within the range of the predetermined distance It should be pointed out that the above mentioned distance can be selected from the following:
(a) the distance between the tip of the first tool and the tip of the second tool;
(b) the distance between the body of the first tool and the tip of the second tool;
(c) the distance between the body of the first tool and the body of the second tool;
(d) the distance between the tip of the first tool and the body of the second tool; and any combination thereof.

According to some embodiments, the proximity rule is configured to define a predetermined angle between at least three surgical tools; allowed movements are movements which are within the range or out of the range of the predetermined angle, and restricted movements are movements which are out of the range or within the range of the predetermined angle.

According to some embodiments, the collision prevention rule is configured to define a predetermined distance between the at least one surgical tool and an anatomical element within the surgical environment (e.g. tissue, organ, another surgical tool or any combination thereof); the allowed movements are movements which are in a range that is larger than the predetermined distance, and the restricted movements are movements which is in a range that is smaller than the predetermined distance.

According to some embodiments, the anatomical element is selected from a group consisting of tissue, organ, another surgical tool or any combination thereof.

According to some embodiments, the surgical tool is an endoscope. The endoscope is configured to provide real-time images of the surgical environment.

According to some embodiments, the right tool rule is configured to determine the allowed movement of the endoscope according to the movement of a surgical tool in a specified position in relation to the endoscope, preferably positioned to right of the same. According to this rule, the tool which is defined as the right tool is constantly tracked by the endoscope. According to some embodiments, the right tool is defined as the tool positioned to the right of the endoscope; according to other embodiments, any tool can be defined as the right tool. An allowed movement, according to the right tool rule, is a movement in which the endoscope field of view is moved to a location substantially the same as the location of the right tool, thereby tracking the right tool. A restricted movement, according to the right tool rule, is a movement in which the endoscope field of view is moved to a location substantially different from the location of the right tool.

According to some embodiments, the left tool rule is configured to determine the allowed movement of the endoscope according to the movement of a surgical tool in a specified position in relation to the endoscope, preferably positioned to left of the same. According to this rule, the tool which is defined as the left tool is constantly tracked by the endoscope.

According to some embodiments, the left tool is defined as the tool positioned to the left of the endoscope; according to other embodiments, any tool can be defined as the left tool. An allowed movement, according to the left tool rule, is a movement in which the endoscope field of view is moved to a location substantially the same as the location of the left tool. A restricted movement, according to the left tool rule, is a movement in which the endoscope field of view is moved to a location substantially different from the location of the left tool.

According to some embodiments, the field of view rule is configured to define a field of view and maintain that field of view. The field of view rule is defined such that if the endoscope is configured to track a predetermined set of tools in a desired field of view, when one of those tools is no longer in the field of view, the rule instructs the endoscope to zoom out so as to reintroduce the tool into the field of view. Thus, according to this embodiment, the field of view rule comprises a communicable database comprising n 3D spatial positions; n is an integer greater than or equal to 2; the combination of all of the n 3D spatial positions provides a predetermined field of view; the field of view rule is configured to determine the allowed movement of the endoscope within the n 3D spatial positions so as to maintain a constant field of view, such that the allowed movements are movements in which the endoscope is located substantially in at least one of the n 3D spatial positions, and the restricted movements are movements in which the location of the endoscope is substantially different from the n 3D spatial positions.

Thus, according to some embodiments of the field of view rule, the field of view rule comprises a communicable database comprising n 3D spatial positions; n is an integer greater than or equal to 2; the combination of all of the n 3D spatial positions provides a predetermined field of view. The field of view rule further comprises a communicable database of m tools and the 3D spatial locations of the same, where m is an integer greater than or equal to 1 and where a tool can be a surgical tool, an anatomical element and any combination thereof. The combination of all of the n 3D spatial positions provides a predetermined field of view. The field of view rule is configured to determine allowed movement of the endoscope such that the m 3D spatial positions of the tools comprise at least one of the n 3D spatial positions of the field of view, and restricted movements are movements in which the 3D spatial position of at least one tool is substantially different from the n 3D spatial positions of the field of view.

According to some embodiments, the preferred volume zone rule comprises a communicable database comprising n 3D spatial positions; n is an integer greater than or equal to 2; the n 3D spatial positions provides the preferred volume zone; the preferred volume zone rule is configured to determine the allowed movement of the endoscope within the n 3D spatial positions and restricted movement of the endoscope outside the n 3D spatial positions, such that the allowed movements are movements in which the endoscope is located substantially in at least one of the n 3D spatial positions, and the restricted movements are movements in which the location of the endoscope is substantially different from the n 3D spatial positions. In other words, the preferred volume zone rule defines a volume of interest (a desired volume of interest), such that an allowed movement, according to the preferred volume zone rule, is a movement in which the endoscope (or any surgical tool) is moved to a location within the defined preferred volume. A restricted movement, according to the preferred volume zone rule, is a movement in which the endoscope (or any surgical tool) is moved to a location outside the defined preferred volume.

According to some embodiments, the preferred tool rule comprises a communicable database, the database stores a preferred tool; the preferred tool rule is configured to determine the allowed movement of the endoscope according to the movement of the preferred tool. In other words, the preferred tool rule defines a preferred tool (i.e., a tool of interest) that the user of the system wishes to track. An allowed movement, according to the preferred tool rule, is a movement in which the endoscope is moved to a location substantially the same as the location of the preferred tool. A restricted movement is a movement in which the endoscope is moved to a location substantially different from the location of the preferred tool. Thus, according to the preferred tool rule the endoscope constantly tracks the preferred tool, such that the field of view, as seen from the endoscope, is constantly the preferred tool. It should be noted that the user may define in said preferred tool rule to constantly tack the tip of said preferred tool or alternatively, the user may define in said preferred tool rule to constantly track the body or any location on the preferred tool.

According to some embodiments, the no fly zone rule is configured to define a restricted zone into which no tool (or alternatively no predefined tool) is permitted to enter. Thus, according to this embodiment, the no fly zone rule comprises a communicable database comprising n 3D spatial positions; n is an integer greater than or equal to 2; the n 3D spatial positions define a predetermined volume within the surgical environment; the no fly zone rule is configured to determine a restricted movement if the movement is within the no fly zone and an allowed movement if the movement is outside the no fly zone, such that restricted movements are movements in which the at least one surgical tool is located substantially in at least one of the n 3D spatial positions, and the allowed movements are movements in which the location of the at least one surgical tool is substantially different from the n 3D spatial positions.

According to some embodiments, the most used tool function is configured to define (either real-time, during the procedure or prior to the procedure) which tool is the most used tool (i.e., the tool which is moved the most during the procedure) and to instruct the maneuvering subsystem to constantly position the endoscope to track the movement of this tool. Thus, according to this embodiment, the most used tool rule comprises a communicable database counting the number of movements of each of the surgical tools; the most used tool rule is configured to constantly position the endoscope to track the movement of the surgical tool with the largest number of movements. In some embodiments of the most used tool function, the communicable database measures the amount of movement of each of the surgical tools; the most used tool rule is configured to constantly position the endoscope to track the movement of the surgical tool with the largest amount of movement.

According to some embodiments, the system is configured to alert the physician of a restricted movement of at least one surgical tool. The alert can be audio signaling, voice signaling, light signaling, flashing signaling and any combination thereof.

According to some embodiments, an allowed movement is one permitted by the controller and a restricted movement is one denied by the controller.

According to some embodiments, the operator input rule function is configured to receive an input from the operator of the system regarding allowed and restricted movements of the at least one surgical tool. In other words, the operator input rule function receives instructions from the physician as to what can be regarded as allowed movements and what are restricted movements.

According to some embodiments, the operator input rule is configured to convert an allowed movement to a restricted movement and a restricted movement to an allowed movement.

According to some embodiments, the history-based rule is configured to determine the allowed and restricted movements according to historical movements of the at least one surgical tool in at least one previous surgery. Thus, according to this embodiment, the history-based rule comprises a communicable database storing each 3D spatial position of each of the surgical tools, such that each movement of each surgical tool is stored; the history-based rule is configured to determine allowed and restricted movements according to historical movements of the at least one surgical tool, such that the allowed movements are movements in which the at least one surgical tool is located substantially in at least one of the 3D spatial positions, and the restricted movements are movements in which the location of the at least one surgical tool is substantially different from the n 3D spatial positions.

According to some embodiments, the tool-dependent allowed and restricted movements rule is configured to determine allowed and restricted movements according to predetermined characteristics of the surgical tool, where the predetermined characteristics of the surgical tool are selected from a group consisting of: physical dimensions, structure, weight, sharpness, and any combination thereof. Thus, according to this embodiment, the tool-dependent allowed and restricted movements rule comprises a communicable database; the communicable database is configured to store predetermined characteristics of at least one of the surgical tools; the tool-dependent allowed and restricted movements rule is configured to determine allowed and restricted movements according to the predetermined characteristics of the surgical tool.

According to some embodiments, the predetermined characteristics of the surgical tool are selected from a group consisting of: physical dimensions, structure, weight, sharpness, and any combination thereof.

According to some embodiments, the user can define, e.g., the structure of the surgical tool he wishes the endoscope to track. Thus, according to the tool-dependent allowed and restricted movements rule the endoscope constantly tracks the surgical tool having said predetermined characteristics as defined by the user.

According to some embodiments of the present invention, the movement detection rule comprises a communicable database comprising the real-time 3D spatial positions of each surgical tool; said movement detection rule is configured to detect movement of at least one surgical tool. When a change in the 3D spatial position of that surgical tool is received, allowed movements are movements in which the endoscope is re-directed to focus on the moving surgical tool.

According to some embodiments of the present invention, the system further comprises a maneuvering subsystem communicable with the controller. The maneuvering subsystem is configured to spatially reposition the at least one surgical tool during a surgery according to the predetermined set of rules.

According to some embodiments, the at least one location estimating means is at least one endoscope configured to acquire real-time images of a surgical environment within the human body for the estimation of the location of at least one surgical tool.

According to some embodiments, the location estimating means comprise at least one selected from a group consisting of optical imaging means, radio frequency transmitting and receiving means, at least one mark on at least one surgical tool and any combination thereof.

According to some embodiments, the at least one location estimating means is an interface subsystem between a surgeon and at least one surgical tool, the interface subsystem comprising (a) at least one array comprising N regular light sources or N pattern light sources, where N is a positive integer; (b) at least one array comprising M cameras, where M is a positive integer; (c) optional optical markers and means for attaching the optical markers to at least one surgical tool; and (d) a computerized algorithm operable via the controller, the computerized algorithm configured to record images received by each camera of each of the M cameras and to calculate therefrom the position of each of the tools, and further configured to provide automatically the results of the calculation to the human operator of the interface.

It is well known that surgery is a highly dynamic procedure with a constantly changing environment which depends on many variables. A non-limiting list of these variables includes, for example: the type of the surgery, the working space (e.g., with foreign objects, dynamic uncorrelated movements, etc), the type of tools used during the surgery, changing background, relative movements, dynamic procedures, dynamic input from the operator and the history of the patient. Therefore, there is need for a system which is able to integrate all the variables by weighting their importance and deciding to which spatial position the endoscope should be relocated.

The present invention can be also utilized to improve the interface between the operators (e.g., the surgeon, the operating medical assistant, the surgeon's colleagues, etc.). Moreover, the present invention can be also utilized to control and/or direct an automated maneuvering subsystem to focus the endoscope on an instrument selected by the surgeon, or to any other region of interest. This may be performed in order to estimate the location of at least one surgical tool during a surgical procedure.

The present invention also discloses a surgical tracking system which is configured to guide and relocate an endoscope to a predetermined region of interest in an automatic and/or a semi-automatic manner. This operation is assisted by an image processing algorithm(s) which is configured to analyze the received data from the endoscope in real time, and to assess the surgical environment of the endoscope.

According to an embodiment, the system comprises a "smart" tracking subsystem, which receives instructions from a maneuvering function f(t) (t is the time) as to where to direct the endoscope and which instructs the maneuvering subsystem to relocate the endoscope to the required area.

The maneuvering function f(t) receives, as input, output from at least two instructing functions $g_i(t)$, analyses their output and provides instruction to the "smart" tracking system (which eventually re-directs the endoscope).

According to some embodiments, each instructing function $g_i(t)$ is also given a weighting function, $\alpha_i(t)$.

The instructing functions $g_i(t)$ of the present invention are functions which are configured to assess the environment of the endoscope and the surgery, and to output data which guides the tracking subsystem for controlling the spatial position of the maneuvering subsystem and the endoscope. The instructing functions $g_i(t)$ may be selected from a group consisting of:
  a. a tool detection function $g_1(t)$;
  b. a movement detection function $g_2(t)$;
  c. an organ detection function $g_3(t)$;
  d. a collision detection function $g_4(t)$;
  e. an operator input function $g_5(t)$;
  f. a prediction function $g_6(t)$;
  g. a past statistical analysis function $g_7(t)$;
  h. a most used tool function $g_8(t)$;
  i. a right tool function $g_9(t)$;
  j. a left tool function $g_{10}(t)$;
  k. a field of view function $g_{11}(t)$;
  l. a preferred volume zone function $g_{12}(t)$;
  m. a no fly zone function $g_{13}(t)$;
  n. a proximity function $g_{14}(t)$;
  o. a tagged tool function $g_{15}(t)$;
  p. a preferred tool function $g_{16}(t)$; and
  q. a fixed point function $g_{17}(t)$.

Thus, for example, the maneuvering function f(t) receives input from two instructing functions: the collision detection function $g_4(t)$ (the function providing information whether the distance between two elements is smaller than a predetermined distance) and from the most used tool function $g_5(t)$ (the function counts the number of times each tool is moved during a surgical procedure and provides information as to whether the most moved or most used tool is currently moving). The output given from the collision detection function $g_4(t)$ is that a surgical tool is dangerously close to an organ in the surgical environment. The output given from the most used tool function $g_8(t)$ is that the tool identified statistically as the most moved tool is currently moving.

The maneuvering function f(t) then assigns each of the instructing functions with weighting functions $\alpha_i(t)$. For example, the most used tool function $g_5(t)$ is assigned with a greater weight than the weight assigned to the collision detection function $g_4(t)$.

After the maneuvering function f(t) analyses the information received from the instructing functions $g_i(t)$ and the weighting functions $\alpha_i(t)$ of each, the same outputs instructions to the maneuvering subsystem to re-direct the endoscope (either to focus on the moving tool or on the tool approaching dangerously close to the organ).

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

According to some embodiments, the surgical tracking subsystem comprises:
  a. at least one endoscope configured to acquire real-time images of a surgical environment within the human body;
  b. a maneuvering subsystem configured to control the spatial position of the endoscope during the laparoscopic surgery; and, c. a tracking subsystem in communication with the maneuvering subsystem, configured to control the maneuvering subsystem so as to direct and modify the spatial position of the endoscope to a region of interest.

According to this embodiment, the tracking subsystem comprises a data processor. The data processor is configured to perform real-time image processing of the surgical environment and to instruct the maneuvering subsystem to modify the spatial position of the endoscope according to input received from a maneuvering function f(t); the maneuvering function f(t) is configured to (a) receive input from at least two instructing functions $g_i(t)$, where i is 1, . . . , n and n≥2 and where t is time; i and n are integers; and (b) to output instructions to the maneuvering subsystem based on the input from the at least two instructing functions $g_i(t)$, so as to spatially position the endoscope to the region of interest.

According to some embodiments, the tool detection function $g_1(t)$ is configured to detect tools in the surgical environment. According to this embodiment, the tool detection function is configured to detect surgical tools in the surgical environment and to output instructions to the tracking subsystem to instruct the maneuvering subsystem to direct the endoscope to the detected surgical tools.

According to some embodiments, the functions $g_i(t)$ may rank the different detected areas in the surgical environment according to a ranking scale (e.g., from 1 to 10) in which prohibited areas (i.e., areas which are defined as area to which the surgical tools are forbidden to 'enter) receive the lowest score (e.g., 1) and preferred areas (i.e., areas which are defined as area in which the surgical tools should be maintained) receive the highest score (e.g., 10).

According to a preferred embodiment, one function $g_1(t)$ is configured to detect tools in the surgical environment and inform the maneuvering function f(t) if they are in preferred areas or in prohibited areas.

According to some embodiments, the movement detection function $g_2(t)$ comprises a communicable database comprising the real-time 3D spatial positions of each of the surgical tools in the surgical environment; means to detect movement of the at least one surgical tool when a change in the 3D spatial positions is received, and means to output instructions to the tracking subsystem to instruct the maneuvering subsystem to direct the endoscope to the moved surgical tool.

According to some embodiments, the organ detection function $g_3(t)$ is configured to detect physiological organs in the surgical environment and to classify the detected organs as prohibited areas or preferred areas. For example, if the operator instructs the system that the specific surgery is kidney surgery, the organ detection function $g_3(t)$ will classify the kidneys (or one kidney, if the surgery is specified to be on a single kidney) as a preferred area and other organs will be classified as prohibited areas. According to some embodiments, the organ detection function is configured to detect organs in the surgical environment and to output instructions to the tracking subsystem to instruct the maneuvering subsystem to direct the endoscope to the detected organs. According to some embodiments, the right tool function is configured to detect surgical tool positioned to right of the endoscope and to output instructions to the tracking subsystem to instruct the maneuvering system to constantly direct the endoscope on the right tool and to track the right tool.

According to some embodiments, the left tool function is configured to detect surgical tool positioned to left of the endoscope and to output instructions to the tracking subsystem to instruct the maneuvering system to constantly direct the endoscope on the left tool and to track the left tool.

According to some embodiments, the collision detection function $g_4(t)$ is configured to detect prohibited areas within the surgical environment so as to prevent collisions between the endoscope and the prohibited areas. For example, if the endoscope is located in a narrow area in which a precise movement of the same is preferred, the collision detection function $g_4(t)$ will detect and classify different areas (e.g., nerves, veins, walls of organs) as prohibited areas. Thus, according to this embodiment, the collision prevention function is configured to define a predetermined distance between the at least one surgical tool and an anatomical element within the surgical environment; and to output instructions to the tracking subsystem to instruct the maneuvering subsystem to direct the endoscope to the surgical tool and the anatomical element within the surgical environment if the distance between the at least one surgical tool and an anatomical element is less than the predetermined distance. According to some embodiments of the present invention the anatomical element is selected from a group consisting of tissue, organ, another surgical tool and any combination thereof.

According to some embodiments, the operator input function $g_5(t)$ is configured to receive an input from the operator. The input can be, for example: an input regarding prohibited areas in the surgical environment, an input regarding allowed areas in the surgical environment, or an input regarding the region of interest and any combination thereof. The operator input function $g_5(t)$ can receive instructions from the operator before or during the surgery, and respond accordingly. According to some embodiments, the operator input function may further comprise a selection algorithm for selection of areas selected from a group consisting of: prohibited areas, allowed areas, regions of interest, and any combination thereof. The selection may be performed via an input device (e.g., a touch screen).

According to some embodiments, the operator input function $g_5(t)$ comprises a communicable database; the communicable database is configured to receive an input from the operator of the system; the input comprising n 3D spatial positions; n is an integer greater than or equal to 2; and to output instructions to the tracking subsystem to instruct the maneuvering subsystem to direct the endoscope to the at least one 3D spatial position received.

According to some embodiments, the prediction function $g_6(t)$ is configured to provide data regarding a surgical environment at a time $t_f > t_0$, wherein $t_0$ is the present time and $t_f$ is a future time. The prediction function $g_6(t)$ may communicate with a database which stores data regarding the environment of the surgery (e.g., the organs in the environment). This data may be used by the prediction function $g_6(t)$ for the prediction of expected or unexpected events or expected or unexpected objects during the operation. Thus, according to this embodiment, the prediction function $g_6(t)$ comprises a communicable database storing each 3D spatial position of each of surgical tool within the surgical environment, such that each movement of each surgical tool is stored; the prediction function is configured to (a) to predict the future 3D spatial position of each of the surgical tools (or each object); and, (b) to output instructions to the tracking subsystem to instruct the maneuvering subsystem to direct the endoscope to the future 3D spatial position.

According to some embodiments, the past statistical analysis function $g_7(t)$ is configured to provide data regarding the surgical environment or the laparoscopic surgery based on past statistical data stored in a database. The data regarding the surgical environment may be for example: data regarding prohibited areas, data regarding allowed areas, data regarding the region of interest and any combination thereof. Thus, according to this embodiment, the past statistical analysis function $g_6(t)$ comprises a communicable database storing each 3D spatial position of each of surgical tool within the surgical environment, such that each movement of each surgical tool is stored; the past statistical analysis function $g_6(t)$ is configured to (a) perform statistical analysis on the 3D spatial positions of each of the surgical tools in the past; and, (b) to predict the future 3D spatial position of each of the surgical tools; and, (c) to output instructions to the tracking subsystem to instruct the maneuvering subsystem to direct the endoscope to the future 3D spatial position. Thus, according to the past statistical analysis function $g_7(t)$, the past movements of each tool are analyzed and, according to this analysis, a prediction of the tool's next move is provided.

According to some embodiments, the most used tool function $g_8(t)$ comprises a communicable database counting the amount of movement of each surgical tool located within the surgical environment; the most used tool function is configured to output instructions to the tracking subsystem to instruct the maneuvering subsystem to direct the endoscope to constantly position the endoscope to track the movement of the most moved surgical tool. The amount of movement of a tool can be defined as the total number of movements of that tool or the total distance the tool has moved.

According to some embodiments, the right tool function $g_9(t)$ is configured to detect at least one surgical tool in a specified position in relation to the endoscope, preferably positioned to right of the endoscope and to output instructions to the tracking subsystem to instruct the maneuvering subsystem to constantly direct the endoscope to the right tool and to track the same. According to preferred embodiments, the right tool is defined as the tool positioned to the right of the endoscope; according to other embodiments, any tool can be defined as the right tool.

According to some embodiments, the left tool function $g_{10}(t)$ is configured to detect at least one surgical tool in a specified position in relation to the endoscope, preferably positioned to left of the endoscope and to output instructions to the tracking subsystem to instruct the maneuvering subsystem to constantly direct the endoscope to the left tool and to track the same. According to preferred embodiments, the left tool is defined as the tool positioned to the left of the endoscope; according to other embodiments, any tool can be defined as the left tool.

According to some embodiments, the field of view function $g_{11}(t)$ comprises a communicable database comprising n 3D spatial positions; n is an integer greater than or equal to 2; the combination of all of the n 3D spatial positions provides a predetermined field of view; the field of view function is configured to output instructions to the tracking subsystem to instruct the maneuvering subsystem to direct the endoscope to at least one 3D spatial position substantially within the n 3D spatial positions so as to maintain a constant field of view.

According to some embodiments, the preferred volume zone function $g_{12}(t)$ comprises a communicable database comprising n 3D spatial positions; n is an integer greater than or equal to 2; the n 3D spatial positions provide the preferred volume zone; the preferred volume zone function $g_{12}(t)$ is configured to output instructions to the tracking subsystem to instruct the maneuvering subsystem to direct the endoscope to at least one 3D spatial position substantially within the preferred volume zone.

According to some embodiments, the no fly zone function $g_{13}(t)$ comprises a communicable database comprising n 3D spatial positions; n is an integer greater than or equal to 2; the n 3D spatial positions define a predetermined volume within the surgical environment; the no fly zone function $g_{13}(t)$ is configured to output instructions to the tracking subsystem to instruct the maneuvering subsystem to direct the endoscope to at least one 3D spatial position substantially different from all the n 3D spatial positions.

According to some embodiments, the proximity function $g_{14}(t)$ is configured to define a predetermined distance between at least two surgical tools; and to output instructions to the tracking subsystem to instruct the maneuvering subsystem to direct the endoscope to the two surgical tools if the distance between the two surgical tools is less than or if it is greater than the predetermined distance.

According to some embodiments, the proximity function $g_{14}(t)$ is configured to define a predetermined angle between at least three surgical tools; and to output instructions to the tracking subsystem to instruct the maneuvering subsystem to direct the endoscope to the three surgical tools if the angle between the two surgical tools is less than or if it is greater than the predetermined angle.

According to some embodiments, the preferred volume zone function comprises a communicable database comprising n 3D spatial positions; n is an integer greater than or equals to 2; the n 3D spatial positions provides the preferred volume zone; the preferred volume zone function is configured to output instructions to the tracking subsystem to instruct the maneuvering system to direct the endoscope to the preferred volume zone.

According to some embodiments, the field of view function comprises a communicable database comprising n 3D spatial positions; n is an integer greater than or equals to 2; the combination of all of the n 3D spatial positions provides a predetermined field of view; the field of view function is configured to output instructions to the tracking subsystem to instruct the maneuvering system to direct the endoscope to at least one 3D spatial position substantially within the n 3D spatial positions so as to maintain a constant field of view.

According to some embodiments, the no fly zone function comprises a communicable database comprising n 3D spatial positions; n is an integer greater than or equals to 2; the n 3D spatial positions define a predetermined volume within the surgical environment; the no fly zone function is configured to output instructions to the tracking subsystem to instruct the maneuvering system to direct the endoscope to at least one 3D spatial position substantially different from all the n 3D spatial positions.

According to some embodiments, the most used tool function comprises a communicable database counting the amount of movement of each surgical tool located within the surgical environment; the most used tool function is configured to output instructions to the tracking subsystem to instruct the maneuvering subsystem to direct the endoscope to constantly position the endoscope to track the movement of the most moved surgical tool.

According to some embodiments, the prediction function $g_6(t)$ is configured to provide data regarding a surgical environment in a time $t_f > t$, wherein t is the present time and $t_f$ is the future time. The prediction function $g_6(t)$ may communicate with a database which stores data regarding the environment of the surgery (e.g., the organs in the environment). This data may be used by the prediction function $g_6(t)$ for the prediction of expected or unexpected events or object during the operation. Thus, according to this embodiment, the prediction function comprises a communicable database storing each 3D spatial position of each of surgical tool within the surgical environment, such that each movement of each surgical tool is stored; the prediction function is configured to (a) to predict the future 3D spatial position of each of the surgical tools; and, (b) to output instructions to the tracking subsystem to instruct the maneuvering system to direct the endoscope to the future 3D spatial position.

According to some embodiments, the past statistical analysis function $g_7(t)$ is configured to provide data regarding the surgical environment or the laparoscopic surgery based on past statistical data stored in a database. The data regarding the surgical environment may be for example: data regarding prohibited areas, data regarding allowed areas, data regarding the region of interest. Thus, according to this embodiment, the past statistical analysis function comprises a communicable database storing each 3D spatial position of each of surgical tool within the surgical environment, such that each movement of each surgical tool is stored; the past statistical analysis function is configured to (a) statistical analyze the 3D spatial positions of each of the surgical tools in the past; and, (b) to predict the future 3D spatial position of each of the surgical tools; and, (c) to output instructions to the tracking subsystem to instruct the maneuvering system to direct the endoscope to the future 3D spatial position. Thus, according to the past statistical analysis function $g_7(t)$, the past movements of each tool are analyzed and according to this analysis a future prediction of the tool's next move is provided.

According to some embodiments, preferred tool function comprises a communicable database, the database stores a preferred tool; the preferred tool function is configured to output instructions to the tracking subsystem to instruct the maneuvering system to constantly direct the endoscope to the preferred tool, such that said endoscope constantly tracks said preferred tool.

Thus, according to the preferred tool function the endoscope constantly tracks the preferred tool, such that the field of view, as seen from the endoscope, is constantly maintained on said preferred tool. It should be noted that the user may define in said preferred tool function to constantly tack the tip of said preferred tool or alternatively, the user may define in said preferred tool function to constantly track the body or any location on the preferred tool.

According to some embodiments, the tagged tool function $g_{15}(t)$ comprises means configured to tag at least one surgical tool within the surgical environment and to output instructions to the tracking subsystem to instruct the maneuvering subsystem to constantly direct the endoscope to the tagged surgical tool. Thus, according to the tagged tool function the endoscope constantly tracks the preferred (i.e., tagged) tool, such that the field of view, as seen from the endoscope, is constantly maintained on said preferred (tagged) tool. It should be noted that the user may define in said tagged tool function to constantly tack the tip of said preferred (tagged) tool or alternatively, the user may define in said tagged tool function to constantly track the body or any location on the preferred (tagged) tool.

According to some embodiments, the means are configured to constantly tag the at least one of surgical tool within the surgical environment.

According to some embodiments, the preferred tool function $g_{16}(t)$ comprises a communicable database. The database stores a preferred tool; and the preferred tool function is configured to output instructions to the tracking subsystem to instruct the maneuvering subsystem to direct the endoscope to the preferred tool.

According to some embodiments, the fixed point function $g_{17}(t)$ is configured to determine a point fixed relative to either the maneuvering system coordinate system or to at least one object within the body cavity and to output instructions to the tracking subsystem to instruct the maneuvering subsystem to constantly direct the endoscope to fixed point and to track the same.

According to some embodiments, the system further comprises means configured to re-tag the at least one of the surgical tools until a desired tool is selected.

According to some embodiments, the system further comprises means configured to toggle the surgical tools. According to some embodiments, the toggling is performed manually or automatically.

According to some embodiments of the present invention, the weighting functions $\alpha_i(t)$ are time-varying functions (or constants), the value of which is determined by the operator or the output of the instructing functions $g_i(t)$. For example, if a specific function $g_i(t)$ detected an important event or object, its weighting functions $\alpha_i(t)$ may be adjusted in order to elevate the chances that the maneuvering function $f(t)$ will instruct the maneuvering subsystem to move the endoscope towards this important event or object.

According to some embodiments of the present invention, the tracking subsystem may implement various image processing algorithms which may also be algorithms that are well known in the art. The image processing algorithms may be for example: image stabilization algorithms, image improvement algorithms, image compilation algorithms, image enhancement algorithms, image detection algorithms, image classification algorithms, image correlations with the cardiac cycle or the respiratory cycle of the human body, smoke reduction algorithms, vapor reduction algorithms, steam reduction algorithms and any combination thereof. Smoke, vapor and steam reduction algorithms may be needed as it is known that, under certain conditions, smoke, vapor or steam may be emitted by or from the endoscope. The image processing algorithm may also be implemented and used to analyze 2D or 3D representations which may be rendered from the real-time images of the surgical environment.

According to some embodiments, the endoscope may comprise an image acquisition device selected from a group consisting of: a camera, a video camera, an electromagnetic sensor, a computer tomography imaging device, a fluoroscopic imaging device, an ultrasound imaging device, and any combination thereof.

According to some embodiments, the system may also comprise a display configured to provide input or output to the operator regarding the operation of the system. The display may be used to output the acquired real-time images of a surgical environment with augmented reality elements. The display may also be used for the definition of the region of interest by the operator.

According to some embodiments, the endoscope may be controlled be an endoscope controller for performing operations such as: acquiring the real-time images and zooming-in to a predetermined area. For example, the endoscope controller may cause the endoscope to acquire the real-time images in correlation with the cardiac cycle or the respiratory cycle of a human body.

According to some embodiments, the data processor of the present invention may operate a pattern recognition algorithm for assisting the operation of the instructing functions $g_i(t)$. The pattern recognition algorithm may be used as part of the image processing algorithm.

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

The present invention further discloses a method for assisting an operator to perform a surgical procedure, comprising steps of:
  a. providing a surgical controlling system, comprising: (i) at least one surgical tool; (ii) at least one location estimating means; and (iii) a controller having a processing means communicable with a database;
  b. inserting the at least one surgical tool into a surgical environment of a human body;
  c. estimating the location of the at least one surgical tool within the surgical environment; and,
  d. controlling the spatial position of the at least one surgical tool within the surgical environment by means of the controller; wherein the step of controlling is performed by storing a predetermined set of rules in the database where the predetermined set of rules comprises allowed and restricted movements of the at least one surgical tool, such that the spatial position of the at least one surgical tool is controlled by the controller according to the allowed and restricted movements.

The present invention also discloses a method for assisting an operator to perform laparoscopic surgery on a human body. The method comprises steps of:
  a. providing a surgical tracking system, comprising: (i) at least one endoscope configured to acquire real-time images of a surgical environment within the human body; (ii) a maneuvering subsystem in communication with the endoscope; and (iii) a tracking subsystem in communication with the maneuvering subsystem, the tracking subsystem comprising a data processor;
  b. performing real-time image processing of the surgical environment; and
  c. controlling the maneuvering subsystem via the tracking subsystem, thereby directing and modifying the spatial position of the endoscope to a region of interest according to input received from a maneuvering function $f(t)$; the maneuvering function $f(t)$ being configured to (a) receive input from at least two instructing functions $g_i(t)$, where i is $1, \ldots, n$ and $n \geq 2$; where t is time; i and n are integers; and (b) to output instructions to the maneuvering subsystem based on the input from the at least two instructing functions $g_i(t)$, so as to spatially position the endoscope to the region of interest.

It should be emphasized that all of the above (and the following disclosure) is enabled by constantly monitoring and locating/identifying the 3D spatial location of each element/tool in the surgical environment.

The identification is provided by conventional means known to any skilled in the art (e.g., image processing, optical means etc.).

The present invention further discloses a surgical controlling system, comprising:
  a. at least one endoscope configured to provide real-time image of surgical environment of a human body;
  b. at least one processing means, configured to real time define n element within the real-time image of surgical environment of a human body; each of the elements is characterized by predetermined characteristics;
  c. image processing means in communication with the endoscope, configured to image process the real-time image and to provide real time updates of the predetermined characteristics; and
  d. a communicable database, in communication with the processing means and the image processing means, configured to store the predetermined characteristics and the updated characteristics;
  the system being configured to notify the operator if the updated characteristics are substantially different from the predetermined characteristics.

Thus, according to this embodiment, each element in the surgical environment is characterized. The characteristics are constantly monitored. If the characteristics change substantially, the system notifies the user.

For example, the element that is monitored could be an organ and the characteristic being monitored is its contours. Once the contours have significantly changed (which could imply that the organ has been e.g., carved) the system alerts the user.

It should be emphasized that all of the above is enabled by constantly monitoring and locating/identifying the 3D spatial location of each element/tool in the surgical environment.

The identification is provided by conventional means known to any skilled in the art (e.g., image processing, optical means etc.).

According to some embodiments, the predetermined characteristics are selected from a group consisting of: color of the element, 3D spatial location of the element, contours of the element, and any combination thereof.

According to some embodiments, the system additionally comprises at least one surgical tool configured to be inserted into a surgical environment of a human body for assisting a surgical procedure.

According to some embodiments, the system additionally comprises at least one location estimating means configured to estimate the location of the at least one surgical tool.

According to some embodiments, the system additionally comprises a controller having a processing means communicable with a database, the controller configured to control the spatial position of the at least one surgical tool.

The present invention further provides a method for controlling surgery, comprising steps of:
  a. obtaining a system comprising:
    i. at least one endoscope configured to provide real-time image of a surgical environment in a human body;
    ii. at least one processing means, configured to define in real time n elements within the real-time image of the surgical environment of a human body, n is an integer greater than 0; each of the elements characterized by predetermined characteristics;
    iii. image processing means in communication with the endoscope, configured to process the real-time image and to provide real time updates of the predetermined characteristics; and
    iv. a communicable database, in communication with the processing means and the image processing means, configured to store the predetermined characteristics and the updated characteristics;
  b. providing a real-time image of a surgical environment in a human body;
  c. defining the n elements;
  d. characterizing each of the elements by the predetermined characteristics;
  e. providing a real-time update of the predetermined characteristics; and f. notifying the user if the updated characteristics are substantially different from the predetermined characteristics.

According to some embodiments, the predetermined characteristics are selected from a group consisting of: color of the element, 3D spatial location of the element, contours of the element and any combination thereof.

According to some embodiments, the method additionally comprises a step of providing at least one surgical tool configured to be inserted into a surgical environment of a human body for assisting a surgical procedure.

According to some embodiments, the method additionally comprises a step of providing at least one location estimating means configured to estimate the location of the at least one surgical tool.

According to some embodiments, the method additionally comprises a step of providing a controller having a processing means communicable with a database, the controller configured to control the spatial position of the at least one surgical tool.

According to some embodiments, the system of the present invention additionally comprises an image processing unit. According to some embodiments, the image processing unit is configured to reduce 'noise' from the received image by reducing the visibility in the image of the smoke caused by e.g., coagulation. According to some embodiments, the image processing unit is configured to reduce 'noise' from the received image by reducing the visibility in the image of vapor or steam accumulated on the endoscope.

According to some embodiments, the right tool function is configured to instruct the maneuvering subsystem to constantly position the endoscope to track the movement of the right tool (i.e., the tool positioned to the right of the endoscope).

According to some embodiments, the left tool function is configured to instruct the maneuvering subsystem to constantly position the endoscope to track the movement of the left tool (i.e., the tool positioned to the left of the endoscope).

According to some embodiments, the field of view function is configured to instruct the maneuvering subsystem to constantly position the endoscope so as to maintain a constant field of view.

According to some embodiments, the no fly zone function is configured to define (either real-time, during the procedure or prior to the procedure) a no fly zone and to instruct the maneuvering subsystem to restrict entrance of the endoscope to the no fly zone.

According to some embodiments, the most used tool function is configured to define (either real-time, during the procedure or prior to the procedure) which tool is the most used tool (i.e., the tool which is moved the most during the procedure) and to instruct the maneuvering subsystem to constantly position the endoscope to track the movement of the most-used tool.

Predetermined manners of input maneuvering of a tool or other moving element can include, but are not limited to: shaking the tool or other moving element, moving a tool or other moving element in at least a portion of a circle, moving a tool or other moving element in at least a portion of an oval, moving a tool or other moving element in at least a portion of an ellipse, moving a tool or other moving element in a straight line, moving a tool or other moving element in a zigzag, rotating a tool or other moving element in a predetermined manner, translating a tool or other moving element in a predetermined manner, and any combination thereof.

Predetermined input positions of a tool or other moving element can include but are not limited to positioning the tool or other moving element at a predetermined location within a field of view, orienting the tool or other moving element at a predetermined angle within a field of view, and any combination thereof.

The predetermined location in the field of view can be an edge of the field of view or a predetermined region within the field of view.

Predetermined actions of a tool can include, but are not limited to operating a tool, activating a tool, articulating a tool, articulating an endoscope, zooming an endoscope, and any combination thereof.

Repositioning a tool typically refers to moving a tool from one position or orientation to at least one second position or orientation, where there is a predetermined difference between the first position and/or orientation and the second position and/or orientation. For non-limiting example, repositioning a cautery from the edge of a field of view to the center of the field of view can be associated with a command to turn the cautery on; to turn it off, reposition it from the center of the field of view to the edge.

Activation of a tool can include, but is not limited to: opening a tool, closing a tool, causing a tool to function (non-limiting examples include heating a cautery or ablator, starting a drill rotating, and starting flow of fluid via a tube or cannula), and stopping a tool from functioning.

Input protocols of movement are typically arbitrary, predefined movements, although they need not be. A non-limiting example of an arbitrary input protocol of movement is a clockwise circle of a tool tip to identify an input command for an inward zoom; the associated output protocol can comprise zooming the endoscope to increase magnification in a portion of the field of view. A non-limiting example of a non-arbitrary protocol of movement is movement that would bring a tool tip into dangerously close proximity to an organ; the output protocol of movement can comprise reducing the speed at which the tool tip moves, stopping movement of the tool tip, changing the direction of movement of the tool tip and any combination thereof.

Other input protocols include, but are not limited to, introducing a tool to the surgical environment, removing a tool from the surgical environment, and any combination thereof.

A non-limiting example of closing a tool is closing a grasper to retain a swab in position; an input protocol can be opening of the hand; the output protocol can be opening the grasper and releasing the swab from the grasper. In another example, an input protocol of movement of separating the hands indicates that an operator is going to work deeper in the tissue with the resulting output protocol of moving retractors to further open an incision. Similarly, an input protocol of movement of bringing the hands together can induce an output protocol of relaxing retractors so as to allow an incision to at least partially close.

In another non-limiting example, the input protocol comprises the input action of activation of a tool (such as, but not limited to, closing a grasper) with an associated output protocol of zooming the endoscope so that the image of tissue in the neighborhood of the grasper is magnified. A related input protocol can be opening of the grasper, with an associated output protocol of zooming outward to give an overview of the region.

The following figures provide examples of several of the above mentioned rules and functions.

Reference is made now to FIG. 1, which is a general schematic view of a specific embodiment of a surgical tracking system 100. In this figure are illustrated surgical instruments 17b and 17c and an endoscope 21 which may be maneuvered by means of maneuvering subsystem 19 according to the instructions received from a tracking subsystem operable by computer 15.

According to some embodiments of the present invention as defined in the above, the user may define the field of view function as constantly monitoring at least one of surgical instruments 17b and 17c.

According to this embodiment, the surgical tracking system 100 may also comprise one or more button operated wireless transmitters 12a, which transmit, upon activation, a single code wave 14 through aerial 13 to connected receiver 11 that produces a signal processed by computer 15, thereby directing and modifying the spatial position of endoscope 21 to the region of interest, as defined by the field of view function.

Alternatively, according to the proximity rule, if the distance between the surgical instruments 17b and 17c is smaller than a predetermined distance (as defined by the collision prevention rule), the system alerts the user that any movement of either one of the surgical instruments 17b and 17c that will reduce the distance is a restricted movement.

Figure 2:
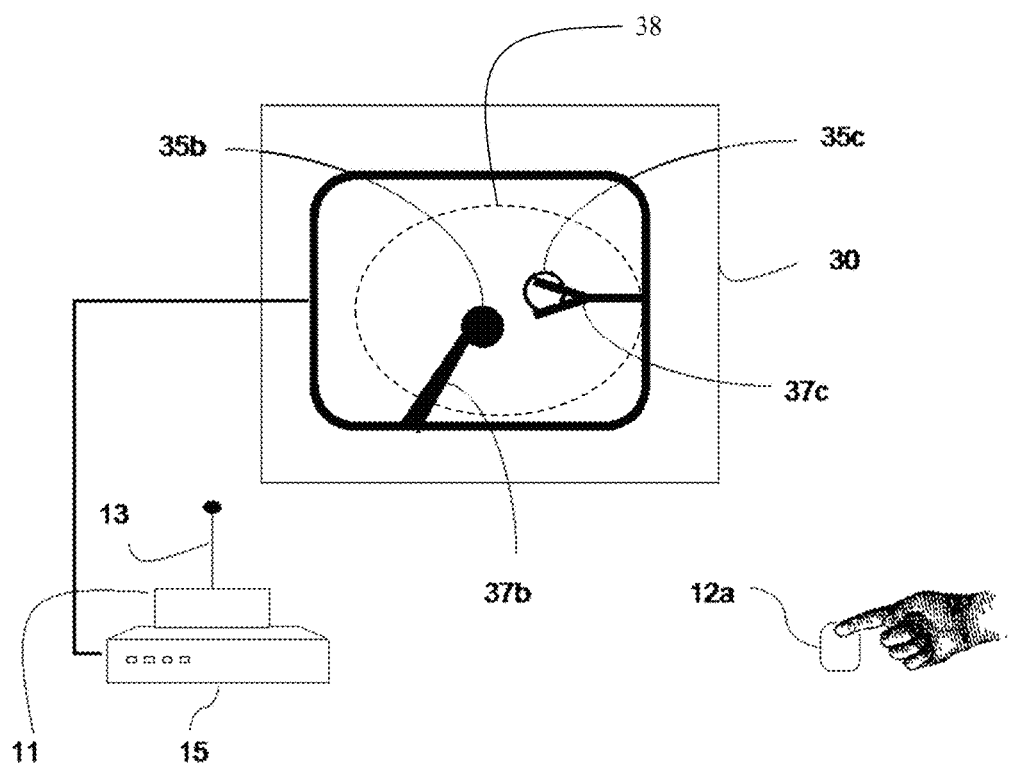

Reference is made now to FIG. 2, which schematically illustrates the operation of the present invention. According to this figure, the system of the present invention comprises a display 30 in which the overall procedure is presented to the operator. In this figure an endoscope is automatically spatially repositioned towards a region of interest 38.

The region of interest to which the endoscope is repositioned comprises tools 37b and 37c, which are automatically detected by the tracking subsystem (not shown) of computer 15. According to some embodiments, the repositioning of the endoscope may be automatic or semi-automatic. For example, according to FIG. 2, a light depression of the button on generic code-emitting wireless transmitter 12a causes transmission of a code that is received by receiver aerial 13 communicated through connected receiver 11 to computer 15. This operation causes the endoscope of the present invention to be spatially repositioned to the predefined region of interest (e.g., the location in which the working tools are located). According to this embodiment of the present invention, the operator may define the region of interest as the region in which a tip 35b of tool 37b is found.

According to some embodiments, the operator can define one of the surgical instruments 17b and 17c as a preferred tool. Thus, according to the preferred tool rule, the endoscope will constantly monitor and track the body of the selected tool. According to some embodiments, the user can define the preferred tool rule to constantly reposition the endoscope on the tip of the same (see tip 35b in FIG. 2).

According to the embodiment illustrated in FIG. 2, the activation of the system is provided by a button that signals to the system that it is to be activated.

According to some embodiments of the present invention, the button can be coupled to the desired tool to be monitored, such that the endo scope will monitor the tool to which the button is coupled (and from which signal 12a is emitted).

Referring again to FIG. 2, once a region of interest has been defined, the tracking subsystem is configured to look for tip 35b within the region of interest by performing image processing. When tip 35b is not detected by the tracking subsystem, the system can move the endoscope in a forward direction along a predefined track. When tip 35b is detected by the tracking subsystem, the endoscope automatically focuses of the region of interest.

While performing the surgery, the surgeon often changes the position of his tools and even their insertion point. In order to realize a position and range system, many well-known technologies may be used. For example, the tools may be equipped with switches. If the switches emit wireless signals, then an array of antennas may be used to compare the power of the signal received at each antenna in order to determine the angle of the switch and its approximate range to the camera holder mechanism. If the switch emits ultrasound then ultrasound-sensitive microphones can be used to triangulate the position of the switch. The same is true for a light-emitting switch. In a preferred embodiment of the invention, a single wireless emission code is utilized and choice is achieved by a visible graphic representation on a conventional viewing screen.

In another preferred embodiment, each instrument is fitted with a unique code wireless transmitter, and selection is achieved by depressing its button.

According to some embodiments, the tracking subsystem of the present invention may be used in any conventional camera-assisted laparoscopic surgery system which comprises an endoscope. Upon depression of at least one button on a transmitter for activating the tracking subsystem, either a generic or a unique code is transmitted to a receiving device connected to a computer that instructs the maneuvering subsystem to reposition the endoscope to a region of interest.

For example, the system of the present invention may be used to allow an operator (e.g., a surgeon) to present the surgical instrument to surgical colleagues and staff. By identifying the surgical instrument via the tracking subsystem, the endoscope directs the view to the predefined region of interest.

According to some embodiments, the tracking subsystem may identify a surgical tool after characterization of the same prior to the surgery. The characteristics of the surgical tool may be stored in a database for further use in the image processing algorithm. Upon depression of at least one button, the tracking subsystem may instruct the maneuvering subsystem to move the endoscope so as to achieve the desired focus on a specific region of interest.

The device of the present invention has many technological advantages, among them:
 Simplifying the communication interface between surgeon and mechanical assistants.
 Seamless interaction with conventional computerized automated endoscope systems.
 Simplicity of construction and reliability.
 User-friendliness.

Additional features and advantages of the invention will become apparent from the following drawings and description.

To improve the control of the endoscope, the system of the present invention comprises a maneuvering subsystem. Many maneuvering systems are known in the art and many of them have several degrees of freedom:
(a) one degree of freedom enables the system to move the endoscope or laparoscope forward and backwards;
(b) another degree of freedom enables the system to move the endoscope or laparoscope in a zoom movement i.e. in and out of the patient's body through the penetration point;
(c) another degree of freedom enables the system to move the endoscope or laparoscope to the right and left;
(d) another degree of freedom enables the system to fine tune endoscope or laparoscope movements to the right and to the left;

(e) another degree of freedom enables the system to fine tune endoscope or laparoscope movements forward and backwards; and
(f) another degree of freedom enables the system to rotate the camera with respect to the endoscope's long axis. This degree of freedom is necessary to keep the horizon of the image from changing when using an endoscope with "angled edge".

Such maneuvering systems are utilized by the present invention so as to reposition the endoscope to the desired location.

The present invention is utilized to improve upon the interface between surgeon and automated assistants by communicating the surgeon's current instrument of choice, supplying location data to the image processing computing software, thereby directing the endoscope to focus on that choice. The technology relies on marrying a conventional laparoscopic system with data obtained from e.g., small RF transmitters attached to a surgical tool or, alternatively, data obtained from light emitters (e.g., LED bulbs) attached to a surgical tool.

It will be apparent to one skilled in the art that there are several embodiments of the invention that differ in details of construction, without affecting the essential nature thereof, and therefore the invention is not limited by that which is illustrated in the figures and described in the specification, but only as indicated in the accompanying claims, with the proper scope determined only by the broadest interpretation of the claims.

Figure 3A:
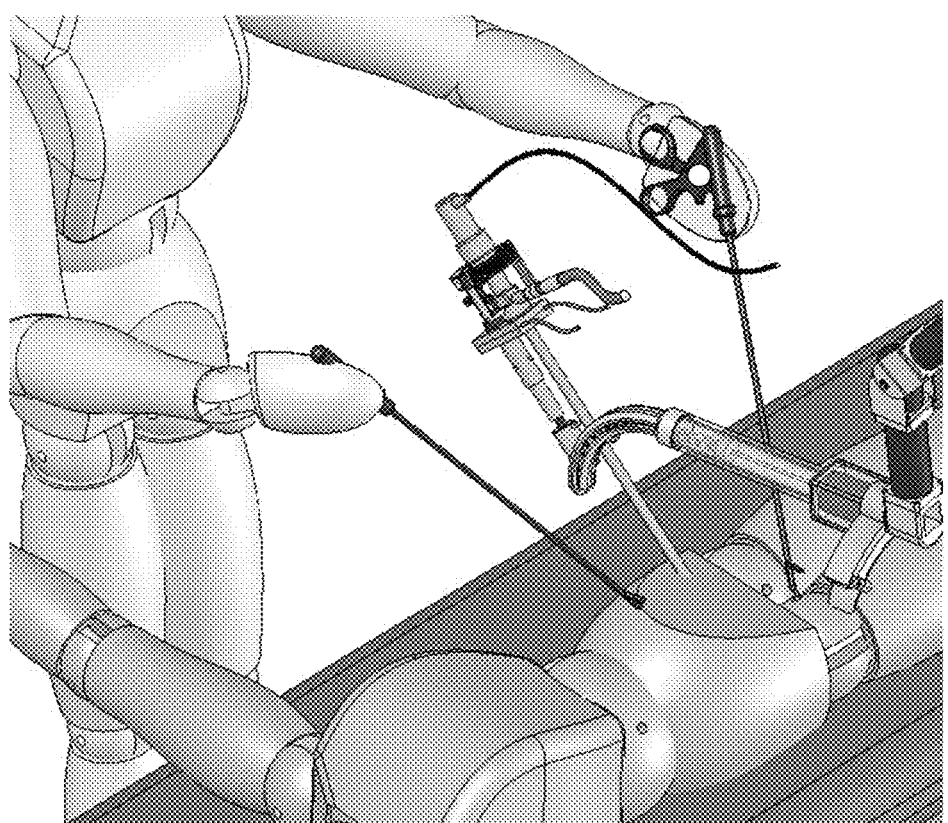
FIG. 3A shows an example of using the location system in abdominal laparoscopic surgery.

FIG. 3A shows an example of using the system of the present invention in abdominal laparoscopic surgery.

Figure 3B:
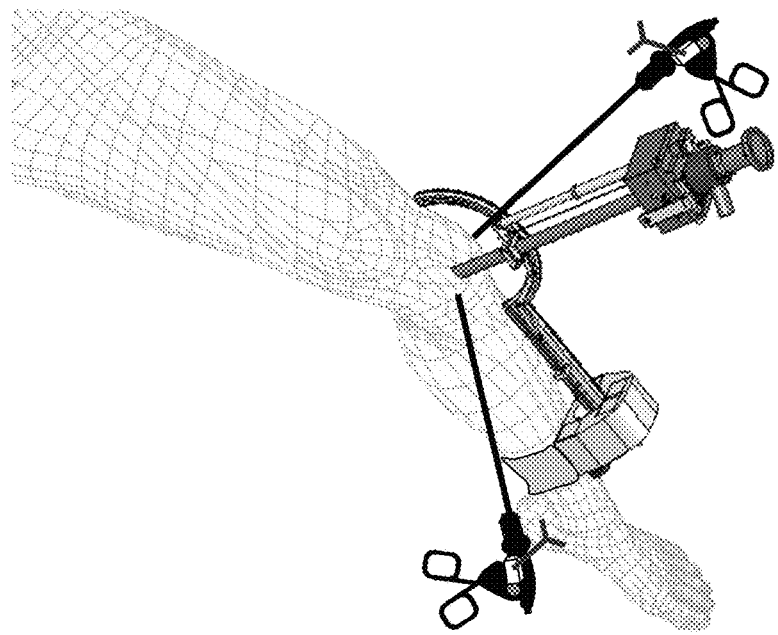
FIG. 3B shows an example of using the location system in knee endoscopic surgery.

FIG. 3B shows an example of using the system of the present invention in knee endoscopic surgery.

Figure 3C:
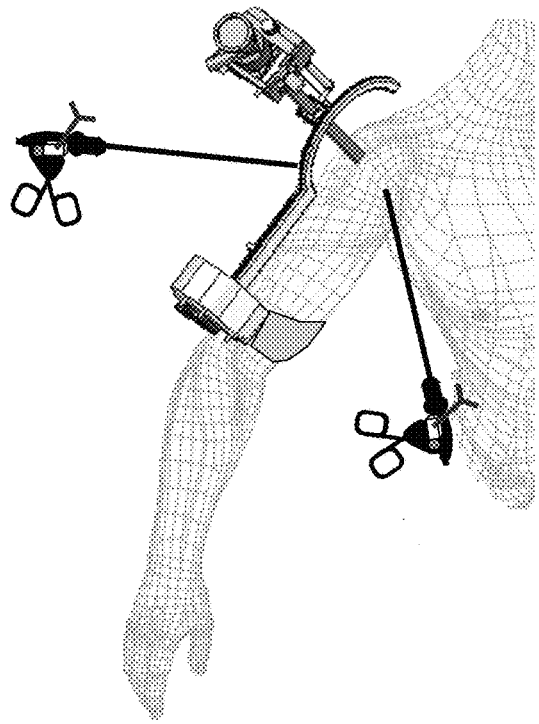
FIG. 3C shows an example of using the location system in shoulder endoscopic surgery.

Lastly, FIG. 3C shows an example of using the system of the present invention in shoulder endoscopic surgery.

EXAMPLES

Examples are given in order to demonstrate embodiments claimed in the present invention.

In the examples below, similar numbers refer to similar parts in all of the figures.

Example 1—Tracking System with Collision Avoidance System

Some embodiments of such a rule-based system will comprise the following set of commands:
Detection (denoted by Gd):
Gd1 Tool location detection function
Gd2 Organ (e.g. Liver) detection function
Gd3 Movement (vector) calculation and estimation function
Gd4 Collision probability detection function
Tool Instructions (denoted Gt):
Gt1 Move according to manual command
Gt2 Stop movement
The scenario—manual move command by the surgeon:
Locations Gd1($t$) and Gd2($t$) are calculated in real time at each time step (from an image or location marker).

Tool movement vector Gd3($t$) is calculated from Gd1($t$) as the difference between the current location and at least one previous location (probably also taking into account previous movement vectors).

The probability of collision—Gd4($t$)—is calculated, for example, from the difference between location Gd1 and location Gd2 (the smaller the distance, the closer the proximity and the higher the probability of collision), from movement vector Gd3($t$) indicating a collision, etc.

Tool Instructions Gt1 Weight function $\alpha_1(t)=1$ If Gt1($t$)<a predetermined threshold and 0 otherwise Tool Instructions Gt2 Weight function $\alpha_2(t)=1$ If Gt2($t$)>a predetermined threshold and 0 otherwise Tool Instructions=$\alpha_1(t)*Gt1+\alpha_2(t)*Gt2(t)$;

In reference to FIG. 4A-D, which shows, in a non-limiting manner, an embodiment of a tracking system and collision avoidance system. The system tracks a tool 310 and the liver 320, in order to determine whether a collision between the tool 310 and the liver 320 is possible within the next time step. FIGS. 4A and 4B show how the behavior of the system depends on the distance 330 between the tool 310 and the liver 320, while FIGS. 4C and 4D show how movement of the tool 310 affects the behavior. In FIG. 4A, the distance 330 between the tool 310 and the liver 320 is large enough that a collision is not possible in that time step. Since no collision is possible, no movement of the tool is commanded. In FIG. 4B, the distance 330 between the tool 310 and the liver 320 is small enough that a collision is likely. In the embodiment illustrated, a movement 340 is commanded to move the tool 310 away from the liver 320. In other embodiments, the system does not command movement 340; in such embodiments, the tool 310 will remain close to the liver 320. In yet other embodiments, the system warns/signals the operator that the tool is close to the liver, but does not command movement 340 away from the liver. Such a warning/signaling can be visual or aural, using any of the methods known in the art.

FIGS. 4C and 4D illustrate schematically the effect of the movement of tool 310 on the collision avoidance system. In FIGS. 4C and 4D, the tool 310 is close enough to the liver 320 that a collision between the two is possible. If the system tracked only the positions of the tool 310 and the liver 320, then motion of the tool 310 away from the liver 320 would be commanded. FIG. 4C illustrates the effect of a movement 350 that would increase the distance between tool 310 and liver 320. Since the movement 350 is away from liver 320, no collision is possible in this time step and no movement of the tool 310 is commanded.

In FIG. 4D, tool 310 is the same distance from liver 320 as in FIG. 4C. However, in FIG. 4D, the movement 350 of the tool 310 is toward the liver 320, making a collision between tool 310 and liver 320 possible. In some embodiments, a movement 340 is commanded to move the tool 310 away from the liver 320. In other embodiments, the system prevents movement 350, but does not command movement 340; in this embodiment the tool 310 will remain close to the liver 320. In yet other embodiments, the system warns the operator that move is restricted, but does not restrict movement 350 or command movement 340 away from the liver. Such a warning can be visual or aural, using any of the methods known in the art.

As a non-limiting example, in an operation on the liver, the collision detection function can warn the operator that a collision between a tool and the liver is likely but not prevent the collision. In an operation on the gall bladder, the collision detection function can prevent a collision between the tool and the liver, either by preventing the movement or by commanding a movement redirecting the tool away from the liver, Example 2—Tracking System with Soft
Control—Fast Movement when Nothing is Nearby,
Slow Movement when Something is Close Some embodiments of such rule-based system comprises the following set of commands:
Detection (denoted by Gd):
Main Tool location detection function (denoted by GdM);
Gd-tool1-K—Tool location detection function;
Gd-organ2-L—Organ (e.g. Liver) detection function;
Gd3 Main Tool Movement (vector) calculation and estimation function;
Gd4 Proximity probability detection function;
Tool Instructions (denoted Gt):
Gt1 Movement vector (direction and speed) according to manual command
The scenario—manual move command by the surgeon:
Locations GdM(t), Gd-tool1-K(t) and Gd-organ2-L(t) are calculated in real time at each time step (from image or location marker).
Main Tool Movement Vector Gd3($t$) is calculated per GdM (t) as the difference between the current location and at least one previous location (probably also taking into account previous movement vectors)
The proximity of the main tool to other tools—Gd4($t$)—is calculated, for example, as the smallest of the differences between the main tool location and the other tools' locations.
Tool Instructions Gt1 Weight function $\alpha_1(t)$ is proportional to tool proximity function Gd4($t$), the closer the tool the slower the movement so that, for example $\alpha_2(t)=Gd4/\text{maximum}(Gd4)$ or $\alpha_2(t)=\log(Gd4/\text{maximum}(Gd4))$ where maximum (Gd4) is the maximum distance which is likely to result in a collision given the distances, the speed of the tool and the movement vector.

Tool Instructions=$\alpha_1(t)*Gt1$.

Example 3—Tracking System with No-Fly
Rule/Function

In reference to FIG. 5A-D, which shows, in a non-limiting manner, an embodiment of a tracking system with no-fly rule. The system tracks a tool (310) with respect to a no-fly zone (460), in order to determine whether the tool will enter the no-fly zone (460) within the next time step. In this example, the no-fly zone (460) surrounds the liver.

Figure 5A:
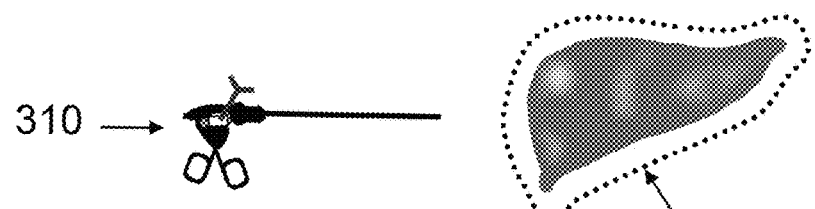
FIG. 5A-D schematically illustrates operation of an embodiment of a tracking system with no fly zone rule/function.
Figure 5B:
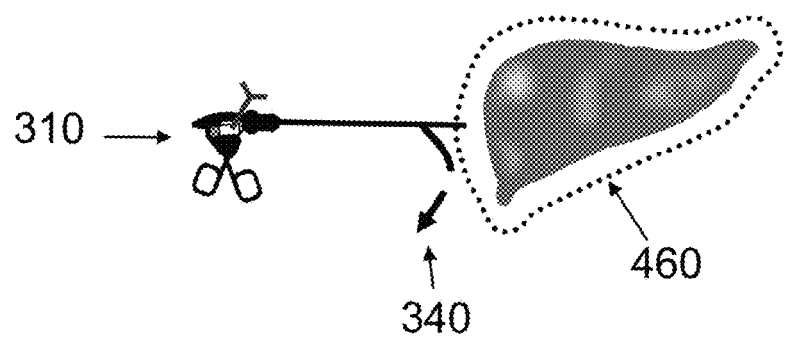
Figure 5C:
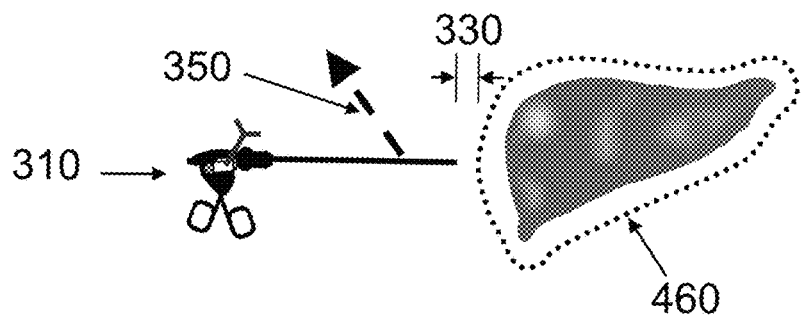
Figure 5D:
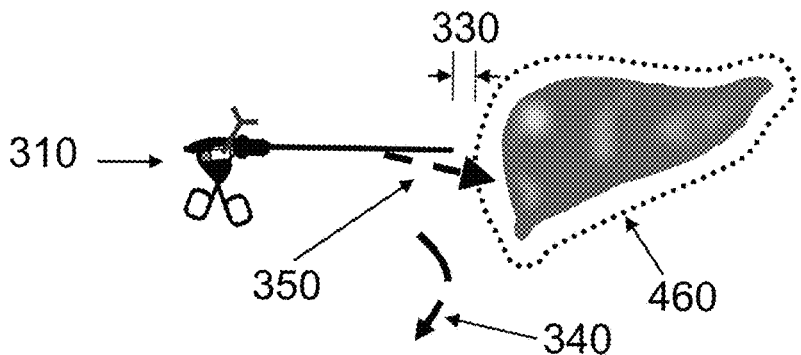

FIGS. 5A and 5B show how the behavior of the system depends on the location of the tool tip with respect to the no-fly zone, while FIGS. 5C and 5D show how movement of the tool affects the behavior.

In FIG. 5A, the tool 310 is outside the no-fly rule/function 460 and no movement of the tool is commanded. In FIG. 5B, the tool 310 is inside the no-fly zone 460.

The no-fly zone rule/function performs as follows:

In the embodiment illustrated, a movement 340 is commanded to move the tool 310 away from the no-fly zone 460. In other embodiments, the system prevents movement further into the no-fly zone (refers as movement 350, see FIG. 5D), but does not command movement 340; in such embodiments, the tool 310 will remain close to the no-fly zone 460.

In yet other embodiments, the system warns/signals the operator that the move is restricted, but does not restrict movement further into the no-fly zone or command movement 340 away from the no-fly zone 460. Such a warning/signaling can be visual or aural, using any of the methods known in the art.

FIGS. 5C and 5D illustrate schematically the effect of the tool's movement on operation of the no-fly zone rule/function. In FIGS. 5C and 5D, the tool 310 is close enough to the no-fly zone 460 (distance 330 is small enough) that it is possible for the tool to enter the no-fly zone during the next time step. FIG. 5C illustrates the effect of a movement 350 that would increase the distance between tool 310 and no-fly zone 460. Since the movement 350 is away from no-fly zone 460, no collision is possible in this time step and no movement of the tool 310 is commanded.

In FIG. 5D, tool 310 is the same distance from no-fly zone 460 as in FIG. 5C. However, in FIG. 5D, the movement 350 of the tool is toward no-fly zone 460, making it possible for tool 310 to enter no-fly zone 460. In the embodiment illustrated, a movement 340 is commanded to move the tool 310 away from the no-fly zone 460. In other embodiments, the system prevents movement 350, but does not command movement 340; in such embodiments, the tool 310 will remain close to the no-fly zone 460. In yet other embodiments, the system warns/signals the operator that the move is restricted, but does not restrict movement 350 or command movement 340 away from the no-fly zone rule/function 460. Such a warning/signaling can be visual or aural, using any of the methods known in the art.

Example 4—Tracking System with Preferred
Volume Zone Rule/Function

In reference to FIG. 6A-D, which shows, in a non-limiting manner, an embodiment of a tracking system with a preferred volume zone function/rule.

The system tracks a tool 310 with respect to a preferred volume zone (570), in order to determine whether the tool will leave the preferred volume (570) within the next time step.

Figure 6A:
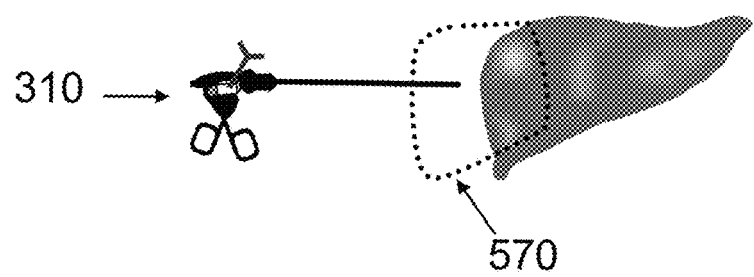
FIG. 6A-D schematically illustrates operation of an embodiment of a tracking system with preferred volume zone rule/function.
Figure 6B:
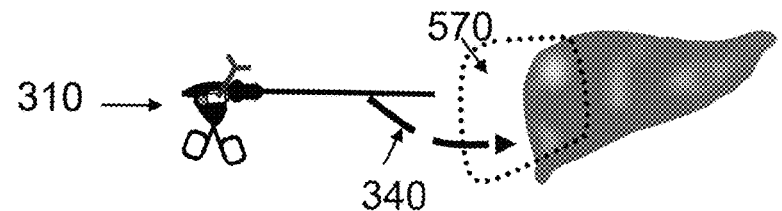

In this example, the preferred volume zone 570 extends over the right lobe of the liver. FIGS. 6A and 6B show how the behavior of the system depends on the location of the tool tip with respect to the preferred volume zone 570, while FIGS. 6C and 6D show how movement of the tool affects the behavior (i.e., the preferred volume zone rule/function).

In FIG. 6A, the tool 310 is inside the preferred volume zone 570 and no movement of the tool is commanded. In FIG. 6B, the tool 310 is outside the preferred volume zone 570.

In the embodiment illustrated, a movement 340 is commanded to move the tool 310 into the preferred volume zone 570. In other embodiments, the system does not command movement 340; in such embodiments, the tool 310 will remain close to but outside the preferred volume zone 570. In yet other embodiments, the system warns/signals the operator that the tool is outside the preferred volume zone 570, but does not move the tool. Such a warning/signaling can be visual or aural, using any of the methods known in the art.

Figure 6C:
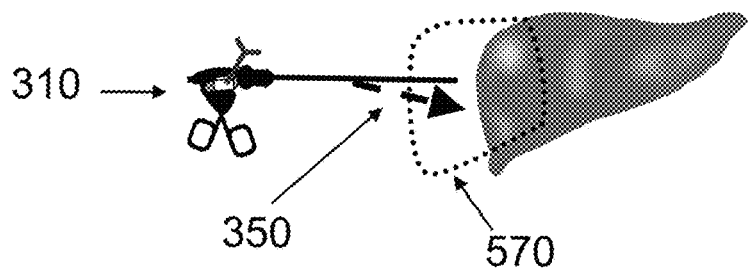
Figure 6D:
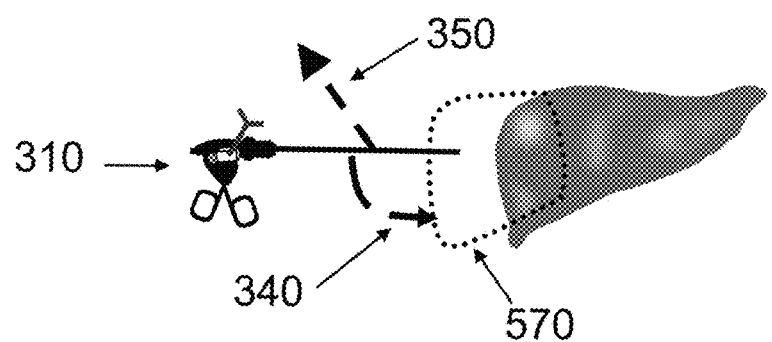

FIGS. 6C and 6D illustrate schematically the effect of the tool's movement on operation of the preferred volume rule/function. In FIGS. 6C and 6D, the tool 310 is close enough to the edge of preferred volume zone 570 that it is possible for the tool to leave the preferred volume zone during the next time step.

FIG. 6C illustrates the effect of a movement 350 that would take the tool 310 deeper into preferred volume zone

570. Since the movement 350 is into preferred volume 570, said movement is an allowed movement.

In FIG. 6D, the movement 350 of the tool is out of the preferred volume 570, making it possible for tool 310 to leave preferred volume 570.

According to the embodiment illustrated, a movement 340 is commanded to move the tool 310 into the preferred volume zone 570. In other embodiments, the system prevents movement 350, but does not command movement 340; in such embodiments, the tool 310 will remain within the preferred volume zone 570. In yet other embodiments, the system warns/signals the operator that the move is restricted, but does not restrict movement 350 or command movement 340 into the preferred volume zone 570. Such a warning/signaling can be visual or aural, using any of the methods known in the art.

Example 5—Organ/Tool Detection Function

Figure 7:
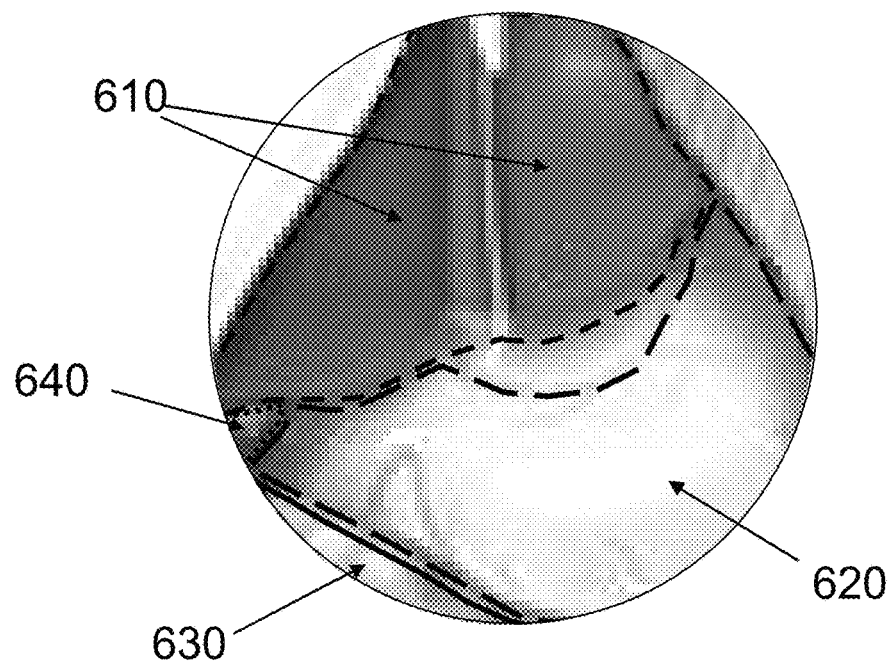
FIG. 7 schematically illustrates operation of an embodiment of the organ detection function/rule.

In reference to FIG. 7, which shows, in a non-limiting manner, an embodiment of an organ detection system (however, it should be noted that the same is provided for detection of tools, instead of organs).

For each organ, the 3D spatial positions of the organs stored in a database. In FIG. 7, the perimeter of each organ is marked, to indicate the edge of the volume of 3D spatial locations stored in the database.

In FIG. 7, the liver 610 is labeled with a short dashed line. The stomach 620 is labeled with a long-dashed line, the intestine 630 with a solid line and the gall bladder 640 is labeled with a dotted line.

In some embodiments, a label or tag visible to the operator is also presented. Any method of displaying identifying markers known in the art can be used. For non-limiting example, in an enhanced display, colored or patterned markers can indicate the locations of the organs, with the marker either indicating the perimeter of the organ or the area of the display in which it appears.

Example 6—Tool Detection Function

Figure 8:
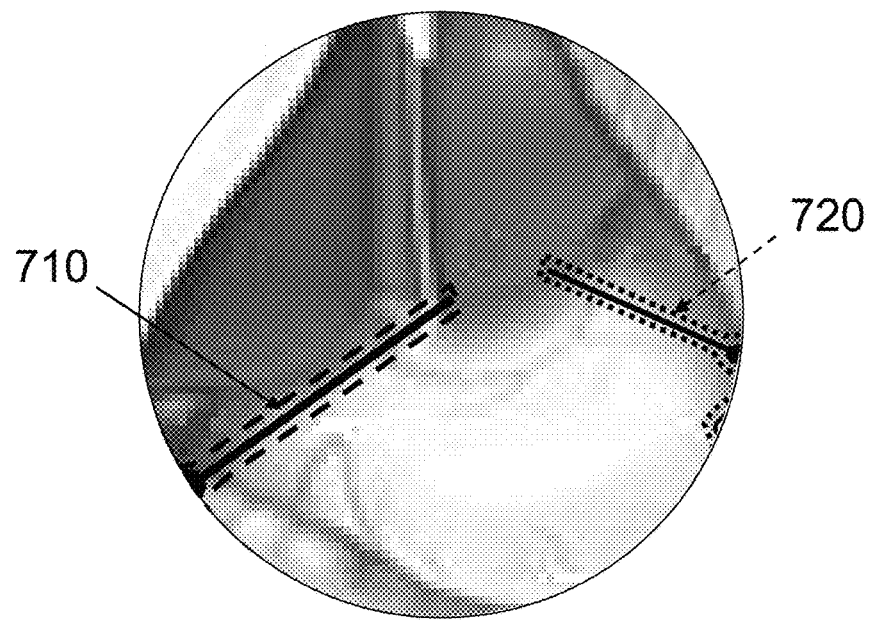
FIG. 8 schematically illustrates operation of an embodiment of the tool detection function/rule.

In reference to FIG. 8, which shows, in a non-limiting manner, an embodiment of a tool detection function. For each tool, the 3D spatial positions of the tools stored in a database. In FIG. 8, the perimeter of each tool is marked, to indicate the edge of the volume of 3D spatial locations stored in the database. In FIG. 8, the left tool 710 is labeled with a dashed line while the right tool 720 is labeled with a dotted line.

In some embodiments, a label or tag visible to the operator is also presented. Any method of displaying identifying markers known in the art can be used. For non-limiting example, in an enhanced display, colored or patterned markers can indicate the locations of the tools, with the marker either indicating the perimeter of the tool or the area of the display in which it appears.

Example 7—Movement Detection Function/Rule

Figure 9A:
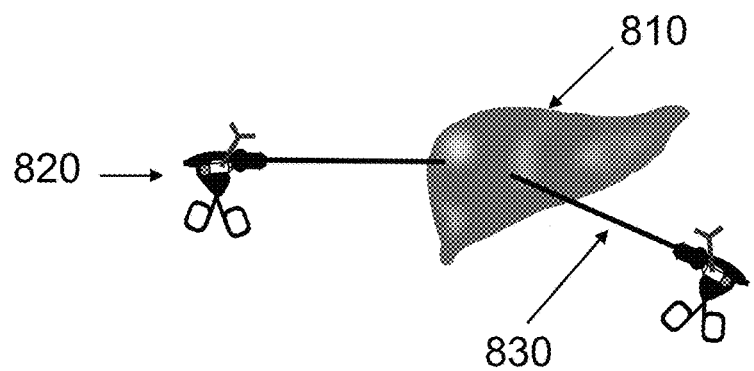
FIG. 9A-B schematically illustrates operation of an embodiment of the movement detection function/rule.
Figure 9B:
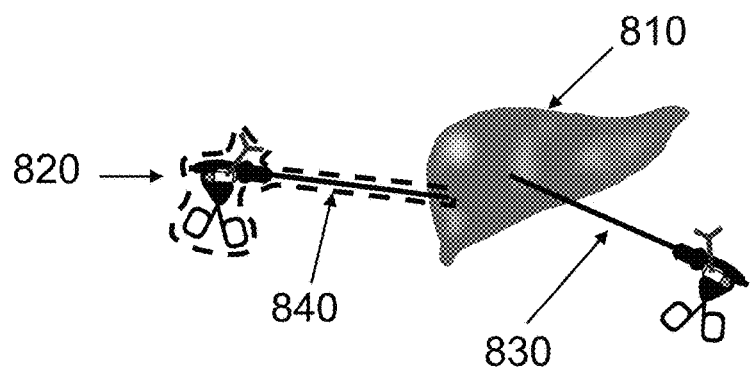

In reference to FIG. 9A-B, which shows, in a non-limiting manner, an embodiment of a movement detection function/rule. FIG. 9A schematically illustrates a liver 810, a left tool 820 and a right tool 830 at a time t. FIG. 9B schematically illustrates the liver 810, left tool 820 and right tool 830 at a later time t+Δt, where Δt is a small time interval. In this example, the left tool 820 has moved downward (towards the direction of liver 810) in the time interval Δt.

The system has detected movement of left tool 820 and labels it. This is illustrated schematically in FIG. 9B by a dashed line around left tool 820.

Example 8—Prediction Function

In reference to FIG. 10A-D, which shows, in a non-limiting manner, an embodiment of the above discussed prediction function.

Figures 10A, 10B, 10C, 10D:
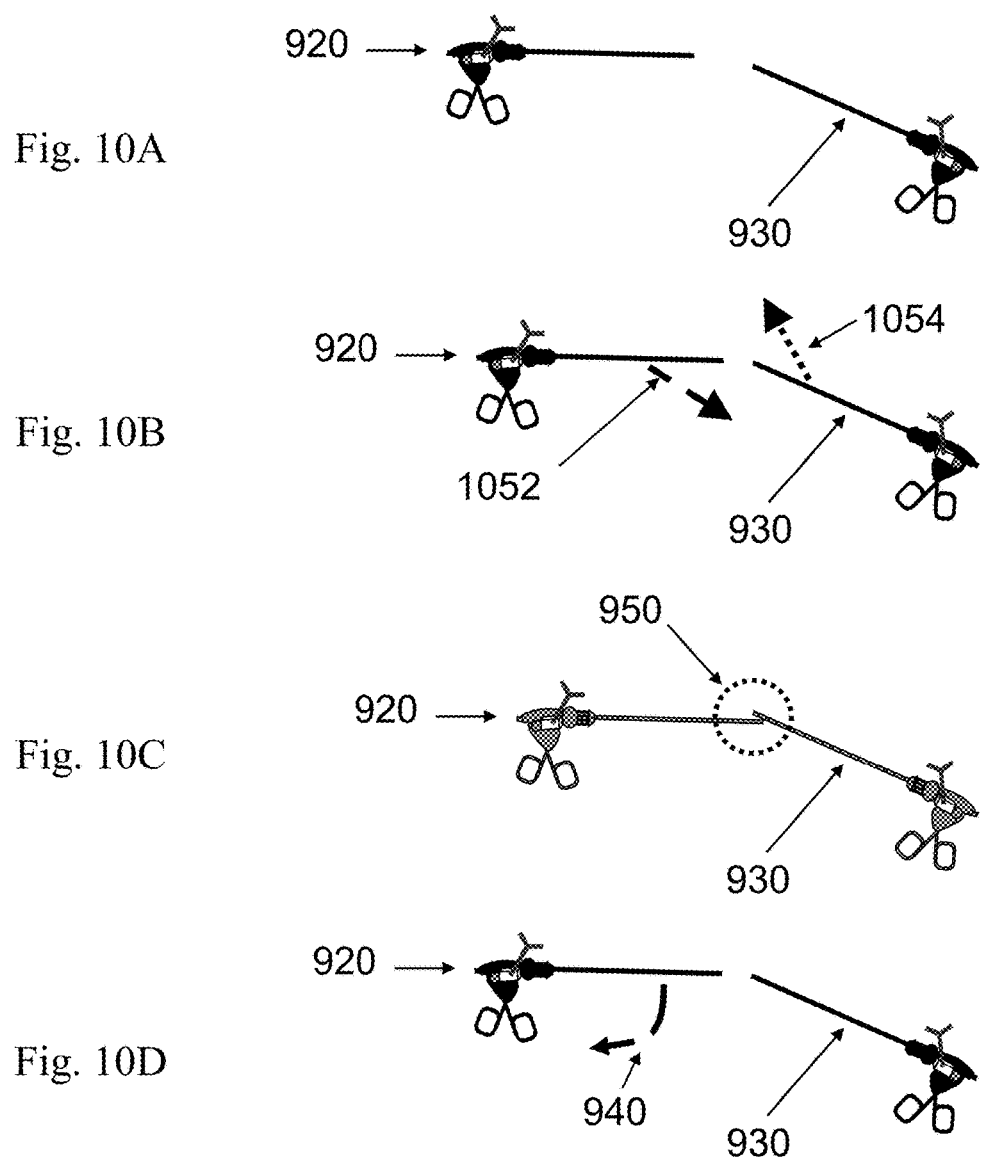
FIG. 10A-D schematically illustrates operation of an embodiment of the prediction function/rule.

FIG. 10A shows a left tool 920 and a right tool 930 at a time t.

FIG. 10B shows the same tools at a later time t+Δt, where Δt is a small time interval. Left tool 920 is moving to the right and downward (1052, dashed arrow), while right tool 930 is moving to the left and upward (1054, dotted arrow). If the motion continues, then by the end of the next time interval, in other words, at some time between time t+Δt and time t+2Δt, the tools will collide, as shown by tool tips within the dotted circle 950 in FIG. 10C.

In this embodiment, the system automatically prevents predicted collisions and, in this example, as shown in FIG. 10D, the system applies a motion 940 to redirect left tool 920 so as to prevent the collision.

In other embodiments, the system warns/signals the operator that a collision is likely to occur, but does not alter the movement of any tool. Such a warning/signaling can be visual or aural, using any of the methods known in the art.

In other embodiments, the prediction function can be enabled to, for non-limiting example, alter the field of view to follow the predicted movement of a tool or of an organ, to warn of (or prevent) predicted motion into a no-fly zone, to warn of (or prevent) predicted motion out of a preferred zone.

Example 9—Right Tool Function/Rule

Figure 11:
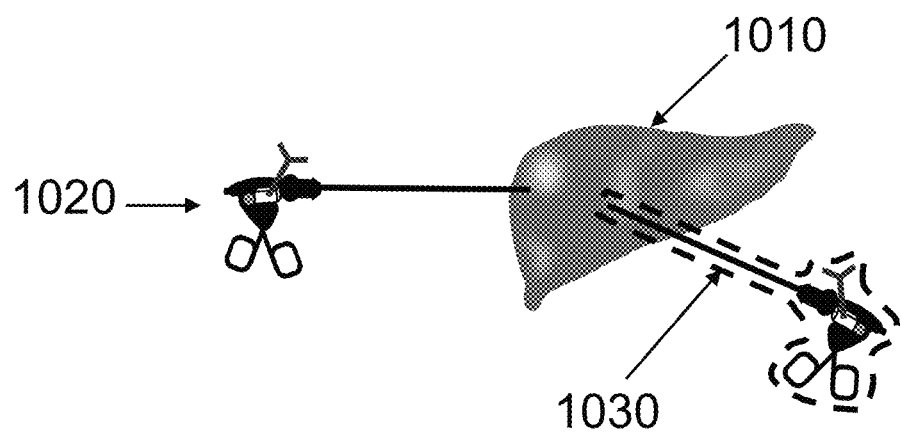
FIG. 11 schematically illustrates operation of an embodiment of the right tool function/rule.

In reference to FIG. 11, which shows, in a non-limiting manner, an embodiment of a right tool function. FIG. 11 schematically illustrates a liver 1010, a left tool 1020 and a right tool 1030. The right tool is labeled, illustrated schematically by the dashed line 1040, and its 3D spatial location is constantly and real-time stored in a database. Now, according to the right tool function/rule the endoscope constantly tracks the right tool.

It should be pointed out that the same rule/function applies for the left tool (the left tool function/rule).

Example 10—Field of View Function/Rule

Figure 12A:
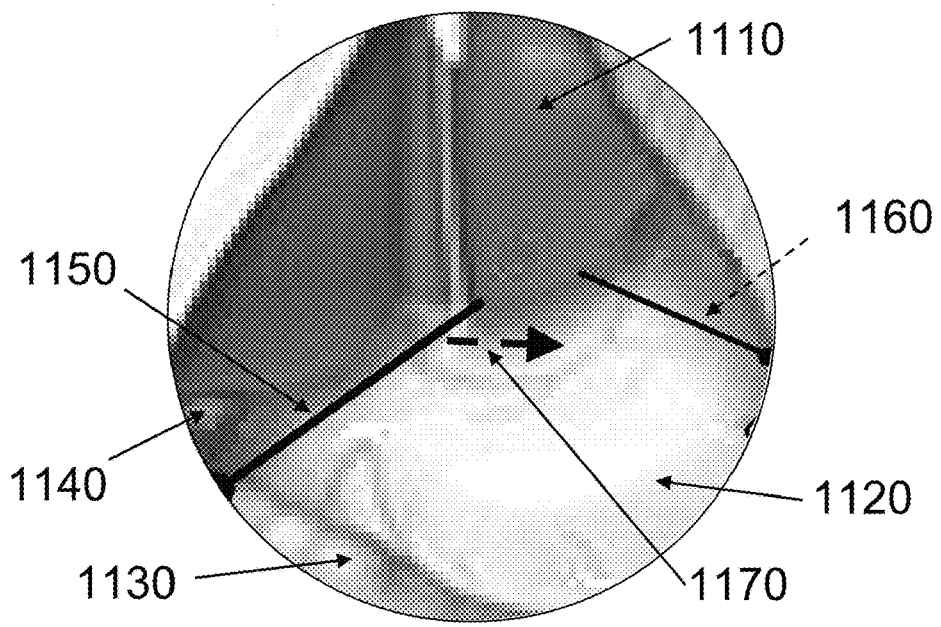
FIG. 12A-B schematically illustrates operation of an embodiment of the field of view function/rule.
Figure 12B:
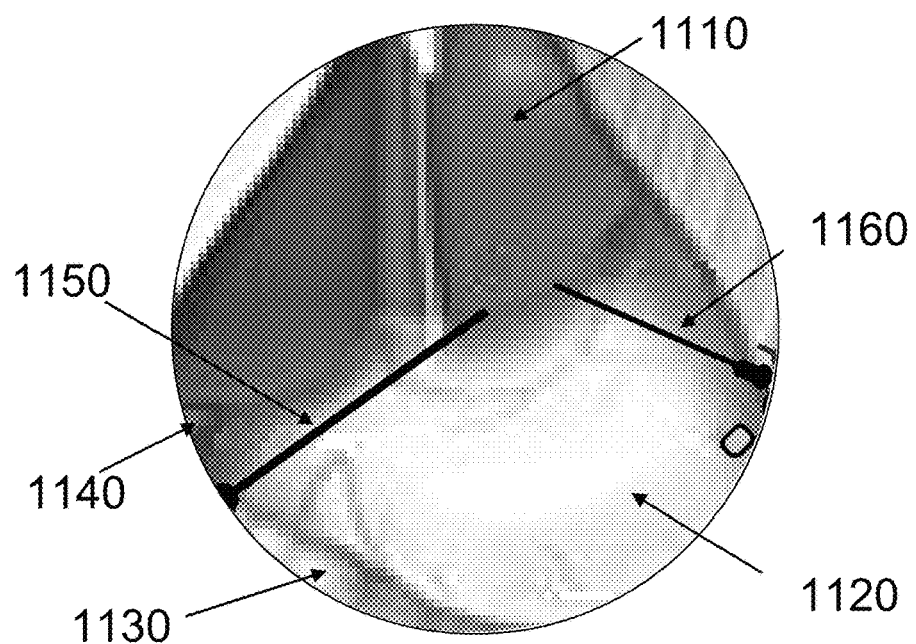

In reference to FIG. 12A-B, which shows, in a non-limiting manner, an embodiment of a field of view function/rule.

FIG. 12A schematically illustrates a field of view of the abdomen at a time t. In the field of view are the liver 1110, stomach 1120, intestines 1130 and gall bladder 1140.

The gall bladder is nearly completely visible at the left of the field of view. Two tools are also in the field of view, with their tips in proximity with the liver. These are left tool 1150 and right tool 1160. In this example, the field of view function/rule tracks left tool 1150. In this example, left tool 1150 is moving to the right, as indicated by arrow 1170.

FIG. 12B shows the field of view at time t+Δt. The field of view has moved to the right so that the tip of left tool 1150 is still nearly at the center of the field of view. It can be seen that much less of gall bladder 1140 is visible, as is less of the intestines, while more of right tool 1160 has entered the field of view. The liver 1110 and stomach 1120 have moved leftward in the image; more of the stomach is visible at the right edge of the field of view.

The field of view function/rule can be set to follow a selected tool, as in this example or to keep a selected organ in the center of the field of view. It can also be set to keep a particular set of tools in the field of view, zooming in or out as necessary to prevent any of the chosen tools from being outside the field of view.

Alternatively, the field of view function/rule defines n 3D spatial positions; n is an integer greater than or equal to 2; the combination of all of said n 3D spatial positions provides a predetermined field of view.

Each movement of the endoscope or the surgical tool within said n 3D spatial positions is an allowed movement and any movement of the endoscope or the surgical tool outside said n 3D spatial positions is a restricted movement.

Alternatively, said the field of view function/rule defines n 3D spatial positions; n is an integer greater than or equal to 2; the combination of all of said n 3D spatial positions provides a predetermined field of view.

According to the field of view function/rule, the endoscope is relocated if movement has been detected by said detection means, such that said field of view is maintained.

Example 11—Tagged Tool Function/Rule (or Alternatively the Preferred Tool Rule)

Figure 13:
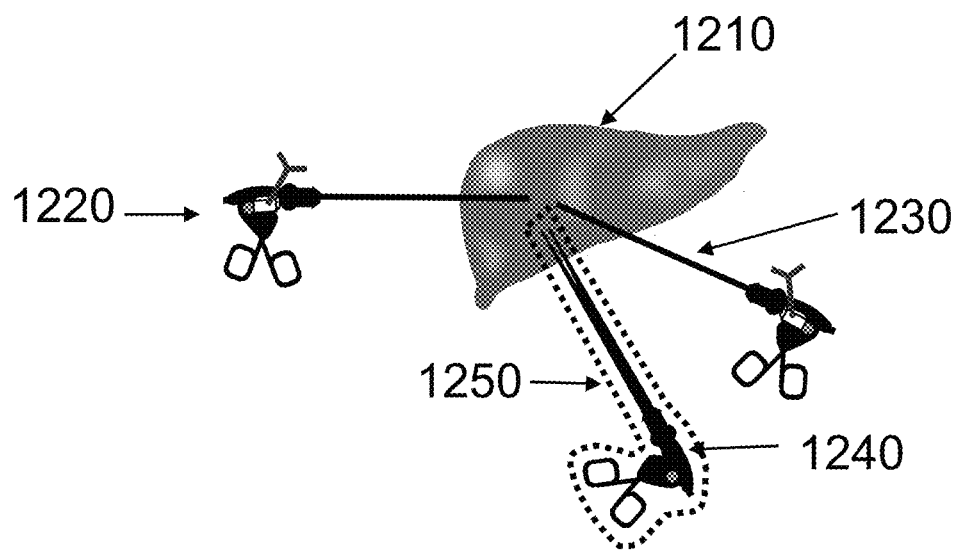
FIG. 13 schematically illustrates operation of an embodiment of the tagged tool function/rule.

In reference to FIG. 13, which shows, in a non-limiting manner, an embodiment of a tagged tool function/rule.

FIG. 12 shows three tools (1220, 1230 and 1240) in proximity to the organ of interest, in this example, the liver 1210.

The tool most of interest to the surgeon, at this point during the operation, is tool 1240. Tool 1240 has been tagged (dotted line 1250); the 3D spatial location of tool 1240 is constantly stored in a database and this spatial location has been labeled as one of interest.

The system can use this tagging for many purposes, including, but not limited to, keeping a tool 1240 in the center of the field of view, predicting its future motion, keeping it from colliding with other tools or keeping other tools from colliding with it, instructing the endoscope to constantly monitor and track said tagged tool 1240 and so on.

It should be noted that, in the preferred tool rule, the system tags one of the tools and performs as in the tagged tool rule/function.

Example 12—Proximity Function/Rule

Figure 14A:
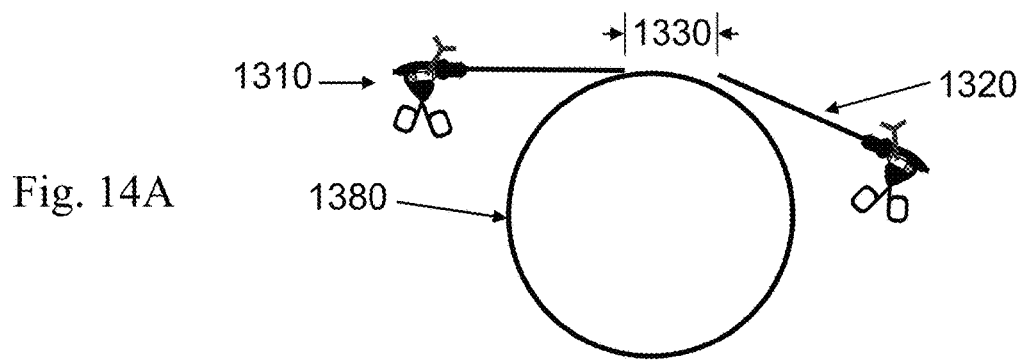
FIG. 14A-C schematically illustrates operation of an embodiment of the proximity function/rule.
Figure 14B:
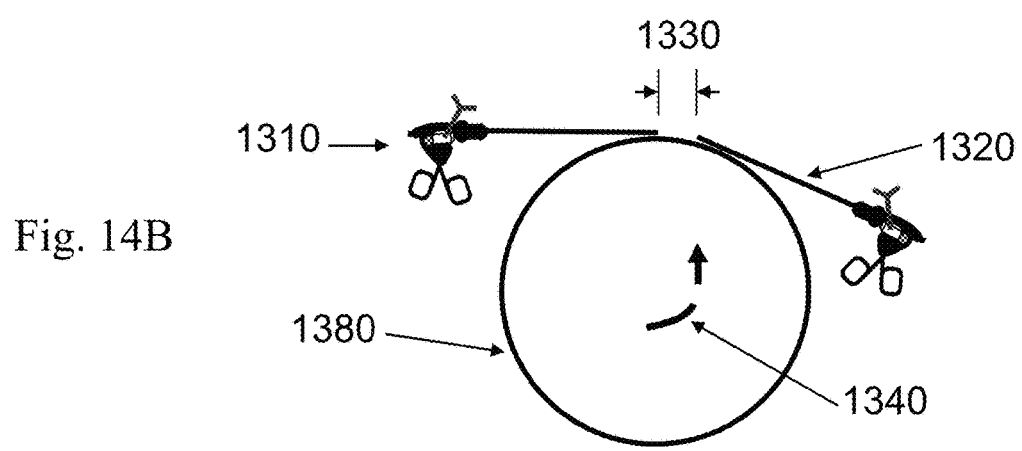
Figure 14C:
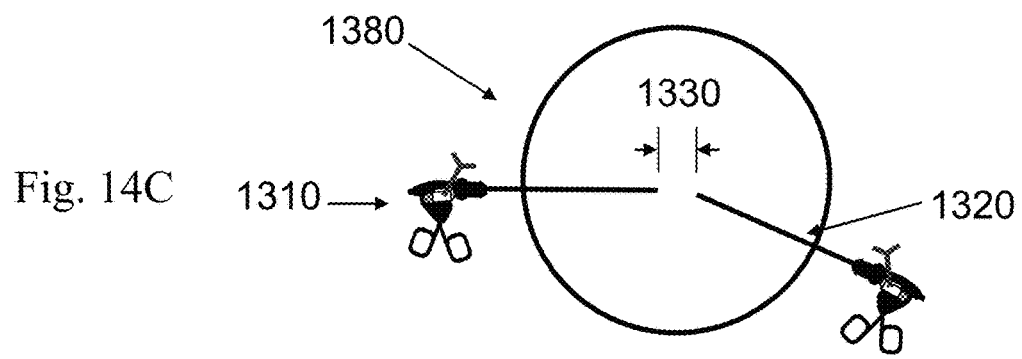

In reference to FIG. 14A-C, which shows, in a non-limiting manner, an embodiment of a proximity function/rule.

FIG. 14A schematically illustrates two tools (1310 and 1320) separated by a distance 1330 which is greater than a predefined proximity distance. Since tool 1310 is not within proximity of tool 1320, the field of view (1380) does not move.

FIG. 14B schematically illustrates two tools (1310 and 1320) separated by a distance 1330 which is less than a predefined proximity distance.

Since tool 1310 is within proximity of tool 1320, the field of view 1380 moves upward, illustrated schematically by arrow 1340, until the tips of tool 1310 and tool 1320 are in the center of field of view 1380 (FIG. 14C).

Alternatively the once the distance 1330 between the two tools 1320 and 1310 is smaller than a predetermined distance, the system alerts the user of said proximity (which might lead to a collision between the two tools). Alternatively, the system moves one of the tools away from the other one.

Example 13—Operator Input Function/Rule

Figure 15A:
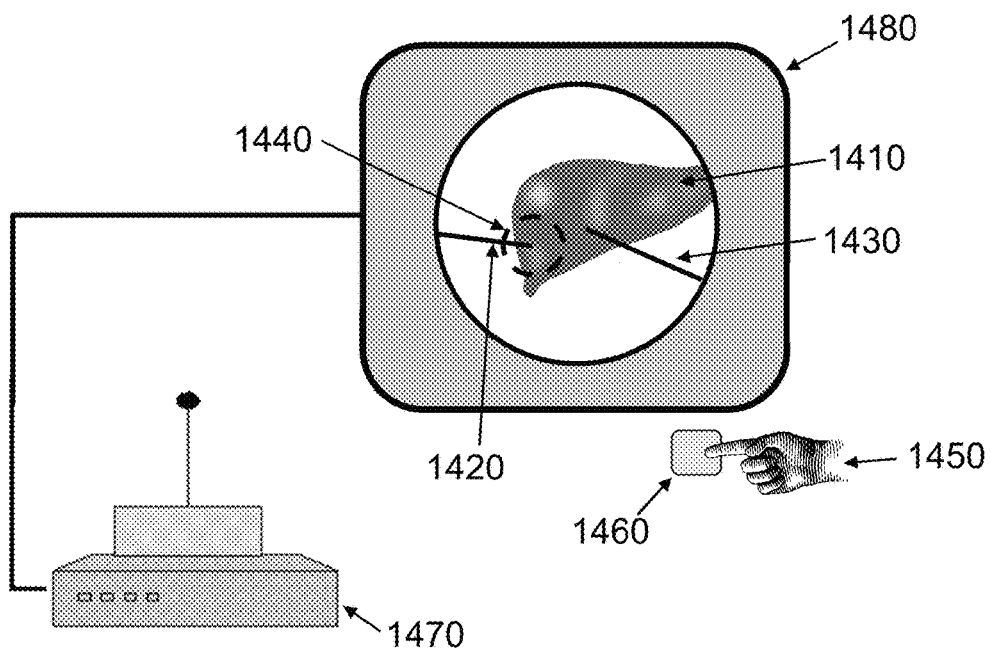
FIG. 15A-B schematically illustrates operation of an embodiment of the operator input function/rule.
Figure 15B:
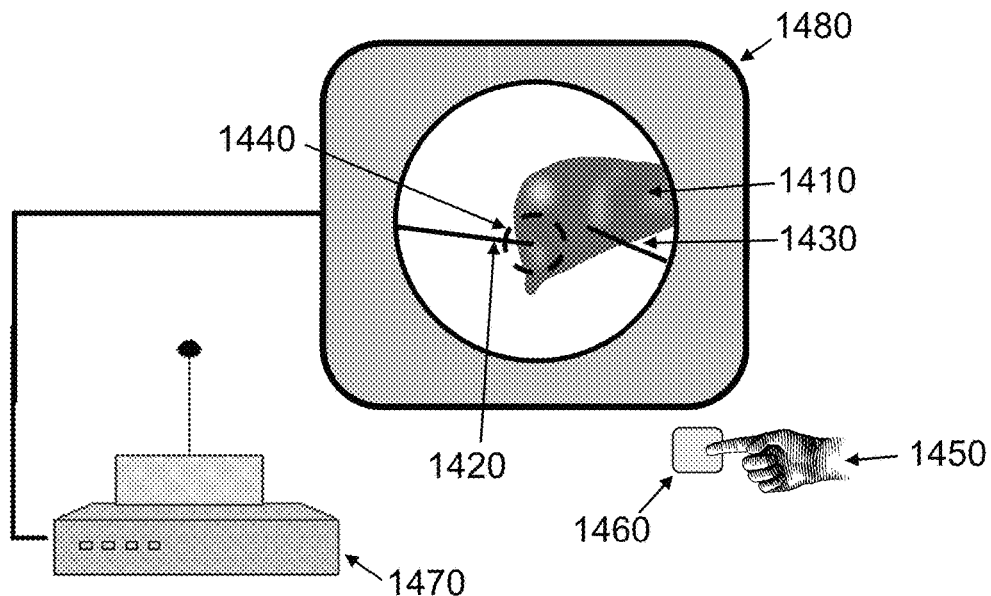

In reference to FIG. 15A-B, which shows, in a non-limiting manner, an embodiment of an operator input function/rule. According to this embodiment, input is received from the operator.

In the following example, the input received from the operator is which tool to track.

FIG. 15A schematically illustrates an endoscope with field of view 1480 showing a liver 1410 and two tools 1420 and 1430. A wireless transmitter 1460 is enabled to transmit coded instructions through receiver 1470. Operator 1450 first selects the tip of the left tool as the region of interest, causing the system to tag (1440) the tip of the left tool.

As illustrated in FIG. 15B, after selection of the tip of tool 1420 by operator 1450 by means of wireless transmitter 1460 and receiver 1470, the system then directs and modifies the spatial position of the endoscope so that the tagged tip 1440 of tool 1420 is in the center of the field of view 1480. In this non-limiting example, the liver 1410 and the tool 1430

Another example of the operator input function/rule is the following:

If a tool has been moved closely to an organ in the surgical environment, according to the proximity rule or the collision prevention rule, the system will, according to some embodiments, prevent the movement of the surgical tool.

According to some embodiments of the present invention, once the surgical tool has been stopped, any movement of said tool in the direction is interpreted as input from the operator to continue the movement of said surgical tool in said direction.

Thus, according to these embodiments, the operator input function/rule receives input from the operator (i.e., physician) to continue the move of said surgical tool (even though it is "against" the collision prevention rule). Said input is simply in the form of the continued movement of the surgical tool (after the alert of the system or after the movement prevention by the system).

Example 14—Constant Field of View Rule/Function

In reference to FIGS. 16A-G, which shows, in a non-limiting manner, an embodiment of a tracking system with a constant field of view rule/function.

In many endoscopic systems, the tip lens in the camera optics is not at a right angle to the sides of the endoscope. Conventionally, the tip lens angle is described relative to the right angle, so that a tip lens at right angles to the sides of the endoscope is described as having an angle of 0. Typically, angled endoscope tip lenses have an angle of 30° or 45°. This tip lens angle affects the image seen during zooming. FIG. 16A-E illustrates, in an out-of-scale manner, for a conventional system, the effect of zooming in the field of view in an endoscope with tip lens set straight in the end (FIG. 16A_C) vs. the effect of zooming in the field of view in an endoscope with angled tip lens (FIGS. 16D and 16E).

Figure 16A:
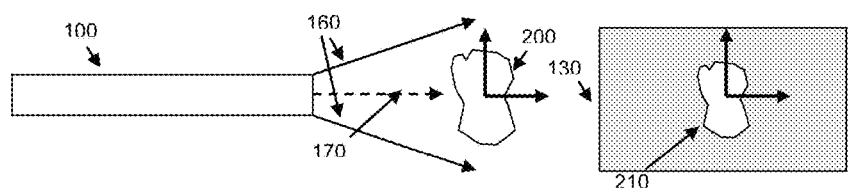
FIGS. 16A-G schematically illustrate an embodiment of a tracking system with a constant field of view rule/function.
Figure 16B:
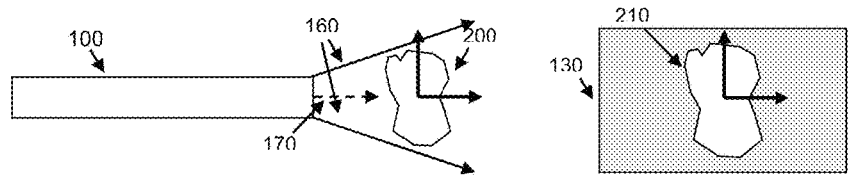
Figure 16C:
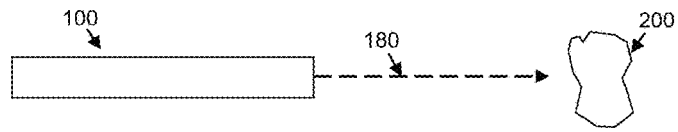
Figure 16D:
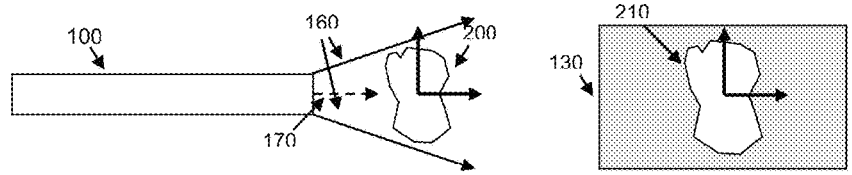
Figure 16E:
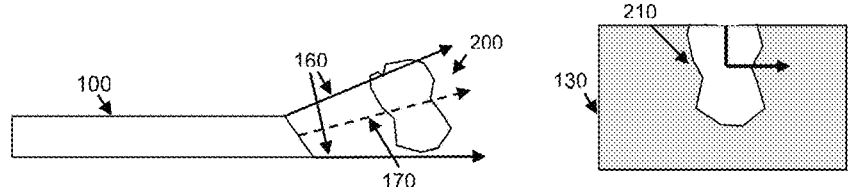
Figure 16F:
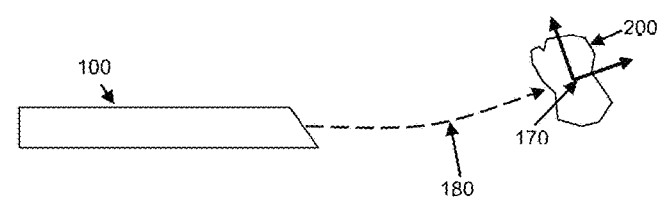

FIGS. 16A and 16E illustrate the endoscope (100), the object it is viewing (200) and the image seen by the endoscope camera (130) before the zoom. The solid arrows (160) show the limits of the field of view (FOV) and the dashed arrow (170), the center of the FOV; since the object is in the center of the FOV, an image of the object (210) is in the center of the camera image (130).

FIGS. 16B and 16E illustrate the endoscope (100), the object it is viewing (200) and the image seen by the endoscope camera (130) after the zoom. The solid arrows (160) show the limits of the FOV and the dashed arrow (170), the center of the field of view.

If the tip lens is set straight in the end of the endoscope (FIGS. 16A and 16B), an object (200) in the center FOV will be in the center of the FOV (and the camera image) (130) both before (FIG. 16A) and after (FIG. 16B) the zoom. As illustrated in an out-of-scale manner in FIG. 16C, the direction of motion of the endoscope during the zoom (180) is a straight line connecting the location of the center of the tip of the endoscope (100) at the start of the zoom with the center of the field of view at the start (and end) (170) of the zoom; the center of the endoscope tip will lie on this line at all times during the zoom. The correction of the zoom movement (and focusing on the same object within the field of view) is referred also as corrected zoom rule However, if the tip lens is set at an angle in the end of the endoscope (FIGS. 16D and 16E), then an object that is in the center of the FOV (and the camera image) before the zoom (FIG. 16D) will not be in the center of the FOV (or the camera image) after the zoom (FIG. 16E) since the direction of motion of the endoscope is not the direction in which the center of the field of view (170) points.

Figure 16G:
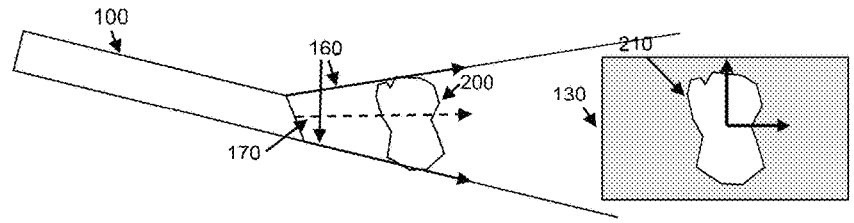

In some embodiments of the system of the present invention, the controlling means maintains a fixed center of the field of view (FOV) during zoom independent of the tip lens angle. In such systems, (FIGS. 16F and 16G) the endoscope (100) tip will move in a curved trajectory (180, FIG. 16F) such that the center of the FOV does not change during zooming (FIG. 16G).

Maintenance of a fixed center of the field of view can be can be made either by inputting the angle of the tip lens during setup, in which case, the system can calculate an appropriate trajectory, or by identifying the center of the field of view by analyzing the image. Inputting the tip lens angle means that no image analysis need be done; however, controlling the direction of motion of the endoscope during zoom via means that that the tip lens angle does not need to be input, obviating a possible source of error.

Example 15—Misalignment Rule/Function

According to some embodiments of the present invention, the system can inform the user of any misalignment of the same system.

Misalignment of the system may cause parasitic movement of the endoscope tip, where the endoscope tip does not move exactly in the expected direction. According to some embodiments of the system, the system comprises at least one sensor (e.g., gyroscope, accelerometer and any combination thereof) that calculates/estimates the position of the pivot point in real time in order to (a) inform the user of misalignment; or (b) calculate the misalignment so that the system can adjust its movement to prevent parasitic movement.

Example 16—Change of Speed Rule/Function

Figure 17:
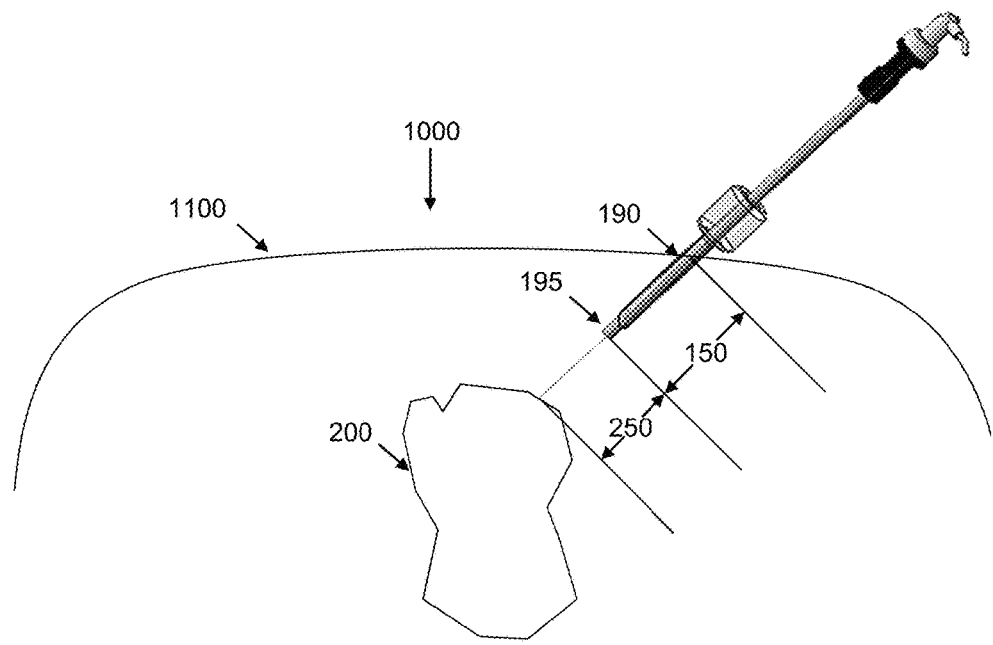
FIG. 17 schematically illustrates an embodiment of a tracking system with a change of speed rule/function.

In reference to FIG. 17, which shows, in a non-limiting manner, an embodiment of a tracking system with a change of speed rule/function.

In conventional endoscopic control systems, motion of the endoscope occurs at a single speed. This speed is fairly fast so that the endoscope can be moved rapidly between locations that are well separated. However, this means that making fine adjustments is so difficult that fine adjustments are normally not made. In an embodiment of the present invention, the speed of the tip of the endoscope is automatically varied such that, the closer the endoscope tip is to an object, be it a tool, an obstacle, or the object of interest, the more slowly it moves. In this embodiment, as shown in FIG. 17, measurements are made of the distance X (150) from the tip (195) of the endoscope (100) to the pivot point of the endoscope (190), where said pivot point is at or near the surface of the skin (1100) of a patient (1000). Measurements are also made of the distance Y (250) from the tip of the endoscope (195) to the object (200) in the center of the FOV. From a predetermined velocity $V_p$, the actual velocity of the tip of the endoscope at a given time, $V_{act}$, is calculated from $$V_{act} \propto \frac{Y}{X} V_p$$

Therefore, the closer to the object at the center of the FOV, the more slowly the endoscope moves, making it possible to use automatic control of even fine adjustments, and reducing the probability that the endoscope will come in contact with tissue or instruments.

In embodiments of the system, the harder the control unit is pressed, the faster the endoscope tip moves. In these embodiments, the system provides a warning if the speed is above a predetermined maximum. Examples of the method of warning include, but are not limited to, a constant volume tone, a constant pitch tone, a varying volume tone, a varying pitch tone, a vocal signal, a constant color visual signal, a constant brightness visual signal, a varying color visual signal, a varying brightness visual signal, a signal visible on at least some part of the endoscope image, a signal visible on at least some portion of the patient, a signal visible in at least some portion of the surroundings of the patient, a vibration in the control unit, a temperature change in the control unit, and any combination of the above.

According to some embodiments of the present invention, the velocity of the endoscope's movement will be adjusted as a function of the distance of the endoscope's tip from the organ\tissue.

Example 17—Fixed Point Rule/Function

In reference to FIGS. 18-19, which show, in a non-limiting manner, an embodiment of a system with a fixed point rule/function.

According to this embodiment, the endoscope 'tracks' (follows) a fixed point rule/function.

It should be emphasized that the term 'fixed point' does not refer to an absolute fixed 3D position.

The 'fixed point' can be a 3D position which is defined relative to an element in the cavity. Alternatively, the 'fixed point' can be defined as a function of a predefined position (e.g., tip of a tool/s) such that when said predefined position moves (e.g., when the tool moves) said 'fixed point' moves accordingly. According to this embodiment, the endoscope follows said 'fixed point'.

The fixed point rule/function identifies a "fixed point" in 3D space. The fixed point can be, for non-limiting example, fixed relative to the coordinate system of the location estimating means, or it can be fixed relative to at least one object within the body cavity, such as a tool, tissue or organ. If the point is fixed relative to the coordinate system of the location estimating means, then it functions like a conventional fixed point, being nonmoving relative to the ground.

If the point is fixed relative to a single position on a single tool, then it functions similarly to the tagged tool function (Example 11 above).

Figure 18A:
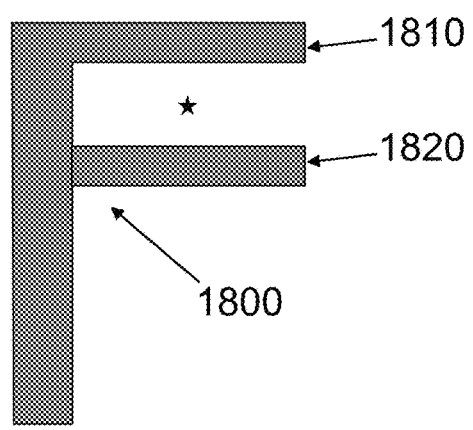
Figure 18B:
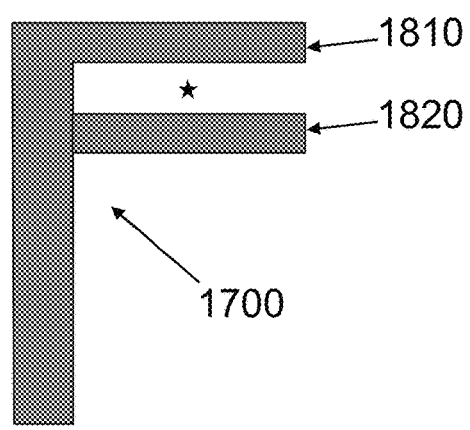

The point can be fixed relative to two positions on a single position\tool. For non-limiting example, it can be fixed relative to the blades of a scissors or the jaws of a clamp. A non-limiting example is shown in FIG. 18A-B, which shows a fixation point which is the point in the middle of the jaws (1810, 1820) of a clamp (1800) and halfway between them (illustrated as a star). Once the jaws (1810, 1820) moved— the fixation point moves as well (see FIG. 18B relatively to FIG. 18A).

The point can be fixed relative to an identifiable location on an organ, or relative to a portion of an organ. A non-limiting example of a point fixed relative to an identifiable point on an organ is fixation relative to the location of the first bifurcation in the left coronary artery. A non-limiting example of a point fixed relative to an organ is fixation relative to the center of the heart, with the center of the heart being defined as the point, on average, furthest from the perimeter of the heart. In both cases, the fixation point can move as the heart beats.

The point can also be fixed relative to more than one object. For non-limiting example, it can be fixed relative to two tools, or to both a tool and an organ. Non-limiting examples of fixation relative to two tools include a point a fixed fraction of the distance between the tool tips, a point a predetermined distance from a line joining the tool tips, the point where two tools will contact each other, if their present movement pattern continues FIG. 19A-B shows two tools (920 and 930) a distance D apart, with the fixed point (illustrated as a star) halfway between them (distance D/2 from each).

Again, once one of the tool moves, said fixed point will be re calculated and re-positioned according to the predetermined criteria (in this case in the halfway between tool 920 and 930), see FIG. 19B relatively to FIG. 19A.

FIG. 20A-B shows an embodiment in which the fixed position (illustrated as a start) is defined to be at a fix distance, D from tool 930. According to this embodiment the fixed position is also defined to be parallel to said tool 930.

Again, once the tool moves, said fixed point will be re calculated and re-positioned according to the predetermined criteria (in this case at a fix distance, D from tool 930 and parallel to the same), see FIG. 20B relatively to FIG. 20A.

The system can use this tagging for many purposes, including, but not limited to, keeping the fixed point (star) in the center of the field of view, predicting its future motion, keeping it at a particular location relative to another object (e.g., keeping a clamp fixed point at the location of an incision to be clamped), instructing the endoscope to constantly track the fixed point and so on.

Example 18—Maximum Speed Rule/Function

In a variant of embodiments where an instrument is tracked, tracking occurs only if the speed of the tracked object, typically a tool, is below a predetermined maximum speed. If the speed of the tracked object is above the predetermined maximum speed, tracking is terminated.

In a further variant of such embodiments, tracking is terminated if the speed of the endoscope is above a predetermined maximum speed, independent of the speed of the tracked object.

Example 19—Physical/Virtual Zoom Rule/Function

During zoom, especially zoom inward, endoscope travel can be limited by many factors, including both limits on travel imposed by the maneuvering system, and limits on travel imposed by space available inside the body. For example, the diameter of an endoscope tip can be such that, if it were to travel further into a restricted space, it would come into contact with body tissues on at least one side.

In some embodiments, zooming-in and/or zooming out can be extended by use of virtual zoom. In such embodiments, when the endoscope has reached a determinable point in a zoom, such as, in a zoom toward an object, a position such that further travel would bring a part of the endoscope into contact with an organ, the endoscope ceases to move. However, the image as seen in a display continues to zoom, with the system generating the zoomed image. In some embodiments, further detail is apparent as the image continues to zoom. This information can be from sub-pixel information from stored information, possibly from other modalities, or from any other conventional image-enhancement process. In some embodiments, the image of the center of the field of view will enlarge, but no new information will be available. any combination of the above can be used.

In virtual zoom outward, in some embodiments, the endoscope uses a lens such that the displayed image only comprises a part of the lens field of view, thus enabling enlargement of the displayed region of the body during virtual zoom outward. In some embodiments, stored information is used to enlarge the displayed region.

Example 20—Virtual Rotation of Scene Rule/Function

A non-limiting example of virtual rotation of a scene will be given in FIG. 21A-C. FIG. 21A shows an endoscope (100) with an alignment (172) at some time $t_a$. The image (210) in the display (130) has an alignment (215) corresponding to the alignment (172) of the endoscope (100).

In the course of time, the alignment of the endoscope (100) rotates (150). At some later time $t_b$, (FIG. 21B) the alignment of the endoscope (100) has rotated by an angle θ. In a conventional endoscope, this will rotate the image (210) in the display (130) by the same angle θ.

In preferred embodiments of the present invention, as shown in FIG. 21C, as the alignment of the endoscope changes, software rotates (155, FIG. 21B) the image (210) so that the alignment (215) of the image (210) remains the same, no matter what the alignment (172) of the endoscope.

Example 21—Input Protocol, Movement of a Tool

Non-limiting examples of input protocols involving movement of tools and associated output protocols will be given. In these examples, the input protocol of movement is a fixed predetermined gesture.

Figure 22B:
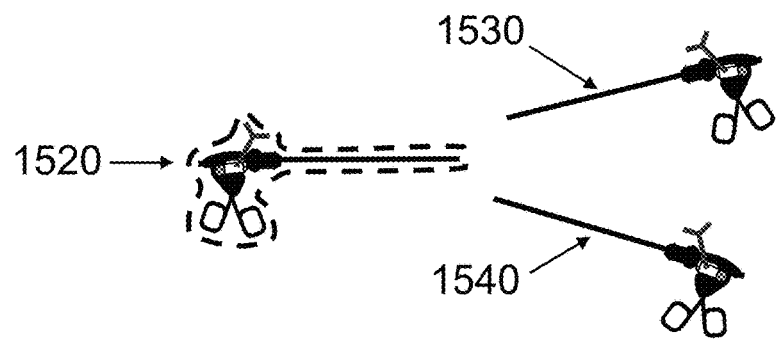

In reference to FIG. 22A-B, which shows, in a non-limiting manner, an embodiment of an input protocol comprising shaking a tool.

In FIG. 22A, a system comprising three tools (1520, 1530, 1540) is illustrated; the system is tracking (dashed line) the upper right tool (1530). In order to change tracking to the leftmost tool (1520), the leftmost tool (1520) is shaken (1550, dotted line)

As shown in FIG. 22B, once the leftmost tool (1520) has been shaken. according to the output protocol, the system tracks (dashed line) the leftmost tool (1520).

Figure 23A:
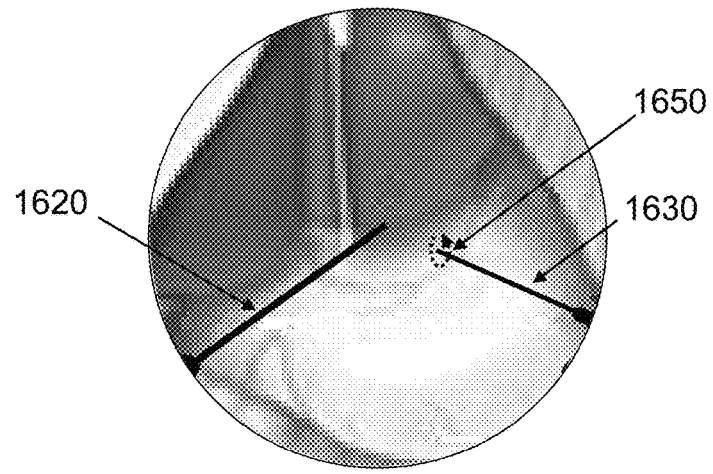
Figure 23B:
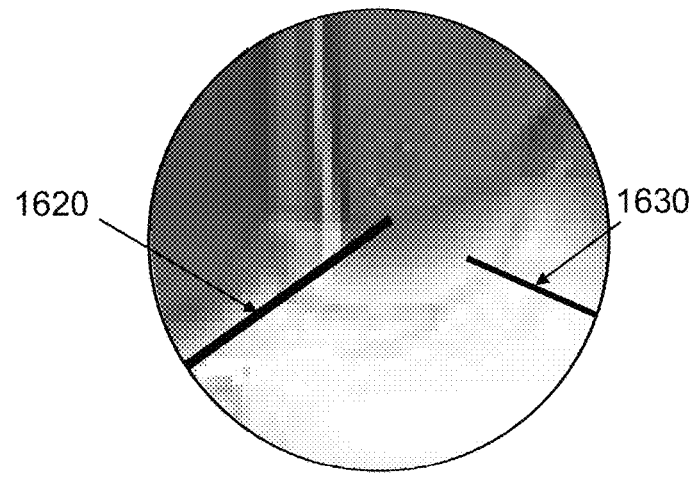

In reference to FIG. 23A-B, which shows, in a non-limiting manner, another embodiment of a tracking system with a predetermined input protocol.

In FIG. 23A, two tools (1620, 1630) are being used in an operation on the liver (1610). To command a zoom inward, the tip of a tool, in this case, the right tool (1630), is moved in a clockwise circle (1650, dotted line).

As shown in FIG. 23B, once the circle has been made, according to the output protocol, the field of view is zoomed inward, keeping the center of the field of view the same, so that the image is magnified by 50%.

In this embodiment, an input protocol of a counterclockwise circle (not shown) of either tool would result in an output protocol of a zoom outward, increasing the field of view and demagnifying the image by 50%.

The embodiments shown herein are merely exemplary—there are many input protocols and many output protocols which have not been shown.

It should be noted that the association of input and output protocols is arbitrary; any input protocol can be associated with any output protocol.

Example 22—Input Protocol, Movement of an Operator

Non-limiting examples of input protocols involving movement of a part of an operator, in this case the hand, and associated output protocols will be given. In these examples, the input protocol is a fixed predetermined gesture.

Figure 24A:
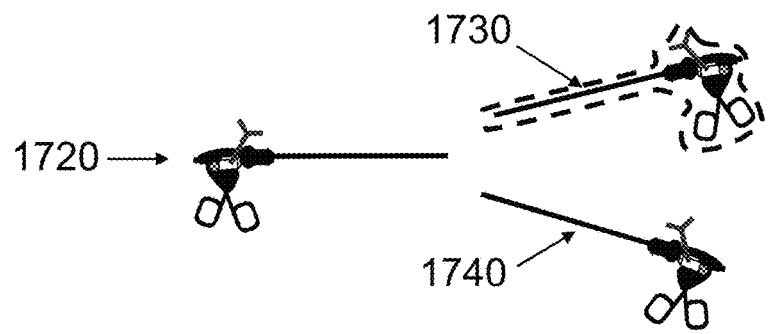
FIGS. 24A-C, 25A-C, 26A-C and 27A-C schematically illustrate an embodiment of a tracking system with an input protocol in which a portion of the body of an operator is moved.
Figure 24B:
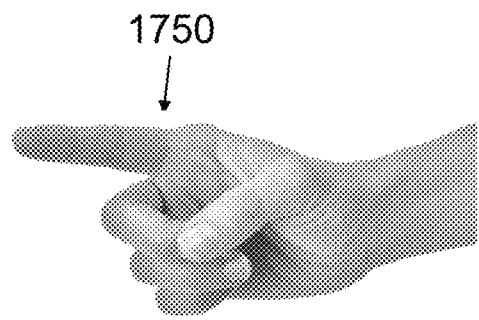
Figure 24C:
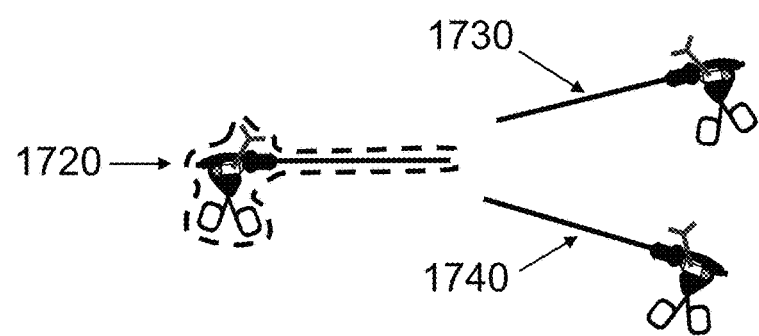

In reference to FIG. 24A-C, which shows, in a non-limiting manner, an embodiment of an input protocol comprising pointing a finger.

In FIG. 24A, a system comprising three tools (1520, 1530, 1540) is illustrated; the system is tracking (dashed line) the upper right tool (1530). As shown in FIG. 24B, in order to change tracking to the leftmost tool (1520), the operator points to the left (1750), in this case with the right hand.

As shown in FIG. 24C, once operator has pointed, according to the output protocol, the system tracks (dashed line) the leftmost tool (1520).

Figure 25A:
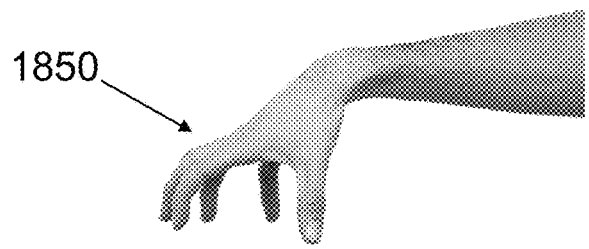
Figure 25B:
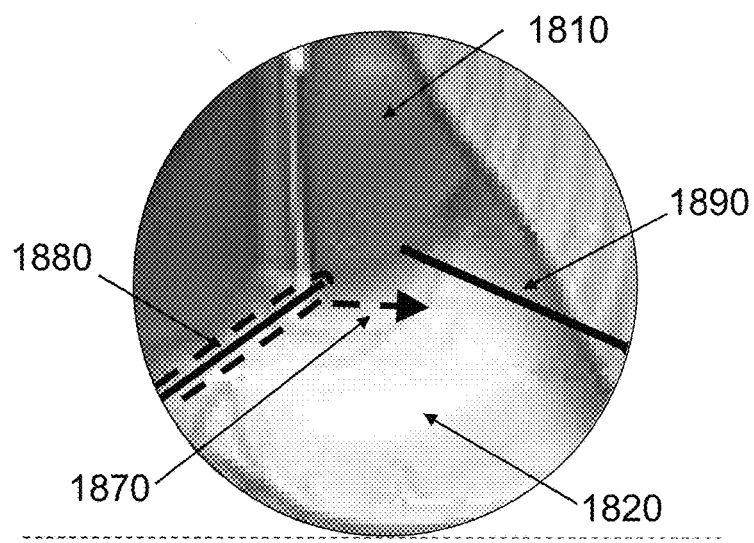
Figure 25C:
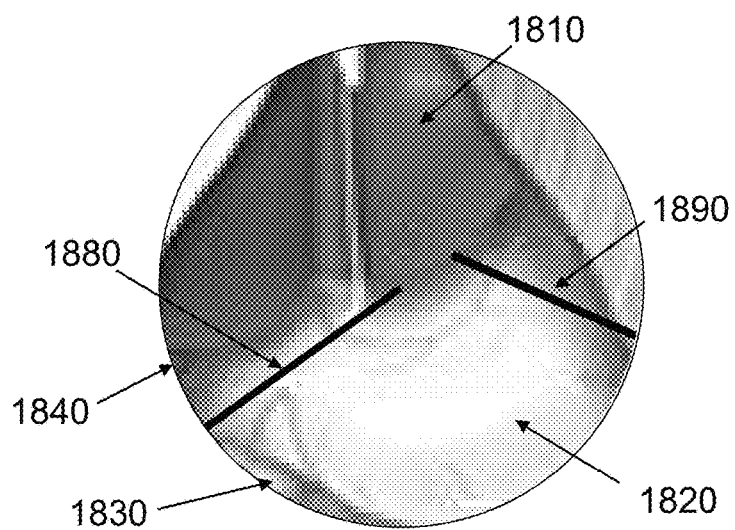

In reference to FIG. 25A-C, which shows, in a non-limiting manner, an embodiment of an input protocol for centering a field of view.

In this embodiment, the input protocol to place the center of the field of view at the tip of the tracked tool is holding the hand open downward with the finger spread as though picking up a bowl (FIG. 25A, 1850).

As shown in FIG. 25B, the tip of the tracked tool (1880, dashed line) is to the left of the center of the field of view, which shows two tools (1880, 1890), the liver (1810) and the stomach (1820).

The gesture (FIG. 25A, 1850) commands the output protocol, that the center of the field of view be moved to the right (dashed arrow, 1870). After the output protocol has been completed, the tip of the tracked, left, tool (1880, dashed line) is at the center of the field of view, which shows the two tools (1880, 1890), liver (1810), the stomach (1820), the intestines (1830) and gall bladder (1840).

Figure 26A:
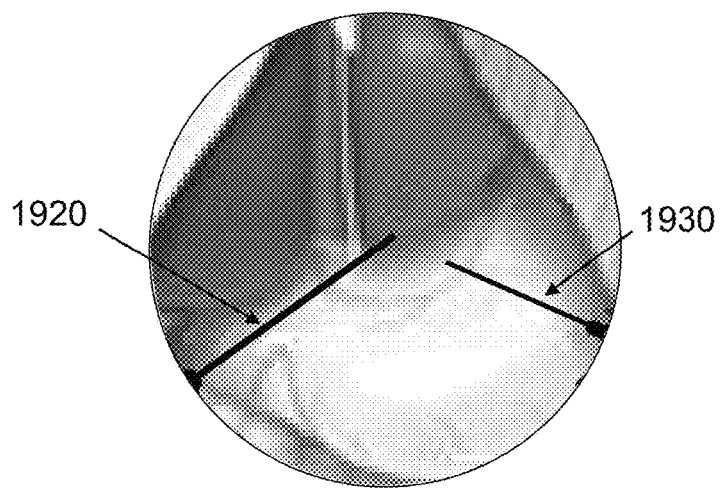
Figure 26B:
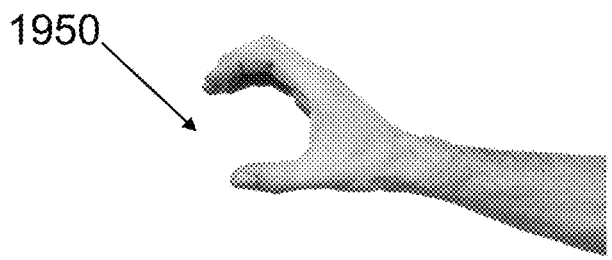
Figure 26C:
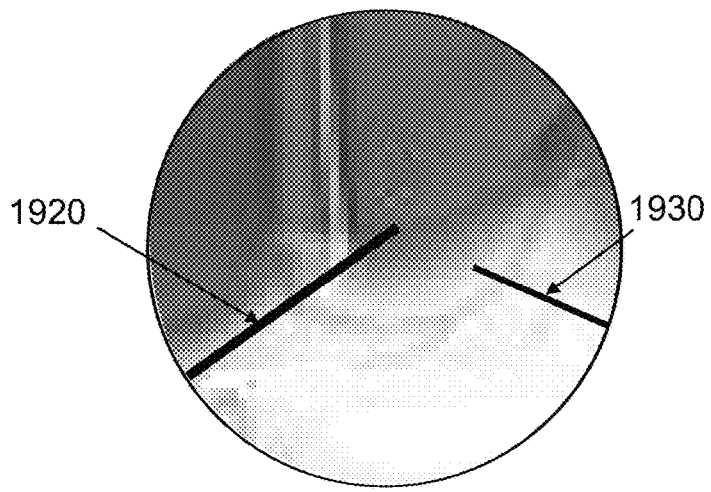

In reference to FIG. 26A-C, which shows, in a non-limiting manner, an embodiment of an input protocol to zoom an endoscope.

In this embodiment, the input protocol to zoom the endoscope inward is holding an open hand sideways with the fingers together, although picking up a book (FIG. 19A, 1950).

In FIG. 26B, two tools (1920, 1930) are being used in an operation on the liver (1910).

As shown in FIG. 26C, once the input protocol (holding the hand as though picking up a book) is made, according to the output protocol, the field of view is zoomed inward, keeping the center of the field of view the same, so that the image is magnified by 50%.

In this embodiment, an input protocol of a book-holding gesture pointing toward the right would result in an output protocol of a zoom outward, increasing the field of view and demagnifying the image by 50%.

The embodiments shown herein are merely exemplary—there are many input protocols and many output protocols which have not been shown.

It should be noted that the association of input and output protocols is arbitrary; any input protocol can be associated with any output protocol.

Example 23—Input Protocol, Movement of an Operator

A non-limiting example of an input protocol involving movement of a part of an operator, in this case the eye, and the associated output protocol will be given. In this example, the input protocol is a fixed predetermined gesture.

Figure 27A:
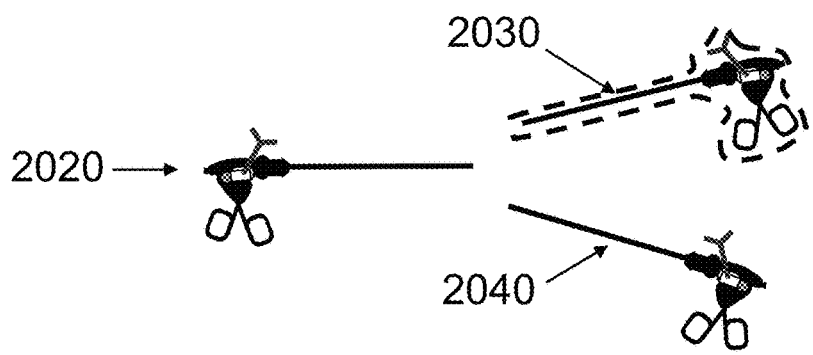
Figure 27B:
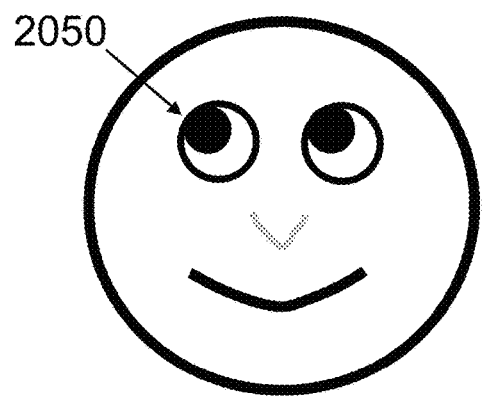
Figure 27C:
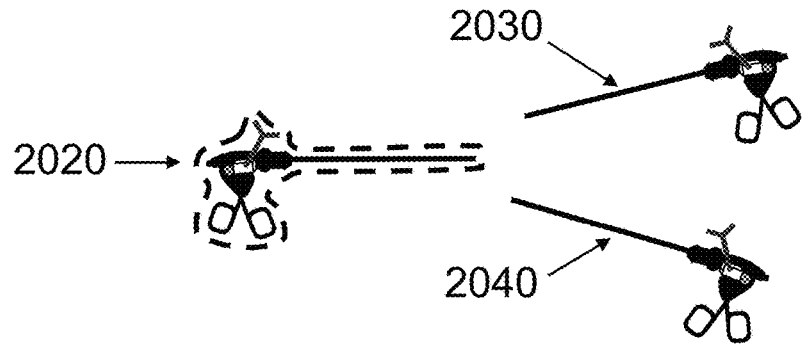

In reference to FIG. 27A-C, which shows, in a non-limiting manner, an embodiment of an input protocol comprising moving at least one eye.

In FIG. 27A, a system comprising three tools (2020, 2030, 2040) is illustrated; the system is tracking (dashed line) the upper right tool (2030). In order to change tracking to the leftmost tool (2020), at least one eye is moved to look upward to the left, preferably so that the operator is no longer looking at the display screen, as shown in FIG. 27B (2050). In preferred embodiments, the eye gesture need only be a quick glance, a momentary removal of the eyes from the display.

As shown in FIG. 27C, once the eye gesture (2050) is complete, according to the output protocol, the system tracks (dashed line) the leftmost tool (2020).

Example 24—Input Protocol, Position of a Tool

Figure 28A:
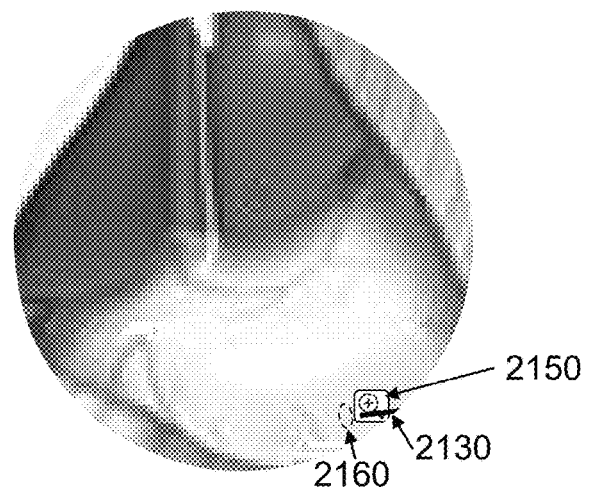
FIGS. 28A-B schematically illustrate an embodiment of a tracking system with an input protocol in which a tool is positioned.
Figure 28B:
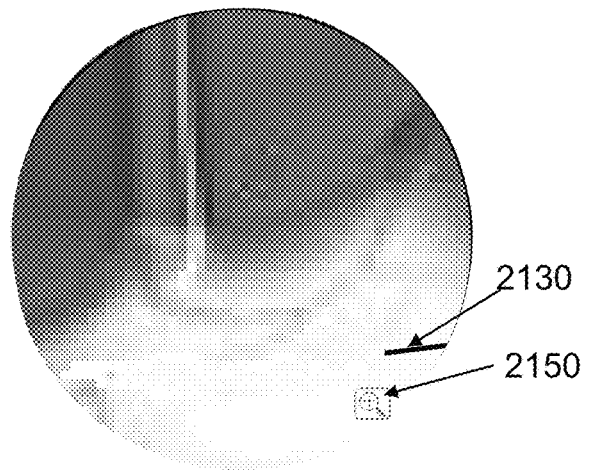

A non-limiting example of an input protocol involving position of a tool is shown in FIG. 28A-B.

In FIG. 28A, an embodiment of a display image is shown. The display comprises at least one icon (2150), with each icon being associated with an output protocol. In this embodiment, icons are invisible until a tool "enters" an icon, in other words, until the image of the tool is in the region of the display which can show the icon. In other embodiments, at least some icons are visible at all times.

In this embodiment, once a tool (2130) has entered an icon (a predetermined location\area\volume within the surgical environment shown on the screen) (2150), the output protocol is activated by moving the tool in a gesture which encircles the icon (2160, dotted arrow). In other embodiments, entering the icon region activates the output protocol; in yet other embodiments, other gestures are used.

In this exemplary embodiment, the icon (2150) shows a zoom-inward (+) symbol. After the circling motion (2160, dotted arrow) is completed, the system zooms the endoscope inward until the tool is removed from the icon, whereupon zooming stops and a magnified image is shown (FIG. 28B). The location of the icon is shown greyed-out in FIG. 28B for illustrative purposes. In preferred variants of this embodiment, an icon would only be showed greyed-out if the function with which it is associated is unavailable. In preferred variants, icons are preferably outside the image of the field of view or invisible when not in use, in order to ensure that the image of the field of view is as visible as possible.

According to another embodiment, In this embodiment, once a tool (2130) has entered an icon (a predetermined location\area\volume within the surgical environment shown on the screen) (2150), the output protocol is activated by tracking said tool (2130).

According to another embodiment, In this embodiment, once a tool (2130) has entered an icon (a predetermined location\area\volume within the surgical environment shown on the screen) (2150), the output protocol is activated by tagging and tracking said tool (2130).

Example 25—Input Protocol, Tagging of an Object

Figure 29A:
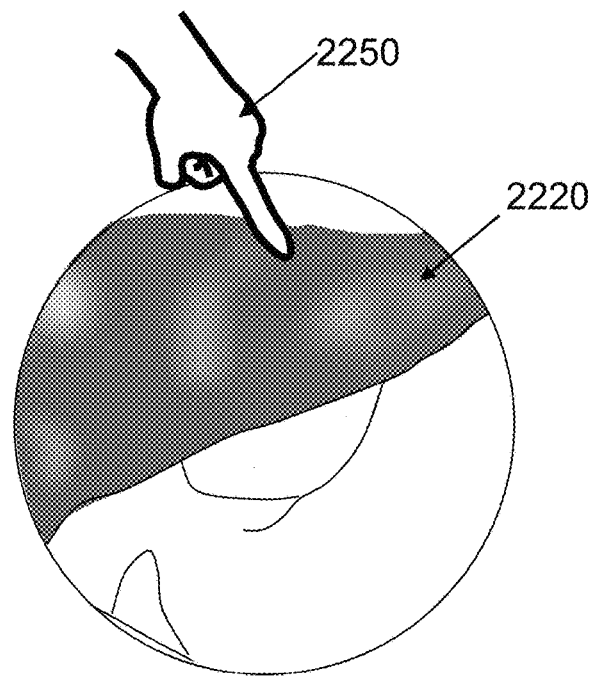
FIGS. 29A-B schematically illustrate an embodiment of a tracking system with an input protocol in which an object is tagged.
Figure 29B:
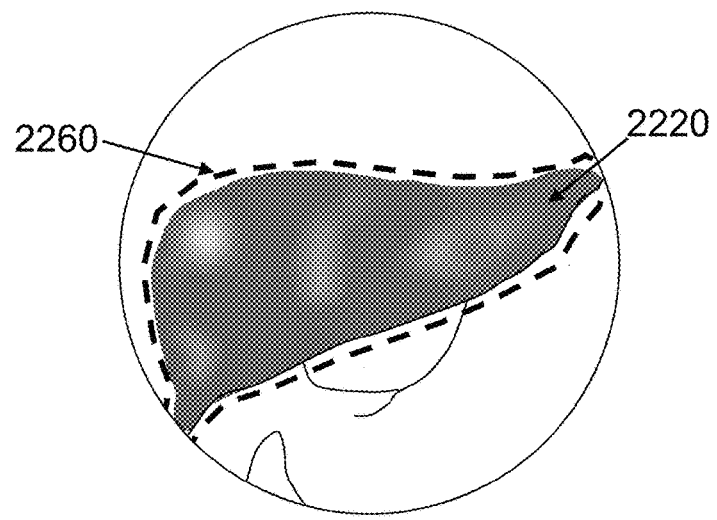

A non-limiting example of an input protocol comprising a command by a moving element is shown in FIG. 29A-B.

In this embodiment, as shown in FIG. 29A, the command is pointing by a finger of an operator (2250) at the object (2240) to be tagged.

As shown in FIG. 29B, the output protocol tags (2260, dashed line) the object, centers it in the field of view, and zooms the object until it is entirely within the field of view and fills the field of view in at least one direction.

Example 26—Input Protocol, Activation of a Tool

Figure 30A:
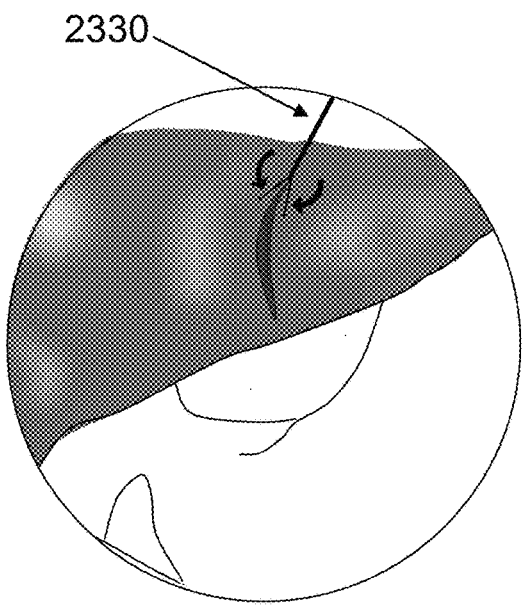
FIGS. 30A-B schematically illustrate an embodiment of a tracking system with an input protocol in which a tool is activated.
Figure 30B:
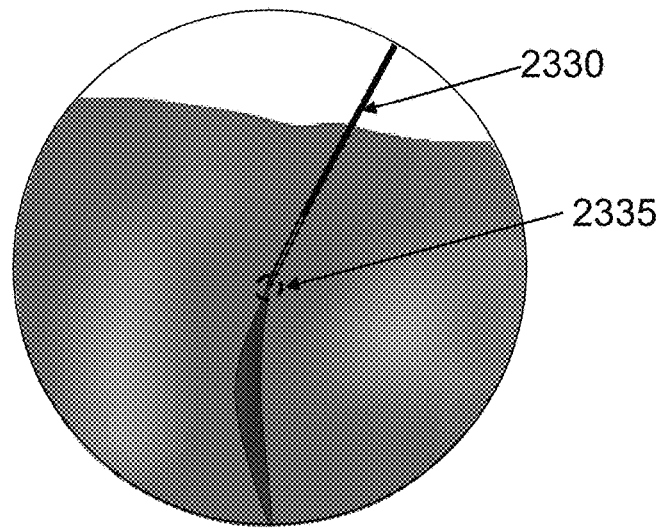

A non-limiting example of an input protocol comprising activation of a tool is shown in FIG. 30A-B.

In this embodiment, as shown in FIG. 30A, the tool (2330) is a grasper and activation comprises closing the grasper (2350, curved arrows).

Closing (2350, curved arrows) of the grasper (2330) results in an output protocol in which (FIG. 23B) the tip (2335, dashed circle) of the grasper (2330) is placed in the center of the field of view and the view zoomed to give a good view of the tip of the grasper.

Example 27—Input Protocol, Tool Reaches Edge of Field of View

Figure 31A:
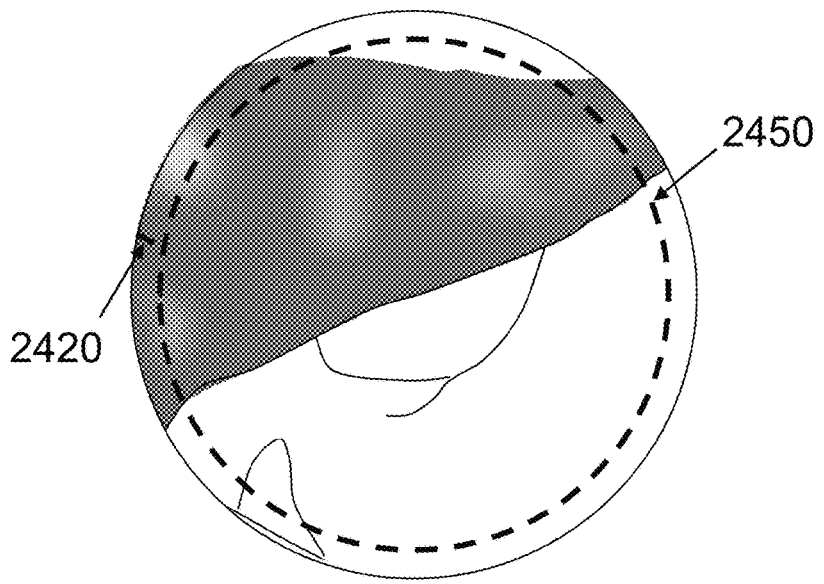
FIGS. 31A-B schematically illustrate an embodiment of a tracking system with an input protocol in which a tool is tracked if the tool reaches an edge of a field of view.
Figure 31B:
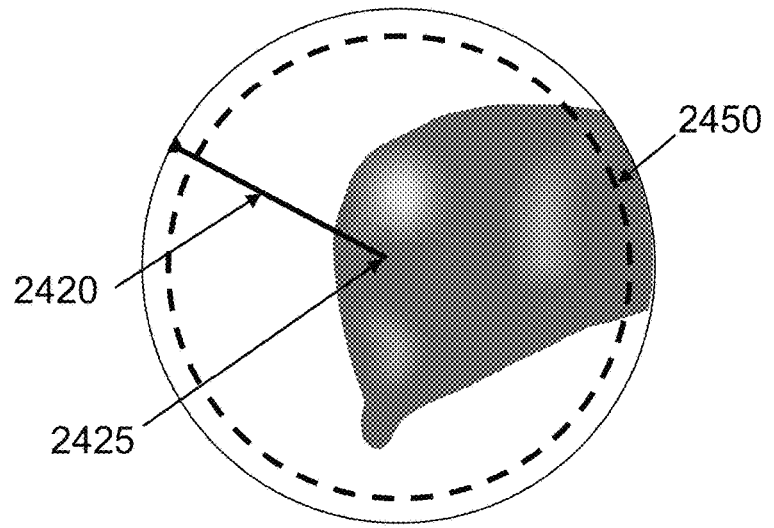

A non-limiting example of an input protocol comprises a tagged object reaching an edge of the field of view, as shown in FIG. 31A-B.

In this embodiment, as shown in FIG. 31A, the tagged object is a tool (2420). When the tool is less than a predetermined distance (2450, dotted line) from an edge of the field of view, an associated output protocol is activated.

The associated output protocol comprises placing the tip (2425) of the tool (2420) at the center of the field of view.

Example 28—Relationship Between Articles

A protocol, either an input protocol or an output protocol, can comprise a predetermined interaction between at least two articles, where an interaction involves a relationship between the articles. An article can be selected from a group consisting of at least a portion of a tool, at least a portion of an endoscope, at least a portion of a body, at least a portion of an organ, at least a portion of a tissue, at least a portion of an object and any combination thereof, where tissue refers to a structure in the body including, but not limited to, a membrane, a ligament, fat, mesentery, a blood vessel, a nerve, bone, cartilage, a tumor, a cyst and any combination thereof and an object can include a swab, suture thread, a towel, a sponge, a knife blade, a scalpel blade, a pin, a safety pin, a tip, tube, an adapter, a guide such as a cutting guide, a measurement device and any combination thereof.

An interaction involves a relationship between at least two articles, such as a predetermined distance between the articles, a predetermined angle between the articles, at least one article in a predetermined orientation with respect to at least one other article, a predetermined difference in speed between at least two articles, a predetermined difference in velocity and any combination thereof. Two articles are travelling at different speeds if the total distance one travels in a time interval Δt is different from the total distance the other travels in the time interval Δt. Two articles are travelling at different velocities if at least one of the following is true: they are traveling at different speeds, or they are traveling in different directions.

Examples of interactions include, but are not limited to:
Holding two hands at a fixed angle with relation to each other.
Tracking, which typically involves keeping a constant distance between an endoscope and at least one tool.
A suction tube can be kept a constant distance from an ablator, with the longitudinal axis of the tube at a fixed angle relative to the longitudinal axis of the ablator.
A grasper can be closed or kept closed if the distance between at least a portion of the grasper and tissue is smaller than a predetermined distance; similarly, a grasper can be opened if the distance between at least a portion of the grasper and the tissue is greater than a predetermined distance.
If two retractors are closer to tissue than a predetermined amount and closer to each other than a different predetermined amount, maintaining the retractors a fixed distance apart, with the flats of their blades parallel to each other. Optionally, the retractors can be maintained a fixed distance from the tissue. This interaction can be used, for example, to keep an incision in an organ open with minimum stress on the tissue, even if the organ is moved.
A fluid delivery tube and a suction tube can be kept fixed distances (which need not be the same) from a cautery, with a fixed angle between the tip of the fluid delivery tube, the tip of the cautery and the tip of the suction tube. In addition, the longitudinal axes of the tubes can be at fixed angles (which need not be the same) relative to the longitudinal axis of the cautery
The speed with which a tool moves toward an organ can be kept below a maximum.
Many more examples will be obvious to one skilled in the art.

Figure 32:
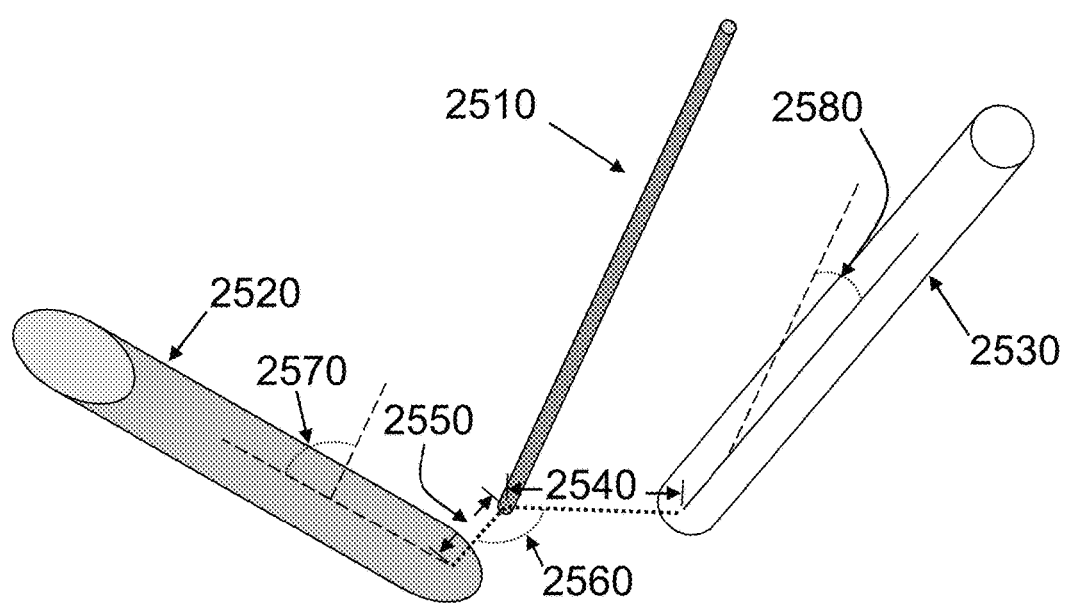
FIG. 32 schematically illustrates an embodiment of a tracking system with an input protocol in which a predetermined relationship is maintained between objects in afield of view.

A non-limiting example of a relationship between articles is shown in FIG. 32.

In this example, a fluid delivery tube (2520) and a suction tube (2530) are kept at fixed distances (2540, 2550), which are not the same, from a cautery (2510). A predetermined angle (2560) is maintained between the tip of the fluid delivery tube (2520), the tip of the cautery (2510) and the tip of the suction tube (2530). In addition, the longitudinal axes of the tubes are at fixed angles (2570, 2580), not the same, relative to the longitudinal axis of the cautery.

The embodiments shown hereinabove are merely exemplary—there are many input protocols, many output protocols and many associations between input protocol and output protocol which are possible and have not been shown.

It should be noted that the association of input and output protocols are typically arbitrary; any input protocol can be associated with any output protocol.

In the foregoing description, embodiments of the invention, including preferred embodiments, have been presented for the purpose of illustration and description. They are not intended to be exhaustive or to limit the invention to the precise form disclosed. Obvious modifications or variations are possible in light of the above teachings. The embodiments were chosen and described to provide the best illustration of the principals of the invention and its practical application, and to enable one of ordinary skill in the art to utilize the invention in various embodiments and with various modifications as are suited to the particular use contemplated. All such modifications and variations are within the scope of the invention as determined by the appended claims when interpreted in accordance with the breadth they are fairly, legally, and equitably entitled.

The invention claimed is:

1. A surgical controlling system, comprising:
   a. at least one surgical tool configured to be inserted into a surgical environment of a human body for assisting a surgical procedure;
   b. at least one location estimating means configured to real-time locate a 3D spatial position of said at least one surgical tool at any given time t;
   c. at least one movement detection means communicable with a movement's database and with said location estimating means; said movement's database is configured to store said 3D spatial position of said at least one surgical tool at time $t_f$ and at time $t_0$; where $t_f > t_0$; said movement detection means is configured to detect movement of said at least one surgical tool if said 3D spatial position of said at least one surgical tool at time $t_f$ is different than said 3D spatial position of said at least one surgical tool at time $t_0$; and,
   d. a controller having a processor communicable with a controller's database, said controller configured to control said spatial position of said at least one surgical tool; said controller's database is in communication with said movement detection means;
   wherein said controller's database is configured to store a predetermined set of rules according to which allowed movement and restricted movement of said at least one surgical tool are determinable; each detected movement by said movement detection means of said at least one surgical tool being real-time determinable as either said allowed movement or as said restricted movement according to said predetermined set of rules;
   wherein said surgical controlling system is configured, via said predetermined set of rules, to automatically guide and relocate said at least one surgical tool to a predetermined region of interest;
   further wherein said predetermined set of rules comprises at least one rule selected from a group consisting of: maximum speed rule, virtual zoom rule, virtual rotation of scene rule, and any combination thereof.

2. The surgical controlling system according to claim 1, wherein said maximum speed rule comprises a communicable database; said communicable database is configured to real-time receive and store at least one speed of at least one of said at least one surgical tool; said maximum speed rule is configured to determine said allowed movement and said restricted movement according to said at least one speed; said allowed movement being movement in which said at least one speed of said at least one surgical tool is below a predetermined value, and said restricted movement being movement in which said at least one speed of said at least one surgical tool is above a predetermined value; said allowed movement being movement tracking said at least one surgical tool and said restricted movement is discontinuation of tracking of said at least one surgical tool.

3. The surgical controlling system according to claim 1, wherein, in said maximum speed rule, at least one of the following being true: (a) said system constantly monitors speed of at least one of said at least one surgical tool, terminating tracking if said speed is above a predetermined maximum speed, (b) said system constantly monitors speed of movement of an endoscope, terminating tracking if said speed of said endoscope is above a predetermined maximum speed.

4. The surgical controlling system according to claim 1, wherein in said virtual zoom rule, for a zoom movement of said endoscope comprising at least one restricted movement of said endoscope, said zoom movement is performable via a virtual zooming.

5. The surgical controlling system according to claim 1, wherein in said virtual rotation of scene rule, said system is configured to maintain orientation of a displayed image unaffected by rotation of said endoscope.

6. The surgical controlling system according to claim 1, additionally comprising a position of tool rule, said position of tool rule comprises a communicable database comprising n 3D spatial positions; n is an integer greater than or equal to 2; said n 3D spatial positions define a predetermined volume within said surgical environment;
   said communicable database is configured to real-time receive and store at least one 3D position of at least one of said at least one surgical tool to be tracked, said at least one of said at least one surgical tool being at least one tracked tool;
   said position of tool rule is configured to determine said allowed movement and said restricted movement according to said at least one 3D position of said at least one tracked tool; said allowed movement being movement in which at least one of said at least one 3D position of said at least one tracked tool is within said predetermined volume, and said restricted movement being movement in which said 3D position of said at least one tracked tool is outside said predetermined volume; said allowed movement being movement tracking said at least one tracked tool and said restricted movement being discontinuation of said tracking of said at least one tracked tool.

7. The surgical controlling system according to claim 6, wherein, in said position of tool rule, said system constantly monitors said at least one 3D position of said at least one tracked tool, terminating said tracking if said at least one tracked tool is within said predetermined volume.

8. The surgical controlling system according to claim 1, wherein said predetermined set of rules further comprises at least one rule selected from a group consisting of: most used tool rule, right tool rule, left tool rule, field of view rule, no fly zone rule, route rule, environmental rule, operator input rule, proximity rule; collision prevention rule, history-based rule, tool-dependent allowed and restricted movement rule, preferred volume zone rule, preferred tool rule, movement detection rule, tagged tool rule, fixed point rule, change of speed rule and any combination thereof.

9. The surgical controlling system according to claim 8, wherein said fixed point rule comprises a communicable database; said communicable database configured to receive a definition of at least one fixed point, said definition of said at least one fixed point being at least one 3D position determined by a function of at least one predetermined 3D position; said fixed point rule is configured to determine said allowed movement and said restricted movement according to said at least one fixed point; said allowed movement being movement in which said at least one fixed point is located substantially in said at least one 3D position, and said restricted movement being movement in which the location of said at least one fixed point is substantially different from said at least one 3D position.

10. The surgical controlling system according to claim 9, wherein said predetermined position is selected from a group consisting of a tip of said at least one surgical tool, at least one position on at least one of said surgical tool; at least one position on at least one tissue; at least one tissue, at least one position on at least one organ; at least one organ, at least one 3D position within said surgical environment, and any combination thereof.

11. The surgical controlling system according to claim 8, wherein said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movement being movement in which said at least one surgical tool is located substantially in at least one of said n 3D spatial positions of said predefined route, and said restricted movement being movement in which said location of said at least one surgical tool is substantially different from said n 3D spatial positions of said predefined route.

12. The surgical controlling system according to claim 8, wherein said environmental rule comprises a comprises a communicable database; said communicable database is configured to receive at least one real-time image of said surgical environment and is configured to perform real-time image processing of the same and to determine at least one 3D spatial position of at least one hazard or obstacle in said surgical environment; said environmental rule is configured to determine said allowed movement and said restricted movement according to said at least one hazard or obstacle in said surgical environment; said restricted movement being movement in which said at least one surgical tool is located substantially in at least one of said at least one 3D spatial position of said at least one hazard or obstacle and said allowed movement being movement in which the location of said at least one surgical tool is substantially different from said at least one 3D spatial position of said at least one hazard or obstacle; said at least one hazard or obstacle in said surgical environment being selected from a group consisting of tissue, a surgical tool, an organ, an endoscope, and any combination thereof.

13. The surgical controlling system according to claim 8, wherein said operator input rule comprises a communicable database; said communicable database is configured to receive an input from the operator of said system regarding said allowed movement and said restricted movement of said at least one surgical tool; said operator input rule is configured to convert said allowed movement to said restricted movement and said restricted movement to said allowed movement; at least one of the following being true: (a) said input comprises n 3D spatial positions; n is an integer greater than or equal to 2; at least one of which being defined as allowed location and at least one of which is defined as restricted location; said allowed movement being movement in which said at least one surgical tool is located substantially in at least one of said n 3D spatial positions, and said restricted movement being movement in which the location of said at least one surgical tool is substantially different from said n 3D spatial positions; (b) said input comprises at least one rule according to which said allowed movement and said restricted movement of said at least one surgical tool are determinable; the spatial position of said at least one surgical tool is controlled by said controller according to said allowed movement and said restricted movement; said predetermined set of rules comprises at least one rule selected from a group consisting of: most used tool, right tool rule, left tool rule, field of view rule, no fly zone rule, route rule, environmental rule, operator input rule, proximity rule; collision prevention rule, preferred volume zone rule, preferred tool rule, movement detection rule, history-based rule, tool-dependent allowed and restricted movement rule, and any combination thereof.

14. The surgical controlling system according to claim 8, wherein said proximity rule is configured to define a predetermined distance between at least two articles; said allowed movement being movement which is within a range or out of a range of said predetermined distance, and said restricted movement being movement which is out of a range or within a range of said predetermined distance; each said article is selected from a group consisting of a surgical tool, a tissue, an organ, and any combination thereof.

15. The surgical controlling system according to claim 8, wherein said proximity rule is configured to define a predetermined angle between at least two articles; said allowed movement is movement which is within a range or out of a range of said predetermined angle, and said restricted movement is movement which is out of a range or within a range of said predetermined angle; each said article is selected from a group consisting of a surgical tool, a tissue, an organ, and any combination thereof.

16. The surgical controlling system according to claim 8, wherein said collision prevention rule is configured to define a predetermined distance between said at least one surgical tool and an anatomical element within said surgical environment; said allowed movement being movement which is in a range that is larger than said predetermined distance, and said restricted movement being movement which is in a range that is smaller than said predetermined distance; said anatomical element being selected from a group consisting of tissue, organ, another surgical tool, and any combination thereof.

17. The surgical controlling system according to claim 8, wherein in said change of speed rule, said system constantly monitors the distance between said endoscope's tip and at least one object within the surgical environment; the speed of said endoscope being variable as a function of said distance.

18. The surgical controlling system according to claim 8, wherein said right tool rule is configured to determine said allowed movement of said endoscope according to movement of at least one said surgical tool positioned to right of said endoscope; said left tool rule being configured to determine said allowed movement of said endoscope according to movement of at least one said surgical tool positioned to left of said endoscope.

19. The surgical controlling system according to claim 8, wherein said field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view; said allowed movement being movement in which said endoscope is located substantially in at least one of said n 3D spatial positions, and said restricted movement being movement in which the location of said endoscope is substantially different from said n 3D spatial positions.

20. The surgical controlling system according to claim 8, wherein said preferred volume zone rule comprises a communicable database comprising n 3D spatial positions; n is an integer greater than or equal to 2; said n 3D spatial positions provide said preferred volume zone; said preferred volume zone rule is configured to determine said allowed movement of said at least one surgical tool within said n 3D spatial positions and said restricted movement of said at least one surgical tool outside said n 3D spatial positions; said allowed movement being movement in which said at least one surgical tool is located substantially in at least one of said n 3D spatial positions, and said restricted movement being movement in which the location of said at least one surgical tool is substantially different from said n 3D spatial positions.

21. The surgical controlling system according to claim 8, wherein said preferred tool rule comprises a communicable database, said database stores a preferred tool; said preferred tool rule is configured to determine said allowed movement of an endoscope to constantly track movement of said preferred tool; and any combination thereof.

22. The surgical controlling system according to claim 8, wherein said most used tool rule comprises a communicable database counting the amount of movement of each of said at least one surgical tools; said most used tool rule is configured to constantly position said endoscope to track movement of a most moved surgical tool.

23. The surgical controlling system according to claim 8, wherein said movement detection rule comprises a communicable database comprising at least one real-time 3D spatial position of each of said at least one surgical tool; said movement detection rule is configured to detect movement of said at least one surgical tool when a change in said 3D spatial positions is received; said allowed movement being movement in which said endoscope is re-directed to focus on said moving surgical tool.

24. The surgical controlling system according to claim 8, wherein said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and said allowed movement if said movement is outside said no fly zone; said restricted movement being movement in which at least one of said at least one surgical tool is located substantially in at least one of said n 3D spatial positions, and said allowed movement being movement in which the location of said at least one of said at least one surgical tool is substantially different from all of said n 3D spatial positions.

25. The surgical controlling system according to claim 8, wherein said history-based rule comprises a communicable database storing each 3D spatial position of each of said at least one surgical tool; each movement of each of said at least one surgical tool being stored; said history-based rule is configured to determine said allowed movement and said restricted movement according to historical movements of said at least one surgical tool; said allowed movement being movement in which said at least one surgical tool is located substantially in at least one of said 3D spatial positions, and said restricted movement being movement in which the location of said at least one surgical tool is substantially different from said 3D spatial positions.

26. The surgical controlling system according to claim 8, wherein said tool-dependent allowed and restricted movement rule comprises a communicable database; said communicable database is configured to store predetermined characteristics of at least one of said at least one surgical tool; said tool-dependent allowed and restricted movement rule is configured to determine said allowed movement and said restricted movement according to said predetermined characteristics of said at least one of said at least one surgical tool; said allowed movement being movement of said endoscope tracking said at least one of said at least one surgical tool having said predetermined characteristics; said predetermined characteristics of said at least one of said at least one surgical tool being selected from a group consisting of: physical dimensions, structure, weight, sharpness, and any combination thereof.

27. The surgical controlling system according to claim 1, wherein at least one of the following is true (a) said system additionally comprises an endoscope; said endoscope is configured to provide at least one real-time image of said surgical environment; (b) at least one of said at least one surgical tool is an endoscope configured to provide at least one real-time image of said surgical environment.

28. The surgical controlling system according to claim 27, wherein said predetermined set of rules further comprises at least one rule selected from a group consisting of: most used tool rule, right tool rule, left tool rule, field of view rule, no fly zone rule, route rule, environmental rule, operator input rule, proximity rule; collision prevention rule, history-based rule, tool-dependent allowed and restricted movement rule, preferred volume zone rule, preferred tool rule, movement detection rule, tagged tool rule, change of speed rule, fixed point rule, maximum speed rule, virtual zoom rule, virtual rotation of scene rule, position of tool rule, and any combination thereof;

at least one of the following being true:
(a) said right tool rule is configured to determine said allowed movement of said endoscope according to movement of at least one said surgical tool positioned to right of said endoscope; said left tool rule being configured to determine said allowed movement of said endoscope according to movement of at least one said surgical tool positioned to left of said endoscope;
(b) said tagged tool rule comprises means configured to tag at least one surgical tool within said surgical environment and to determine said allowed movement of said endoscope to constantly track the movement of said tagged surgical tool;
(c) said field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view; said allowed movement being movement in which said endoscope is located substantially in at least one of said n 3D spatial positions, and said restricted movement being movement in which the location of said endoscope is substantially different from said n 3D spatial positions;
(d) said preferred volume zone rule comprises a communicable database comprising n 3D spatial positions; n is an integer greater than or equal to 2; said n 3D spatial positions provide said preferred volume zone; said preferred volume zone rule is configured to determine said allowed movement of said endoscope within said n 3D spatial positions and said restricted movement of said endoscope outside said n 3D spatial positions; said allowed movement being movement in which said endoscope is located substantially in at least one of said n 3D spatial positions, and said restricted movement being movement in which the location of said endoscope is substantially different from said n 3D spatial positions;

(e) said preferred tool rule comprises a communicable database, said database stores a preferred tool; said preferred tool rule is configured to determine said allowed movement of said endoscope to constantly track movement of said preferred tool; and any combination thereof;

(f) said most used tool rule comprises a communicable database counting the amount of movement of each of said surgical tools; said most used tool rule is configured to constantly position said endoscope to track movement of the most moved surgical tool;

(g) said movement detection rule comprises a communicable database comprising the real-time 3D spatial positions of each of said surgical tool; said movement detection rule is configured to detect movement of said at least one surgical tool when a change in said 3D spatial positions is received; said allowed movement being movement in which said endoscope is re-directed to focus on said moving surgical tool;

(h) in said change of speed rule, said system constantly monitors the distance between said endoscope's tip and at least one object within the surgical environment, the speed of said endoscope being variable as a function of said distance;

(i) said maximum speed rule comprises a communicable database; said communicable database is configured to real-time receive and store at least one speed of at least one of said at least one surgical tool; said maximum speed rule is configured to determine said allowed movement and said restricted movement according to said at least one speed; said allowed movement being movement in which at least one speed of said at least one surgical tool is below a predetermined value, and said restricted movement being movement in which said at least one speed of said at least one surgical tool is above a predetermined value; said allowed movement being tracking said at least one surgical tool and said restricted movement being discontinuation of tracking of said at least one surgical tool;

(j) in said maximum speed rule, at least one of the following is true: (i) said system constantly monitors speed of at least one said tagged tool, terminating tracking if said speed is above a predetermined maximum speed, (ii) said system constantly monitors speed of movement of said endoscope, terminating tracking if said speed of said endoscope is above a predetermined maximum speed;

(k) in said virtual zoom rule, for a zoom movement of said endoscope comprising at least one restricted movement of said endoscope, said zoom movement is performable via a virtual zooming;

(l) in said virtual rotation of scene rule, said system is configured to maintain orientation of a displayed image unaffected by rotation of said endoscope;

(m) said position of tool rule comprises a communicable database comprising n 3D spatial positions; n is an integer greater than or equal to 2; said n 3D spatial positions define a predetermined volume within said surgical environment; said communicable database is configured to real-time receive and store at least one 3D position of at least one of said at least one surgical tool to be tracked, said at least one of said at least one surgical tool to be tracked being at least one tracked tool; said position of tool rule is configured to determine said allowed movement and said restricted movement according to said at least one 3D position of said at least one tracked tool; said allowed movement being movement in which at least one of said at least one 3D position of said at least one tracked tool is within said predetermined volume, and said restricted movement being movement in which said at least one 3D position of said at least one tracked tool is outside said predetermined volume; said allowed movement being movement tracking said at least one tracked tool and said restricted movement being discontinuation of said tracking of said at least one tracked tool;

(n) in said position of tool rule, said system constantly monitors said at least one 3D position of said at least one tracked tool, terminating said tracking if said at least one tracked tool is within said predetermined volume;

(o) said fixed point rule comprises a communicable database; said communicable database configured to receive a definition of at least one fixed point; said definition of said at least one fixed point being at least one 3D position determined by a function of at least one predetermined 3D position; said fixed point rule is configured to determine said allowed movement and said restricted movement according to said at least one fixed point; said allowed movement being movement in which said at least one fixed point is located substantially in said at least one 3D position, and said restricted movement being movement in which the location of said at least one fixed point is substantially different from said 3D at least one 3D position; said predetermined position is selected from a group consisting of a tip of said at least one surgical tool, at least one position on said at least one surgical tool; at least one position on at least one tissue; at least one tissue, at least one position on at least one organ; at least one organ, at least one 3D position within said surgical environment, and any combination thereof; and (p) any combination thereof.

29. The surgical controlling system according to claim 28, wherein at least one of the following is true:

a. said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movement being movement in which said at least one surgical tool is located substantially in at least one of said n 3D spatial positions of said predefined route, and said restricted movement being movement in which said location of said at least one surgical tool is substantially different from said n 3D spatial positions of said predefined route;

b. said environmental rule comprises a comprises a communicable database; said communicable database configured to receive at least one real-time image of said surgical environment and is configured to perform real-time image processing of the same and to determine at least one 3D spatial position of at least one hazard or obstacle in said surgical environment; said environmental rule is configured to determine said allowed movement and said restricted movement according to said at least one hazard or obstacle in said surgical environment; said restricted movement being movement in which said at least one surgical tool is located substantially in at least one of said at least one 3D spatial position of said at least one hazard or obstacle, and said allowed movement being movement in which the location of said at least one surgical tool is substantially different from said at least one 3D spatial position of said at least one hazard or obstacle; said at least one hazard or obstacle in said surgical environment being selected from a group consisting of tissue, a surgical tool, an organ, an endoscope, and any combination thereof;

c. said operator input rule comprises a communicable database; said communicable database is configured to receive an input from the operator of said system regarding said allowed movement and said restricted movement of said at least one surgical tool; said operator input rule is configured to convert said allowed movement to said restricted movement and said restricted movement to said allowed movement; at least one of the following being true (a) said input comprises n 3D spatial positions; n is an integer greater than or equal to 2; at least one of which being defined as allowed location and at least one of which being defined as restricted location, said allowed movement being movement in which said at least one surgical tool is located substantially in at least one of said n 3D spatial positions, and said restricted movement being movement in which the location of said at least one surgical tool is substantially different from said n 3D spatial positions; (b) said input comprises at least one rule according to which said allowed movement and said restricted movement of said at least one surgical tool are determinable, the spatial position of said at least one surgical tool is controlled by said controller according to said allowed movement and said restricted movement; said predetermined set of rules comprises at least one rule selected from a group consisting of: most used tool, right tool rule, left tool rule, field of view rule, no fly zone rule, route rule, environmental rule, operator input rule, proximity rule; collision prevention rule, preferred volume zone rule, preferred tool rule, movement detection rule, history-based rule, tool-dependent allowed and restricted movement rule, and any combination thereof;

d. said proximity rule is configured to define a predetermined distance between at least two articles; said allowed movement being movement which is within a range or out of a range of said predetermined distance, and said restricted movement being movement which is out of a range or within a range of said predetermined distance; each said article is selected from a group consisting of a surgical tool, a tissue, an organ, and any combination thereof;

e. said proximity rule is configured to define a predetermined angle between at least two articles; said allowed movement being movement which is within a range or out of a range of said predetermined angle, and said restricted movement being movement which is out of a range or within a range of said predetermined angle; each said article is selected from a group consisting of a surgical tool, a tissue, an organ, and any combination thereof;

f. said collision prevention rule is configured to define a predetermined distance between said at least one surgical tool and an anatomical element within said surgical environment; said allowed movement being movement which is in a range that is larger than said predetermined distance, and said restricted movement being movement which is in a range that is smaller than said predetermined distance; said anatomical element being selected from a group consisting of tissue, organ, another surgical tool, and any combination thereof;

g. said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and said allowed movement if said movement is outside said no fly zone, said restricted movement being movement in which at least one of said at least one surgical tool is located substantially in at least one of said n 3D spatial positions, and said allowed movement being movement in which the location of said at least one of said at least one surgical tool is substantially different from all of said n 3D spatial positions;

h. said history-based rule comprises a communicable database storing each 3D spatial position of each of said at least one surgical tool, each movement of each of said at least one surgical tool being stored; said history-based rule is configured to determine said allowed movement and said restricted movement according to historical movements of said at least one surgical tool; said allowed movement being movement in which said at least one surgical tool is located substantially in at least one of said 3D spatial positions, and said restricted movement being movement in which the location of said at least one surgical tool is substantially different from said 3D spatial positions;

i. said tool-dependent allowed and restricted movement rule comprises a communicable database; said communicable database is configured to store predetermined characteristics of at least one of said at least one surgical tool; said tool-dependent allowed and restricted movement rule is configured to determine said allowed movement and said restricted movement according to said predetermined characteristics of said at least one of said at least one surgical tool; said allowed movement being movement of said endoscope which tracks said at least one of said at least one surgical tool having said predetermined characteristics; said predetermined characteristics of said at least one of said at least one surgical tool being selected from a group consisting of: physical dimensions, structure, weight, sharpness, and any combination thereof; and j. any combination thereof.

30. The surgical controlling system according to claim 1, wherein said system further comprises a maneuvering subsystem communicable with said controller, said maneuvering subsystem is configured to spatially reposition said at least one surgical tool during a surgery according to said predetermined set of rules.

31. The surgical controlling system according to claim 1, wherein said system is configured to provide an alert of said restricted movement of said at least one surgical tool; said alert being selected from a group consisting of audio signaling, voice signaling, light signaling, flashing signaling, and any combination thereof.

32. The surgical controlling system according to claim 1, wherein at least one of the following is true (a) said at least one location estimating means comprises at least one endoscope configured to acquire real-time images of said surgical environment within said human body; and at least one surgical instrument spatial location software configured to receive said real-time images of said surgical environment and to estimate said 3D spatial position of said at least one surgical tool; (b) said at least one location estimating means comprises (i) at least one element selected from a group consisting of optical imaging means, radio frequency transmitting and receiving means, at least one mark on said at least one surgical tool, and any combination thereof; and, (ii) at least one surgical instrument spatial location software configured to estimate said 3D spatial position of said at least one surgical tool by means of said element; (c) said at least one location estimating means comprises an interface subsystem between a surgeon and the at least one surgical tool, the interface subsystem comprises: (i) at least one array comprising N regular or pattern light sources, where N is a positive integer; (ii) at least one array comprising M cameras, each of the M cameras, where M is a positive integer; (iii) optional optical markers and means for attaching the optical marker to the at least one surgical tool; and; (iv) a computerized algorithm operable via the controller, the computerized algorithm configured to record images received by each camera of each of the M cameras and to calculate therefrom the position of each of the tools, and further configured to provide automatically the results of the calculation to the human operator of the interface.

33. A method for assisting an operator to perform a surgical procedure, comprising steps of:
   a. providing a surgical controlling system, comprising: (i) at least one surgical tool; (ii) at least one location estimating means; (iii) at least one movement detection means; and, (iv) a controller having a processor communicable with a controller's database; said controller's database is in communication with said movement detection means:
   b. inserting said at least one surgical tool into a surgical environment of a human body;
   c. real-time estimating the location of said at least one surgical tool within said surgical environment at any given time t;
   d. detecting if there is movement of said at least one surgical tool if a 3D spatial position of said at least one surgical tool at time $t_f$ is different than said 3D spatial position of said at least one surgical tool at time $t_O$; and
   e. controlling said spatial position of said at least one surgical tool within said surgical environment by means of said controller;
   wherein said step of controlling is performed by (a) storing a predetermined set of rules in a controller's database; said predetermined set of rules comprises allowed movement and restricted movement of said at least one surgical tool; and (b) real-time determining each detected movement by said movement detection means of said at least one surgical tool as either said allowed movement or as said restricted movement according to said predetermined set of rules;
   wherein said surgical controlling system is configured, via said predetermined set of rules, to automatically guide and relocate said at least one surgical tool to a predetermined region of interest;
   further wherein said predetermined set of rules comprises at least one rule selected from a group consisting of maximum speed rule, virtual zoom rule, virtual rotation of scene rule, and any combination thereof.

34. The method according to claim 33, wherein said maximum speed rule comprises a communicable database; said communicable database is configured to real-time receive and store at least one speed of at least one of said at least one surgical tool; said maximum speed rule is configured to determine said allowed movement and said restricted movement according to said at least one speed, said allowed movement being movement in which said at least one speed of said at least one surgical tool is below a predetermined value, and said restricted movement being movement in which said at least one speed of said at least one surgical tool is above a predetermined value; said allowed movement being movement tracking said at least one surgical tool and said restricted movement being discontinuation of tracking of said at least one surgical tool.

35. The method according to claim 33, wherein, in said maximum speed rule, at least one of the following is true: (a) said system constantly monitors speed of at least one said tagged tool, terminating tracking if said speed is above a predetermined maximum speed, (b) said system constantly monitors speed of movement of an endoscope, terminating tracking if said speed of said endoscope is above a predetermined maximum speed.

36. The method according to claim 33, wherein, in said virtual zoom rule, for a zoom movement of said endoscope comprising at least one restricted movement of said endoscope, said zoom movement is performable via a virtual zooming.

37. The method according to claim 33, wherein, in said virtual rotation of scene rule, said system is configured to maintain orientation of a displayed image unaffected by rotation of said endoscope.

38. The method according to claim 33, additionally comprising a position of tool rule, said position of tool rule comprising a communicable database; comprising n 3D spatial positions; n is an integer greater than or equal to 2; said n 3D spatial positions define a predetermined volume within said surgical environment;
   said communicable database is configured to real-time receive and store at least one 3D position of at least one of said at least one surgical tool to be tracked, said at least one of said at least one surgical tool being at least one tracked tool;
   said position of tool rule is configured to determine said allowed movement and said restricted movement according to said at least one 3D position of said at least one tracked tool; said allowed movement being movement in which at least one of said at least one 3D position of said at least one tracked tool is within said predetermined volume, and said restricted movement being movement in which said at least one 3D position of said at least one tracked tool is outside said predetermined volume; said allowed movement being movement tracking said at least one tracked tool and said restricted movement is discontinuation of said tracking of said at least one tracked tool.

39. The method according to claim 33, wherein, in said position of tool rule, said system constantly monitors said at least one 3D position of said at least one tracked tool, terminating said tracking if said tracked tool is within said predetermined volume.

40. The method according to claim 33, wherein said predetermined set of rules further comprises at least one rule selected from a group consisting of: most used tool rule, right tool rule, left tool rule, field of view rule, no fly zone rule, route rule, environmental rule, operator input rule, proximity rule; collision prevention rule, history-based rule, tool-dependent allowed and restricted movement rule, preferred volume zone rule, preferred tool rule, movement detection rule, tagged tool rule, fixed point rule, change of speed rule and any combination thereof.

41. The method according to claim 40, wherein said fixed point rule comprises a communicable database; said communicable database configured to receive a definition of at least one fixed point, said definition of said at least one fixed point being at least one 3D position determined by a function of at least one predetermined 3D position; said fixed point rule is configured to determine said allowed movement and said restricted movement according to said at least one fixed point; said allowed movement being movement in which location of said at least one fixed point is substantially in said at least one 3D position, and said restricted movement being movement in which the location of said at least one fixed point is substantially different from said at least one 3D position.

42. The method according to claim 41, wherein said at least one 3D position to be tracked is defined as a function of a predetermined position within said surgical environment; said predetermined position is selected from a group consisting of a tip of said at least one surgical tool, at least one position on at least one of said surgical tool; at least one position on at least one tissue; at least one tissue, at least one position on at least one organ; at least one organ, at least one 3D position within said surgical environment, and any combination thereof.

43. The method according to claim 40, wherein said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movement being movement in which said at least one surgical tool is located substantially in at least one of said n 3D spatial positions of said predefined route, and said restricted movement being movement in which said location of said at least one surgical tool is substantially different from said n 3D spatial positions of said predefined route.

44. The method according to claim 40, wherein said environmental rule comprises a communicable database; said communicable database configured to receive at least one real-time image of said surgical environment and is configured to perform real-time image processing of the same and to determine at least one 3D spatial position of at least one hazard or obstacle in said surgical environment; said environmental rule is configured to determine said allowed movement and said restricted movement according to said at least one hazard or obstacle in said surgical environment, said restricted movement being movement in which said at least one surgical tool is located substantially in at least one of said at least one 3D spatial position of said at least one hazard or obstacle, and said allowed movement being movement in which the location of said at least one surgical tool is substantially different from said at least one 3D spatial position of said at least one hazard or obstacle; said at least one hazard or obstacle in said surgical environment being selected from a group consisting of tissue, a surgical tool, an organ, an endoscope, and any combination thereof.

45. The method according to claim 40, wherein said operator input rule comprises a communicable database; said communicable database is configured to receive an input from the operator of said system regarding said allowed movement and said restricted movement of said at least one surgical tool; said operator input rule is configured to convert said allowed movement to said restricted movement and said restricted movement to said allowed movement; at least one of the following being true (a) said input comprises n 3D spatial positions; n is an integer greater than or equal to 2; at least one of which being defined as allowed location and at least one of which is defined as restricted location; said allowed movement being movement in which said at least one surgical tool is located substantially in at least one of said n 3D spatial positions, and said restricted movement being movement in which the location of said at least one surgical tool is substantially different from said n 3D spatial positions; (b) said input comprises at least one rule according to which said allowed movement and said restricted movement of said at least one surgical tool are determinable; the spatial position of said at least one surgical tool is controlled by said controller according to said allowed movement and said restricted movement; said predetermined set of rules comprises at least one rule selected from a group consisting of: most used tool, right tool rule, left tool rule, field of view rule, no fly zone rule, route rule, environmental rule, operator input rule, proximity rule; collision prevention rule, preferred volume zone rule, preferred tool rule, movement detection rule, history-based rule, tool-dependent allowed and restricted movement rule, and any combination thereof.

46. The method according to claim 40, wherein said proximity rule is configured to define a predetermined distance between at least two articles; said allowed movement being movement which is within a range or out of a range of said predetermined distance, and said restricted movement being movement which is out of a range or within a range of said predetermined distance; each said article is selected from a group consisting of a surgical tool, a tissue, an organ, and any combination thereof.

47. The method according to claim 40, wherein said proximity rule is configured to define a predetermined angle between at least two articles; said allowed movement being movement which is within a range or out of a range of said predetermined angle, and said restricted movement being movement which is out of a range or within a range of said predetermined angle; each said article is selected from a group consisting of a surgical tool, a tissue, an organ, and any combination thereof.

48. The method according to claim 40, wherein said collision prevention rule is configured to define a predetermined distance between said at least one surgical tool and an anatomical element within said surgical environment; said allowed movement being movement which is in a range that is larger than said predetermined distance, and said restricted movement being movement which is in a range that is smaller than said predetermined distance; said anatomical element being selected from a group consisting of tissue, organ, another surgical tool, and any combination thereof.

49. The method according to claim 40, wherein in said change of speed rule, said system constantly monitors the distance between said endoscope's tip and at least one object within the surgical environment; the speed of said endoscope being variable as a function of said distance.

50. The method according to claim 40, wherein said right tool rule is configured to determine said allowed movement of said endoscope according to movement of at least one said surgical tool positioned to right of said endoscope; said left tool rule being configured to determine said allowed movement of said endoscope according to movement of at least one said surgical tool positioned to left of said endoscope.

51. The method according to claim 40, wherein field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view, said allowed movement being movement in which said endoscope is located substantially in at least one of said n 3D spatial positions, and said restricted movement being movement in which the location of said endoscope is substantially different from said n 3D spatial positions.

52. The method according to claim 40, wherein said preferred volume zone rule comprises a communicable database comprising n 3D spatial positions; n is an integer greater than or equal to 2; said n 3D spatial positions provide said preferred volume zone; said preferred volume zone rule is configured to determine said allowed movement of said at least one surgical tool within said n 3D spatial positions and said restricted movement of said at least one surgical tool outside said n 3D spatial positions, said allowed movement being movement in which said at least one surgical tool is located substantially in at least one of said n 3D spatial positions, and said restricted movement being movement in which the location of said at least one surgical tool is substantially different from said n 3D spatial positions.

53. The method according to claim 40, wherein said preferred tool rule comprises a communicable database, said database stores a preferred tool; said preferred tool rule is configured to determine said allowed movement of said endoscope to constantly track movement of said preferred tool; and any combination thereof.

54. The method according to claim 40, wherein said most used tool rule comprises a communicable database counting the amount of movement of each of said surgical tools; said most used tool rule is configured to constantly position said endoscope to track movement of the most moved surgical tool.

55. The method according to claim 40, wherein said movement detection rule comprises a communicable database comprising at least one real-time 3D spatial positions of each of said at least one surgical tool; said movement detection rule is configured to detect movement of said at least one surgical tool when a change in said 3D spatial positions is received, said allowed movement being movement in which said endoscope is re-directed to focus on said moving surgical tool.

56. The method according to claim 40, wherein said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and said allowed movement if said movement is outside said no fly zone, said restricted movement being movement in which at least one of said at least one surgical tool is located substantially in at least one of said n 3D spatial positions, and said allowed movement being movement in which the location of said at least one surgical tool is substantially different from all of said n 3D spatial positions.

57. The method according to claim 40, wherein said history-based rule comprises a communicable database storing each 3D spatial position of each of said at least one surgical tool, each movement of each of said at least one surgical tool being stored; said history-based rule is configured to determine said allowed movement and said restricted movement according to historical movements of said at least one surgical tool, said allowed movement being movement in which said at least one surgical tool is located substantially in at least one of said 3D spatial positions, and said restricted movement being movement in which the location of said at least one surgical tool is substantially different from said 3D spatial positions.

58. The method according to claim 40, wherein said tool-dependent allowed and restricted movement rule comprises a communicable database; said communicable database is configured to store predetermined characteristics of at least one of said at least one surgical tool; said tool-dependent allowed and restricted movement rule is configured to determine said allowed movement and said restricted movement according to said predetermined characteristics of said at least one of said at least one surgical tool; said allowed movement being movement of said endoscope tracking said at least one of said at least one surgical tool having said predetermined characteristics; said predetermined characteristics of said at least one of said at least one surgical tool being selected from a group consisting of: physical dimensions, structure, weight, sharpness, and any combination thereof.

59. The method according to claim 33, wherein at least one of the following is true (a) said system additionally comprises an endoscope; said endoscope is configured to provide at least one real-time image of said surgical environment; (b) at least one of said at least one surgical tool is an endoscope configured to provide at least one real-time image of said surgical environment.

60. The method according to claim 59, wherein said predetermined set of rules further comprises at least one rule selected from a group consisting of: most used tool rule, right tool rule, left tool rule, field of view rule, no fly zone rule, route rule, environmental rule, operator input rule, proximity rule; collision prevention rule, history-based rule, tool-dependent allowed and restricted movement rule, preferred volume zone rule, preferred tool rule, movement detection rule, tagged tool rule, change of speed rule, fixed point rule, maximum speed rule, virtual zoom rule, virtual rotation of scene rule, position of tool rule, and any combination thereof;

at least one of the following being true:
(a) said right tool rule is configured to determine said allowed movement of said endoscope according to movement of at least one said surgical tool positioned to right of said endoscope; said left tool rule being configured to determine said allowed movement of said endoscope according to movement of at least one said surgical tool positioned to left of said endoscope;
(b) said tagged tool rule comprises means configured to tag at least one surgical tool within said surgical environment and to determine said allowed movement of said endoscope to constantly track the movement of said tagged surgical tool;
(c) said field of view rule comprises a communicable database comprising n 3D spatial positions; n is an integer greater than or equal to 2; the combination of all of said n 3D spatial positions provides a predetermined field of view; said field of view rule is configured to determine said allowed movement of said endoscope within said n 3D spatial positions so as to maintain a constant field of view, said allowed movement being movement in which said endoscope is located substantially in at least one of said n 3D spatial positions, and said restricted movement being movement in which the location of said endoscope is substantially different from said n 3D spatial positions;

(d) said preferred volume zone rule comprises a communicable database comprising n 3D spatial positions; n is an integer greater than or equal to 2; said n 3D spatial positions provide said preferred volume zone; said preferred volume zone rule is configured to determine said allowed movement of said endoscope within said n 3D spatial positions and said restricted movement of said endoscope outside said n 3D spatial positions, said allowed movement being movement in which said endoscope is located substantially in at least one of said n 3D spatial positions, and said restricted movement being movement in which the location of said endoscope is substantially different from said n 3D spatial positions;

(e) said preferred tool rule comprises a communicable database, said database stores a preferred tool; said preferred tool rule is configured to determine said allowed movement of said endoscope to constantly track movement of said preferred tool; and any combination thereof;

(f) said most used tool rule comprises a communicable database counting the amount of movement of each of said surgical tools; said most used tool rule is configured to constantly position said endoscope to track movement of the most moved surgical tool;

(g) said movement detection rule comprises a communicable database comprising the real-time 3D spatial positions of each of said surgical tool; said movement detection rule is configured to detect movement of said at least one surgical tool when a change in said 3D spatial positions is received, said allowed movement being movement in which said endoscope is re-directed to focus on said moving surgical tool;

(h) in said change of speed rule, said system constantly monitors the distance between said endoscope's tip and at least one object within the surgical environment, the speed of said endoscope being variable as a function of said distance;

(i) said maximum speed rule comprises a communicable database; said communicable database is configured to real-time receive and store at least one speed of at least one said surgical tool; said maximum speed rule is configured to determine said allowed movement and said restricted movement according to said at least one speed, said allowed movement being movement in which said at least one speed of said at least one surgical tool is below a predetermined value, and said restricted movement being movement in which said at least one speed of said at least one surgical tool is above a predetermined value; said allowed movement being tracking of said at least one surgical tool and said restricted movement being discontinuation of tracking of said at least one surgical tool;

(j) in said maximum speed rule, at least one of the following is true: (i) said system constantly monitors speed of at least one said tagged tool, terminating tracking if said speed is above a predetermined maximum speed, (ii) said system constantly monitors speed of movement of said endoscope, terminating tracking if said speed of said endoscope is above a predetermined maximum speed;

(k) in said virtual zoom rule, for a zoom movement of said endoscope comprising at least one restricted movement of said endoscope, said zoom movement is performable via a virtual zooming;

(l) in said virtual rotation of scene rule, said system is configured to maintain orientation of a displayed image unaffected by rotation of said endoscope;

(m) said position of tool rule comprises a communicable database comprising n 3D spatial positions; n is an integer greater than or equal to 2; said n 3D spatial positions define a predetermined volume; said communicable database is configured to real-time receive and store at least one 3D position of at least one of said at least one surgical tool to be tracked, said at least one of said at least one surgical tool being at least one tracked tool; said position of tool rule is configured to determine said allowed movement and said restricted movement according to said at least one 3D position of said at least one tracked tool; said allowed movement being movement in which at least one of said at least one 3D position of said at least one tracked tool is within said predetermined volume, and said restricted movement being movement in which said 3D position of said at least one tracked tool is outside said predetermined volume; said allowed movement being movement tracking said at least one tool and said restricted movement being discontinuation of said tracking of said at least one tracked tool;

(n) in said position of tool rule, said system constantly monitors said at least one 3D position of said at least one tracked tool, terminating said tracking if said tagged tool is within said predetermined volume;

(o) said fixed point rule comprises a communicable database; said communicable database configured to receive a definition of at least one fixed point; said definition of said at least one fixed point being at least one 3D position determined by a function of at least one predetermined 3D position; said fixed point rule is configured to determine said allowed movement and said restricted movement according to said at least one fixed point; said allowed movement being movement in which said at least one fixed point is located substantially in said at least one 3D position, and said restricted movement being movement in which the location of said at least one fixed point is substantially different from said at least one 3D position; said predetermined position is selected from a group consisting of a tip of said at least one surgical tool, at least one position on at least one of said surgical tool; at least one position on at least one tissue; at least one tissue, at least one position on at least one organ; at least one organ, at least one 3D position within said surgical environment, and any combination thereof; and (p) any combination thereof.

61. The method according to claim 59, wherein at least one of the following is true:
 a. said route rule comprises a communicable database storing predefined route in which said at least one surgical tool is configured to move within said surgical environment; said predefined route comprises n 3D spatial positions of said at least one surgical tool; n is an integer greater than or equal to 2; said allowed movement being movement in which said at least one surgical tool is located substantially in at least one of said n 3D spatial positions of said predefined route, and said restricted movement being movement in which said location of said at least one surgical tool is substantially different from said n 3D spatial positions of said predefined route;

b. said environmental rule comprises a comprises a communicable database; said communicable database configured to receive at least one real-time image of said surgical environment and is configured to perform real-time image processing of the same and to determine at least one 3D spatial position of at least one hazard or obstacle in said surgical environment; said environmental rule is configured to determine said allowed movement and said restricted movement according to said at least one hazard or obstacle in said surgical environment, said restricted movement being movement in which said at least one surgical tool is located substantially in at least one of said at least one 3D spatial position of said at least one hazard or obstacle, and said allowed movement being movement in which the location of said at least one surgical tool is substantially different from said at least one 3D spatial position of said at least one hazard or obstacle; said at least one hazard or obstacle in said surgical environment being selected from a group consisting of tissue, a surgical tool, an organ, an endoscope, and any combination thereof;

c. said operator input rule comprises a communicable database; said communicable database is configured to receive an input from the operator of said system regarding said allowed movement and said restricted movement of said at least one surgical tool; said operator input rule is configured to convert said allowed movement to said restricted movement and said restricted movement to said allowed movement; at least one of the following being true: (a) said input comprises n 3D spatial positions; n is an integer greater than or equal to 2; at least one of which being defined as allowed location and at least one of which being defined as restricted location, said allowed movement being movement in which said at least one surgical tool is located substantially in at least one of said n 3D spatial positions, and said restricted movement being movement in which the location of said at least one surgical tool is substantially different from said n 3D spatial positions; (b) said input comprises at least one rule according to which said allowed movement and said restricted movement of said at least one surgical tool are determinable, the spatial position of said at least one surgical tool being controlled by said controller according to said allowed movement and said restricted movement; said predetermined set of rules comprises at least one rule selected from a group consisting of: most used tool, right tool rule, left tool rule, field of view rule, no fly zone rule, route rule, environmental rule, operator input rule, proximity rule; collision prevention rule, preferred volume zone rule, preferred tool rule, movement detection rule, history-based rule, tool-dependent allowed and restricted movement rule, and any combination thereof;

d. said proximity rule is configured to define a predetermined distance between at least two articles; said allowed movement being movement which is within a range or out of a range of said predetermined distance, and said restricted movement being movement which is out of a range or within a range of said predetermined distance; each said article is selected from a group consisting of a surgical tool, a tissue, an organ, and any combination thereof;

e. said proximity rule is configured to define a predetermined angle between at least two articles; said allowed movement being movement which is within a range or out of a range of said predetermined angle, and said restricted movement being movement which is out of a range or within a range of said predetermined angle; each said article is selected from a group consisting of a surgical tool, a tissue, an organ, and any combination thereof;

f. said collision prevention rule is configured to define a predetermined distance between said at least one surgical tool and an anatomical element within said surgical environment; said allowed movement being movement which is in a range that is larger than said predetermined distance, and said restricted movement being movement which is in a range that is smaller than said predetermined distance; said anatomical element being selected from a group consisting of tissue, organ, another surgical tool, and any combination thereof;

g. said no fly zone rule comprises a communicable database comprising n 3D spatial positions; n is an integer greater than or equal to 2; said n 3D spatial positions define a predetermined volume within said surgical environment; said no fly zone rule is configured to determine said restricted movement if said movement is within said no fly zone and said allowed movement if said movement is outside said no fly zone, said restricted movement being movement in which at least one of said at least one surgical tool is located substantially in at least one of said n 3D spatial positions, and said allowed movement being movement in which the location of said at least one of said at least one surgical tool is substantially different from all said n 3D spatial positions;

h. said history-based rule comprises a communicable database storing each 3D spatial position of each of said at least one surgical tool, each movement of each of said at least one surgical tool being stored; said history-based rule is configured to determine said allowed movement and said restricted movement according to historical movements of said at least one surgical tool, said allowed movement being movement in which said at least one surgical tool is located substantially in at least one of said 3D spatial positions, and said restricted movement being movement in which the location of said at least one surgical tool is substantially different from said 3D spatial positions;

i. said tool-dependent allowed and restricted movement rule comprises a communicable database; said communicable database is configured to store predetermined characteristics of at least one of said at least one surgical tool; said tool-dependent allowed and restricted movement rule is configured to determine said allowed movement and said restricted movement according to said predetermined characteristics of said at least one of said at least one surgical tool; said allowed movement being movement of said endoscope which track said at least one of said at least one surgical tool having said predetermined characteristics; said predetermined characteristics of said at least one of said at least one surgical tool being selected from a group consisting of: physical dimensions, structure, weight, sharpness, and any combination thereof; and j. any combination thereof.

62. The method according to claim 33, wherein said system further comprises a maneuvering subsystem communicable with said controller, said maneuvering subsystem is configured to spatially reposition said at least one surgical tool during a surgery according to said predetermined set of rules.

63. The method according to claim 33, wherein said system is configured to provide an alert of said restricted movement of said at least one surgical tool; said alert being selected from a group consisting of audio signaling, voice signaling, light signaling, flashing signaling, and any combination thereof.

64. The method according to claim 33, wherein at least one of the following is true (a) said at least one location estimating means comprises at least one endoscope configured to acquire real-time images of said surgical environment within said human body; and at least one surgical instrument spatial location software configured to receive said real-time images of said surgical environment and to estimate said 3D spatial position of said at least one surgical tool; (b) said at least one location estimating means comprises (i) at least one element selected from a group consisting of optical imaging means, radio frequency transmitting and receiving means, at least one mark on said at least one surgical tool, and any combination thereof; and, (ii) at least one surgical instrument spatial location software configured to estimate said 3D spatial position of said at least one surgical tool by means of said element; (c) said at least one location estimating means comprise an interface subsystem between a surgeon and the at least one surgical tool, the interface subsystem comprises: (i) at least one array comprising N regular or pattern light sources, where N is a positive integer; (ii) at least one array comprising M cameras, each of the M cameras, where M is a positive integer; (iii) optional optical markers and means for attaching the optical marker to the at least one surgical tool; and; (iv) a computerized algorithm operable via the controller, the computerized algorithm configured to record images received by each camera of each of the M cameras and to calculate therefrom the position of each of the tools, and further configured to provide automatically the results of the calculation to the human operator of the interface.

* * * * *